United States Patent
Otsuji et al.

(10) Patent No.: US 7,534,909 B2
(45) Date of Patent: May 19, 2009

(54) (METH) ACRYLIC ESTER COMPOUND AND USE THEREOF

(75) Inventors: Atsuo Otsuji, Sodegaura (JP); Masatoshi Takagi, Sodegaura (JP); Chojiro Higuchi, Sodegaura (JP); Akinori Nagatomo, Omuta (JP); Kouji Suesugi, Omuta (JP); Tetsuya Toida, Moriyama (JP); Narimichi Honda, Moriyama (JP)

(73) Assignee: Mitsui Chemicals, Inc., Tokyo (JP)

( * ) Notice: Subject to any disclaimer, the term of this patent is extended or adjusted under 35 U.S.C. 154(b) by 188 days.

(21) Appl. No.: 10/557,882

(22) PCT Filed: May 21, 2004

(86) PCT No.: PCT/JP2004/007327

§ 371 (c)(1),
(2), (4) Date: Nov. 22, 2005

(87) PCT Pub. No.: WO2004/103949

PCT Pub. Date: Dec. 2, 2004

(65) Prior Publication Data

US 2007/0078198 A1    Apr. 5, 2007

(30) Foreign Application Priority Data

May 23, 2003   (JP)   ............... 2003-145616
Aug. 1, 2003   (JP)   ............... 2003-284921
Oct. 16, 2003  (JP)   ............... 2003-356465

(51) Int. Cl.
| | |
|---|---|
| C07C 69/54 | (2006.01) |
| C07C 43/23 | (2006.01) |
| C07C 69/63 | (2006.01) |
| C07C 323/20 | (2006.01) |
| C08F 20/30 | (2006.01) |
| A61C 13/087 | (2006.01) |
| G02B 1/04 | (2006.01) |

(52) U.S. Cl. ............... 560/225; 560/205; 560/220; 560/221; 106/35

(58) Field of Classification Search ............... None
See application file for complete search history.

(56) References Cited

U.S. PATENT DOCUMENTS

| | | | |
|---|---|---|---|
| 4,071,424 | A | 1/1978 | Dart et al. |
| 4,284,574 | A | 8/1981 | Bagga |
| 5,356,951 | A | 10/1994 | Yearn et al. |
| 5,391,650 | A | 2/1995 | Brennan et al. |
| 5,411,847 | A | 5/1995 | Leppard et al. |
| 5,679,710 | A | 10/1997 | Davy et al. |

FOREIGN PATENT DOCUMENTS

| | | |
|---|---|---|
| EP | 1 057 808 A2 | 12/2000 |
| GB | 1 336 512 | 11/1973 |
| JP | 48-013313 A | 2/1973 |
| JP | 48-49875 A | 7/1973 |
| JP | 61-194401 A | 8/1986 |
| JP | 61-286346 A | 12/1986 |
| JP | 63-186716 A | 8/1988 |
| JP | 63-207632 A | 8/1988 |
| JP | 63-248811 A | 10/1988 |
| JP | 63-248814 A | 10/1988 |
| JP | 04-180911 A | 6/1992 |
| JP | 05-194135 A | 8/1993 |
| JP | 06-172299 A | 6/1994 |
| JP | 08-157320 A | 6/1996 |
| JP | 08-208417 A | 8/1996 |
| WO | WO2005/107626 | * 11/2005 |
| WO | WO 2005/107626 A1 | 11/2005 |

OTHER PUBLICATIONS

Young-Wook Song et al, "Cure Mechanism of DGEBA/MDA/HQ-PGE System", Database CA [Online] Chemical Abstracts Service, Columbus, Ohio, XP002395088, retrieved from STN Database Accession No. 1996:282661.

Zbigniew Brzozowski et al., "Manufacture on New Allyl-Functional Phenoxy-Capped Bisphenol A bis(2-hydroxypropyl) Ethers", Database CA [Online] Chemical Abstracts Service, Columbus, Ohio, XP002395089, retrieved from STN Database Accession No. 1999:202141.

Sylvie Jost et al., "Reaction of bisPhenol-A Diglycidyl Ether with Substituted Phenols" Organic Preparations and Procedures Int., 1999, pp. 193-200, vol. 31, No. 2, Organic Preparations and Procedures, Inc.

* cited by examiner

*Primary Examiner*—Shailendra Kumar
*Assistant Examiner*—Yevegeny Valenrod
(74) *Attorney, Agent, or Firm*—Buchanan Ingersoll & Rooney PC

(57) ABSTRACT

A (meth)acrylic ester compound represented by the general formula (1) and a dental material containing the compound, $$R_{13}-O-CH_2CCH_2-X_{11}-R_{11}-X_{11}-CH_2CCH_2-O-R_{13} \quad (1)$$

with $R_{12}$ substituents and $R_{14}$-C(=O)-O- ester groups wherein, in the formula, $R_{11}$ represents a divalent aromatic group; $R_{12}$ represents a hydrogen atom or a methyl group; $R_{13}$ represents an aryl group; $R_{14}$ represents a hydrogen atom or a methyl group; and $X_{11}$, represents an oxygen atom or a sulfur atom. A polymerizable composition containing the (meth)acrylic ester compound and an optical part obtained by polymerizing the polymerizable composition are also provided. The cured composition can provide advantageous physical and optical properties.

18 Claims, 1 Drawing Sheet

(METH) ACRYLIC ESTER COMPOUND AND USE THEREOF

TECHNICAL FIELD

The present invention relates to (meth)acrylic ester compounds which are useful for dental materials, optical parts and the like, polymerizable compositions containing the (meth) acrylic ester compounds, and the use for the dental materials, the optical parts and the like using the polymerizable compositions.

More specifically, the present invention relates to a dental material and a dental composition which are excellent in curability (particularly, photocurability) of the composition itself, have high transparency and X-ray contrast property, and small polymerization shrinkage.

BACKGROUND ART

Dental materials containing polymerizable compounds such as a (meth)acrylic ester compound and the like have been widely used in the field of dental treatment from the advantages of excellent operability, aesthetic property, strength and the like. In particular, visible light polymerization type dental compositions have been used in many cases because they are capable of using visible light which is safe to living body and they have the aforementioned advantages (Patent Document 1).

As fillers contained in the dental compositions for composite resins, hard resins, artificial teeth or the like, powdery inorganic components such as silica, glass and the like are used for the purposes of imparting the mechanical strength to the compositions and improving various properties of a resin matrix from the past.

In the dental treatment, the condition of the treatment is often confirmed by X-ray photography, so that as a powdery inorganic component contained in the dental compositions, a powder (a pulverized glass powder) obtained by pulverizing a glass containing a heavy metal element having X-ray contrast property, such as barium, zirconium, strontium or the like, has been heretofore used such that X-ray photography should be feasible in the dental treatment. The pulverized glass powder is generally prepared by, for example, pulverizing such a glass as mentioned above. In the conventional technique for glass pulverization, however, it was difficult to finely pulverize a glass, and a glass powder having a particle diameter of around 10 μm to several tens of μm (20 to 30 μm) has been usually employed. If a dental composition containing a glass powder having such a large particle diameter was used, it was very difficult to form a machined surface having polish clinically similar to that of natural teeth.

In order to solve the aforementioned problems associated with incorporation of such a glass powder, composite resins mainly using a finely pulverized glass powder having an average particle diameter of not more than 2 μm have been recently developed. For example, an invention using a pulverized glass powder having an average particle diameter of from 0.1 to 5 μm and/or an inorganic compound having an average particle diameter of from 0.01 to 0.04 μm, such as silica fine particles or the like, is disclosed (Patent Document 2).

The composite resin using the finely pulverized glass powder is improved in the surface polish that has been considered as a disadvantage of a composite resin using a conventional pulverized glass powder having a relatively larger particle diameter, but the dental composition containing such a finely pulverized glass powder still has many disadvantages to be improved, with regard to the balance of properties such as transparency, photocurability, X-ray contrast property and the like. Namely, for example, in case of a dental composition wherein a finely pulverized filler having an average particle diameter of not more than 2 μm is homogeneously contained, the boundary area between the filler and the resin matrix (cured resin product) is markedly increased, and in order to ensure its transparency, refractive indices of the filler and the resin matrix need to be approximated to each other. However, if the content of the heavy metal element in the filler is increased to ensure high X-ray contrast property, the refractive index of the filler becomes high. The refractive index of the resin matrix such as epoxy methacrylate (hereinafter referred to as Bis-GMA for short) to be derived from 2,2-bis (4-hydoroxyphenyl)propane (usually called bisphenol A) that has been heretofore applied to dental use is at most about 1.55, and by approximating the refractive index of the filler to the aforementioned value, the transparency of the dental composition has been ensured. However, fillers having high X-ray contrast property and suitable polymerizable compounds imparting a cured resin product having high refractive index have been in demand, some of which have been proposed (Patent Documents 3 to 4).

As described above, with regard to the transparency of teeth, extremely high transparency in the appearance is often required for the composite resin or the hard resin used for the front tooth broken edge or the like. In such a part, the light transmittance at the wavelength of 480 nm that is a wavelength of a light from a dental irradiator needs to be not less than 5% in many cases. On the other hand, in the dentin portion or the like, the transparency of the dental resin or the hard resin may be relatively low because such a part is free from such problems in the appearance, and it is possible to use even a dental resin or a hard resin having a transparency of not more than 1%. In order to control color tone of the teeth, however, a pigment such as titanium oxide, bengala or the like is combined, so that even the dentin is desired to have high transparency to enhance the degree of freedom of coloring. In case of a dental material of a photopolymerization type, there is an advantage that higher transparency brings about larger curing depth and higher conversion, and as a result, the mechanical properties are enhanced.

The light transmittance of a dental composition containing no pigment is preferably not less than 0.05%, more preferably not less than 1%, and in the practical use, the light transmittance is particularly preferably not less than 5%. The X-ray contrast property value of such a material commercially available at present is at most about 200 to 300% based on aluminum, so that it is feasible to distinguish such a material from the tooth enamel (X-ray contrast property value of about 180% based on aluminum) by X-rays in the usual filling treatment. In case of filling in a small amount or thin filling, however, it becomes difficult to clearly distinguish such a material from the tooth enamel.

Furthermore, as a method for decreasing polymerization shrinkage that is a clinically serious problem in the dental material, use of a dental composition mixed with a composite filler obtained by pulverizing a cured product obtained by curing a mixture of an inorganic filler and a polymerizable composition in advance is known. Although the dental composition can achieve a decrease in the polymerization shrinkage, refractive indices of the inorganic filler, a resin matrix of the composite filler and a resin matrix of the dental composition need to be finely suited to each other in order to ensure the transparency in case of the aforementioned composite filler.

Under these circumstances, in recent years, such dental materials and dental compositions having high X-ray contrast property and transparency, and at the same time, small polymerization shrinkage, and satisfying various properties (for example, mechanical strength, water absorption and the like) required for dental materials have been in demand. Also, new polymerizable compounds capable of realizing these materials have been demanded.

Patent Document 1: JP1973-49875A
Patent Document 2: JP1993-194135A
Patent Document 3: JP1996-157320A
Patent Document 4: JP1996-208417A On the other hand, an inorganic glass has been used in a broad range of fields as a transparent optical material because it is excellent in the transparency and various properties such as small optical anisotropy or the like. However, such an inorganic glass has drawbacks in that it is heavy and easily broken, and it has bad productivity in processing for the production of optical parts or the like. As a result, a transparent organic polymer material (optical resin) has been under development with eagerness as a material for replacing the inorganic glass. Recently, high functionality and high quality in optical resins have been promoted. Optical parts obtained by molding and processing these optical resins have further come into wide use, for example, in lens fields such as a spectacle lens for vision correction, a pickup lens in optical information recording devices such as CD, DVD and the like, a plastic lens for cameras such as a digital camera and the like, and a Fresnel lens for use in a liquid crystal projector or a projector television.

One of the most important and fundamental properties as an optical resin is transparency. Up to now, as an optical resin having excellent transparency, there have been known resins, for example, polymethyl methacrylate (PMMA), polycarbonate (BPA-PC), polystyrene (PS), methyl methacrylate-styrene copolymer (MS), styrene-acrylonitrile copolymer (SAN), poly (4-methyl-1-pentene) (TPX), polycycloolefin (COP), diethylene glycol bisallylcarbonate polymer (DAC); polythiourethane (PTU), and the like.

Among these optical resins, polymethyl methacrylate (PMMA) is widely used as one of representative optical resins as it is superior in its transparency and has characteristics such that optical anisotropy is low (low double refractive index), and moldability and weather resistance are good, and the like. However, there are drawbacks in that its refractive index (nd) is low, i.e., 1.49, the water absorption coefficient is high, and the like.

In the same manner, polycarbonate (BPA-PC), one of the representative optical resins, can be obtained by the polycondensation reaction of 2,2-bis(4-hydroxyphenyl)propane (hereinafter referred to as bisphenol A what is commonly called) and a carbonate compound (for example, carbonyl chloride, diphenylcarbonate or the like), having characteristics such that the transparency, heat resistance and impact resistance are excellent, and the refractive index (nd=1.59) is relatively high. As a result, it is widely used for optical purposes including an optical disk plate for information recording. However, it has drawbacks in that the chromatic aberration (dispersion of refractive index) and double refractive index are relatively high, and melting viscosity is high, thus lowering moldability a little. Needless to say, improvement of new performance and characteristics is being made to overcome these drawbacks.

Diethylene glycol bisallylcarbonate polymer (DAC) is a thermosetting resin of a crosslinked high molecular structure to be obtained by casting radical polymerization of a monomer, i.e., diethylene glycol bisallylcarbonate. It has characteristics such that the transparency and heat resistance are excellent, and the chromatic aberration is low. Due to such characteristics, it is used the most for a general-purpose plastic spectacle lens for vision correction. However, there are drawbacks in that its refractive index is low (nd=1.50) and its impact resistance is a little inferior.

Polythiourethane (PTU) is a thermosetting resin of a crosslinked polymer structure to be obtained by the reaction between a diisocyanate compound and a polythiol compound. It is an extremely excellent optical resin having characteristics such that the transparency and impact resistance are excellent, the refractive index is high (nd≧1.6), and the chromatic aberration is relatively low. At present, it is used the most for the purpose of a high-quality plastic spectacle lens for vision correction in which the thickness is thin and the weight is light. However, there is room for further improvement only from the viewpoint of the productivity requiring long time (1 to 3 days) for thermal polymerization molding in the production process of spectacle lenses.

In order to solve these problems and to produce optical parts such as optical lenses and the like with high productivity, there has been proposed or suggested a method of polymerizing and molding a compound having radical polymerization ability (hereinafter referred to as a polymerizable compound) for obtaining an aiming molded product within a short period of time in the presence of a compound (photopolymerization initiator) for initiating radical polymerization by an irradiation with a light such as ultraviolet rays and the like (Patent Documents 5 to 8 and the like).

As a representative example of the polymerizable compound used for the photopolymerization, a (meth)acrylic ester compound is used. However, there has been proposed a (meth)acrylic ester compound, a (meth)acrylic (thio)ester compound or the like having a specific structure containing a bromine atom or a sulfur atom in order to obtain much higher refractive index and Abbe number. According to these methods, such a polymerizable compound can be polymerized within a short period of time. However, considering the balance of general properties such as transparency, optical properties (for example, refractive index, Abbe number or the like), thermal properties (for example, heat distortion temperature or the like), mechanical properties (for example, impact resistance, flexural strength or the like) and the like, it is difficult to mention that the thus-obtained cured product (resin) is sufficiently satisfying as an optical part.

Conventionally known optical resins have excellent characteristics as described above, but, according to the present state, each of them has also drawbacks to overcome. Under these circumstances, it is required to develop optical resins such that they can be polymerized and molded within a short period of time by photopolymerization, in which the transparency and optical properties (high refractive index and Abbe number) of the thus-obtained cured product or optical part are excellent, and thermal properties, mechanical properties and the like are good.

Patent Document 5: JP1992-180911A
Patent Document 6: JP1988-248811A
Patent Document 7: JP1988-207632A
Patent Document 8: JP1986-194401A An object of the present invention is to solve the above problems in a dental material and a dental composition. That is, the present invention is to provide a dental material and a dental composition which satisfy the requirements for dental materials and dental compositions, which have excellent curability and well-balanced excellent transparency and excellent X-ray contrast property though the transparency and the X-ray contrast property are hardly compatible with each other, and have small polymerization shrinkage, and a polymerizable compound capable of realizing such a dental material or a dental composition.

Furthermore, another object of the present invention is to provide an optical resin which can solve the above problems associated with optical resins for use in optical parts, more specifically, a polymerizable composition which can be polymerized and molded within a short period of time by photopolymerization and imparts a cured resin product having excellent transparency, optical properties (refractive index and Abbe number), heat resistance, mechanical properties, weather resistance and the like, and an optical part obtained by polymerizing the above polymerizable composition.

DISCLOSURE OF THE INVENTION

In order to solve the above objects, the present inventors have conducted an extensive study, and as a result, they have found that a dental material and a dental composition which each contains a compound represented by the general formula (1) are excellent in curability and also combine transparency, X-ray contrast property, and low polymerization shrinkage while retaining various properties required for dental materials (for example, flexural strength and the like). Furthermore, a polymerizable composition containing the compound represented by the general formula (1) can be polymerized and molded within a short period of time by photopolymerization and it gives a cured resin product satisfactory in the transparency, optical properties (refractive index and Abbe's number), heat resistance, mechanical properties, weather resistance and the like. Thus, the present invention has been completed. That is, the present invention relates to:

1. A (meth)acrylic ester compound represented by the general formula (1),

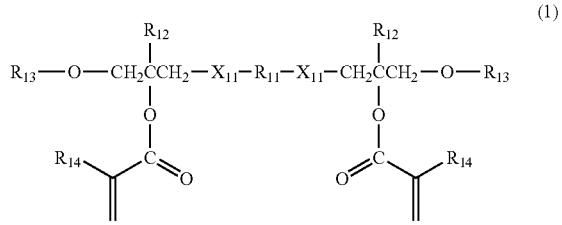

wherein, in the formula, $R_{11}$ represents a divalent aromatic group; $R_{12}$ represents a hydrogen atom or a methyl group; $R_{13}$ represents an aryl group; $R_{14}$ represents a hydrogen atom or a methyl group; and $X_{11}$ represents an oxygen atom or a sulfur atom;

2. The (meth)acrylic ester compound, wherein the $R_{11}$ group in the general formula (1) is a group represented by any one of the formulae (2) to (4),

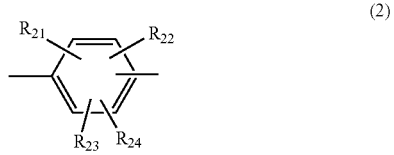

wherein, in the formula (2), $R_{21}$, $R_{22}$, $R_{23}$ and $R_{24}$ are each independently a hydrogen atom, an alkyl group, an alkoxy group or a nitro group,

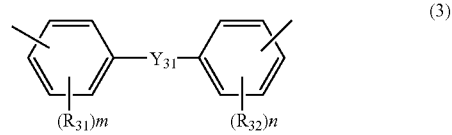

wherein, in the formula (3), $R_{31}$ and $R_{32}$ are each independently an alkyl group, an alkenyl group, an aralkyl group, an aryl group, an alkoxy group or a nitro group; and $Y_{31}$ represents a single bond, —$C(R_{33})_2$— group, —O— group, —S— group, —$SO_2$— group, a group represented by the formula (3-a) or a group represented by the formula (3-b),

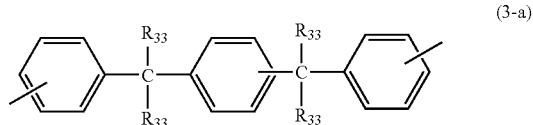

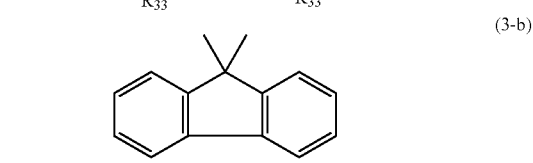

wherein, in the above groups, $R_{33}$s are each independently a hydrogen atom, an alkyl group or an aryl group; and m and n are each independently 0 or an integer of 1 to 4,

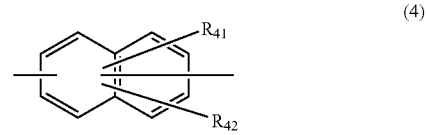

wherein, in the formula (4), $R_{41}$ and $R_{42}$ are each independently a hydrogen atom or an alkyl group;

3. A polymerizable composition containing the compound represented by the general formula (1) as described in item 1 or 2;

4. A cured product obtained by polymerizing the polymerizable composition as described in item 3;

5. A dental material containing a compound represented by the general formula (1),

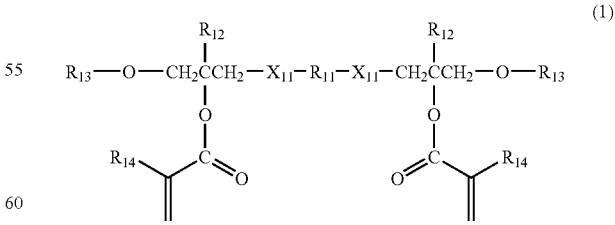

wherein, in the formula, $R_{11}$ represents a divalent aromatic group; $R_{12}$ represents a hydrogen atom or a methyl group; $R_{13}$ represents an aryl group; $R_{14}$ represents a hydrogen atom or a methyl group; and $X_{11}$ represents an oxygen atom or a sulfur atom;

6. The dental material as described in item 5, wherein the $R_{11}$ group in the compound represented by the general formula (1) is a group represented by any one of the formulae (2) to (4),

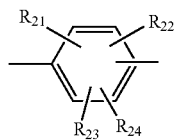
(2)

wherein, in the formula (2), $R_{21}$, $R_{22}$, $R_{23}$ and $R_{24}$ are each independently a hydrogen atom, an alkyl group, an alkoxy group or a nitro group,

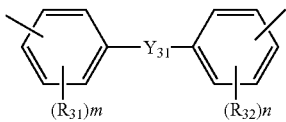
(3)

wherein, in the formula (3), $R_{31}$ and $R_{32}$ are each independently an alkyl group, an alkenyl group, an aralkyl group, an aryl group, an alkoxy group or a nitro group; and $Y_{31}$ represents a single bond, —$C(R_{33})_2$— group, —O— group, —S— group, —$SO_2$— group, a group represented by the formula (3-a) or a group represented by the formula (3-b),

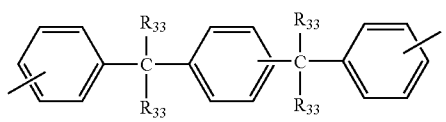
(3-a)

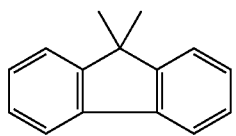
(3-b)

wherein, in the above groups, $R_{33}$s are each independently a hydrogen atom, an alkyl group or an aryl group; and m and n are each independently 0 or an integer of 1 to 4,

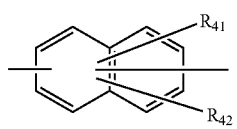
(4)

wherein, in the formula (4), $R_{41}$ and $R_{42}$ are each independently a hydrogen atom or an alkyl group;

7. A dental composition containing (A) a polymerizable compound and (B) a polymerization initiator, wherein the polymerizable compound is the compound represented by the general formula (1) as described in item 1 or 2;

8. The dental composition as described in item 7, wherein the dental composition further contains (C) a filler;

9. The dental composition as described in item 7 or 8, wherein the dental composition further contains other polymerizable compounds in addition to the compound represented by the general formula (1);

10. The dental composition as described in any one of items 7 to 9, wherein the refractive index of the cured product after polymerization is not less than 1.55;

11. An optical part comprising the cured product as described in item 4;

12. A hydroxy compound represented by the general formula (5),

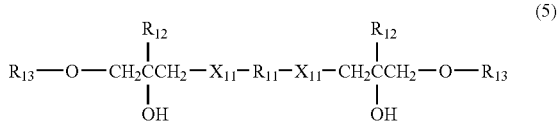
(5)

wherein, in the formula, $R_{11}$ represents a divalent aromatic group; $R_{12}$ represents a hydrogen atom or a methyl group; $R_{13}$ represents an aryl group; and $X_{11}$ represents an oxygen atom or a sulfur atom;

13. The hydroxy compound as described in item 12, wherein the $R_{11}$ group in the compound represented by the general formula (5) is a group represented by any one of the above formulae (2) to (4);

14. An ester compound represented by the general formula (6),

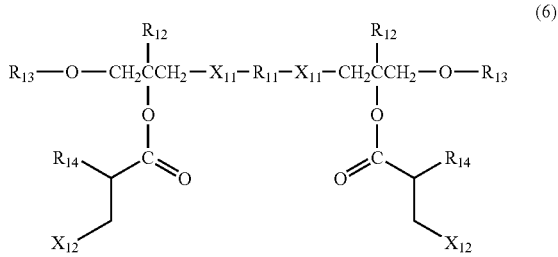
(6)

wherein, in the formula, $R_{11}$ represents a divalent aromatic group; $R_{12}$ represents a hydrogen atom or a methyl group; $R_{13}$ represents an aryl group; $R_{14}$ represents a hydrogen atom or a methyl group; $X_{11}$ represents an oxygen atom or a sulfur atom; and $X_{12}$ represents a halogen atom; and 15. The ester compound as described in item 14, wherein the $R_{11}$ group in the compound represented by the general formula (6) is a group represented by any one of the above formulae (2) to (4).

The (meth)acrylic ester compound represented by the general formula (1) of the present invention is widely used as a polymerizable compound for a dental material and a dental composition along with a polymerization initiator, a filler and the like.

The dental composition comprising a (meth)acrylic ester compound represented by the general formula (1), a polymerization initiator, and, as needed, a filler, of the present invention, satisfies the requirements such as mechanical strength, abrasion resistance, water resistance and the like, and provides a cured product in which X-ray contrast property, transparency and curability (particularly, photocurability) are excellent, and polymerization shrinkage is small.

The dental composition of the present invention has more excellent X-ray contrast property than conventional products so that it is possible to conduct the dental treatment while confirming a portion of its application.

Furthermore, the polymerizable composition containing the (meth)acrylic ester compound represented by the general formula (1) of the present invention can be polymerized, cured, and molded within a short period of time by photopolymerization, so that the productivity in the polymerization and molding processes is high.

The cured product and the optical part according to the present invention are superior in the transparency and optical properties (high refractive index), and also combine thermal properties, mechanical properties and weather resistance.

BEST MODE FOR CARRYING OUT THE INVENTION

Figure 1:
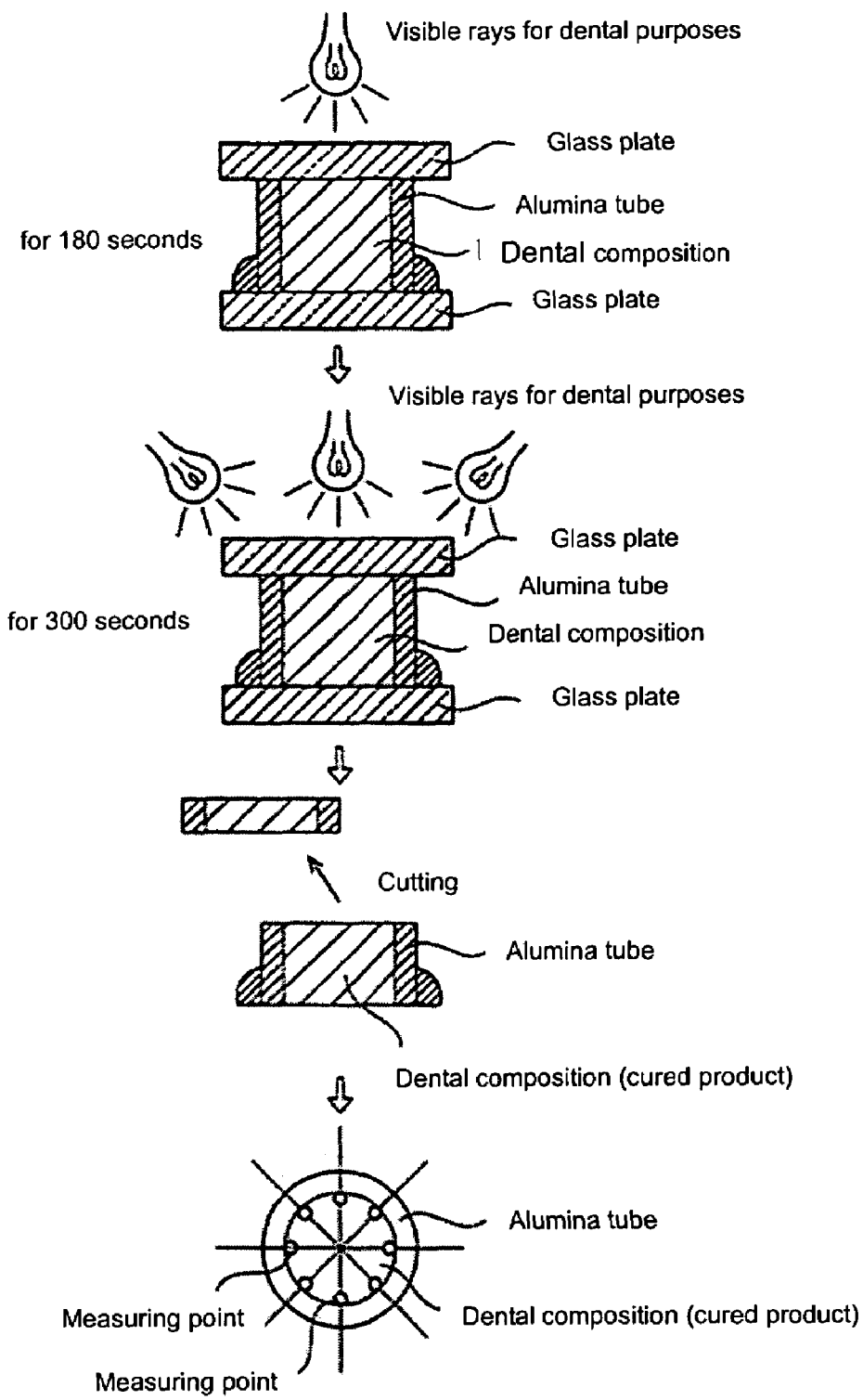
FIG. 1 is a view illustrating a method for measuring polymerization shrinkage in a dental composition.

The present invention will be described in more detail below.

First, the (meth)acrylic ester compound represented by the general formula (1) according to the present invention is described hereinafter.

The (meth)acrylic ester compound represented by the general formula (1) is a new (meth)acrylic ester compound partially having a plurality of aromatic ring structures such as a benzene ring, a biphenyl ring, a naphthalene ring or the like in a molecule,

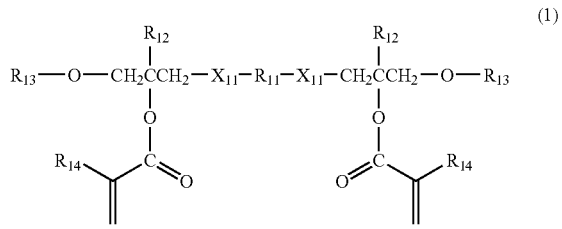
(1)

wherein, in the formula, $R_{11}$ represents a divalent aromatic group; $R_{12}$ represents a hydrogen atom or a methyl group; $R_{13}$ represents an aryl group; $R_{14}$ represents a hydrogen atom or a methyl group; and $X_{11}$ represents an oxygen atom or a sulfur atom.

In the compound represented by the general formula (1), $R_{11}$ represents a divalent aromatic group.

As for the above $R_{11}$ group, a divalent aromatic group may be good. Such a group is not particularly restricted thereto, but it is preferably a divalent aromatic group of 5 to 30 carbon atoms which may be unsubstituted or substituted, and more preferably a phenylene group, a naphthalene group or a divalent bisphenol residue derived from a bisphenol compound which may be unsubstituted or substituted.

The $R_{11}$ group is more preferably a group represented by the formulae (2) to (4),

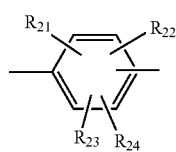
(2)

wherein, in the formula (2), $R_{21}$, $R_{22}$, $R_{23}$ and $R_{24}$ are each independently a hydrogen atom, an alkyl group, an alkoxy group or a nitro group,

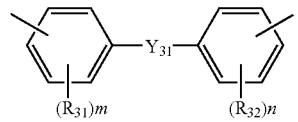
(3)

wherein, in the formula (3), $R_{31}$ and $R_{32}$ are each independently an alkyl group, an alkenyl group, an aralkyl group, an aryl group, an alkoxy group or a nitro group; and $Y_{31}$ represents a single bond, —$C(R_{33})_2$— group, —O— group, —S— group, —$SO_2$— group, a group represented by the formula (3-a) or a group represented by the formula (3-b),

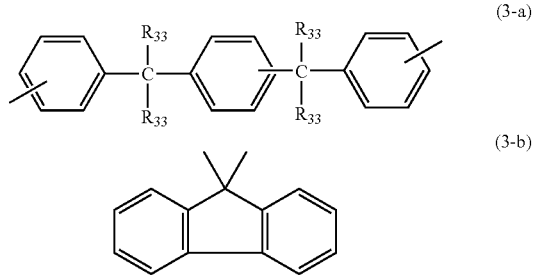
(3-a)

(3-b)

wherein, in the above groups, $R_{33}$s are each independently a hydrogen atom, an alkyl group or an aryl group; and m and n are each independently 0 or an integer of 1 to 4,

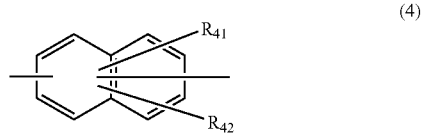
(4)

wherein, in the formula (4), $R_{41}$ and $R_{42}$ are each independently a hydrogen atom or an alkyl group.

In the formula (2) representing the $R_{11}$ group, $R_{21}$, $R_{22}$, $R_{23}$ and $R_{24}$ are each independently a hydrogen atom, an alkyl group, an alkoxy group or a nitro group.

The alkyl group is a straight-chain, branched or cyclic alkyl group which may have a substituent, and preferably a straight-chain, branched or cyclic alkyl group of 1 to 20 carbon atoms; which may have a substituent.

The alkoxy group is a straight-chain, branched or cyclic alkoxy group which may have a substituent, and preferably a straight-chain, branched or cyclic alkoxy group of 1 to 20 carbon atoms, which may have a substituent.

In the formula (2), $R_{21}$, $R_{22}$, $R_{23}$ and $R_{24}$ are each preferably a hydrogen atom, an unsubstituted straight-chain, branched or cyclic alkyl group of 1 to 10 carbon atoms, an unsubstituted straight-chain, branched or cyclic alkoxyl group of 1 to 10 carbon atoms or a nitro group, more preferably a hydrogen atom, a methyl group, an ethyl group, an n-propyl group, an isopropyl group, an n-butyl group, an isobutyl group, a tert-butyl group, a methoxy group, an ethoxy group, an n-propoxy group, an isopropoxy group, an n-butoxy group, an isobutoxy group, a tert-butoxy group or a nitro group, and further preferably a hydrogen atom, a methyl group or a methoxy group.

As for the aforementioned substituents of $R_{21}$, $R_{22}$, $R_{23}$ and $R_{24}$, a hydrogen atom is particularly preferable.

In the compound represented by the general formula (1), when $R_{11}$ is a group represented by the formula (2), there are three modes as bonding modes between the benzene ring $R_{11}$ and the two $X_{11}$ groups bonded to the benzene ring, namely, bonding at the para-positions, the meta-positions and the ortho-positions to $R_{11}$. Preferable is a compound having a structure wherein the XI, groups are bonded at the para-positions or the meta-positions, and more preferably at the meta-positions.

In the formula (3) representing the $R_{11}$ group, $R_{31}$ and $R_{32}$ are each independently an alkyl group, an alkenyl group, an aralkyl group, an aryl group, an alkoxy group or a nitro group.

The alkyl group is a straight-chain, branched or cyclic alkyl group which may have a substituent, and preferably a straight-chain, branched or cyclic alkyl group of 1 to 20 carbon atoms, which may have a substituent.

The alkenyl group is a straight-chain, branched or cyclic alkenyl group which may have a substituent, and preferably a straight-chain, branched or cyclic alkenyl group of 2 to 20 carbon atoms, which may have a substituent.

The aralkyl group is an aralkyl group of 6 to 20 carbon atoms, and preferably an aralkyl group of 6 to 12 carbon atoms, which may have a substituent.

The aryl group is an aryl group of 6 to 20 carbon atoms, and preferably an aryl group of 6 to 10 carbon atoms, which may have a substituent.

The alkoxy group is a straight-chain, branched or cyclic alkoxy group which may have a substituent, and preferably a straight-chain, branched or cyclic alkoxy group of 1 to 20 carbon atoms, which may have a substituent.

In the formula (3), $R_{31}$ and $R_{32}$ are preferably a hydrogen atom, an unsubstituted straight-chain, branched or cyclic alkyl group of 1 to 10 carbon atoms, an unsubstituted straight-chain, branched or cyclic alkenyl group of 2 to 10 carbon atoms, an unsubstituted aralkyl group of 6 to 12 carbon atoms, an unsubstituted aryl group of 6 to 10 carbon atoms, an unsubstituted straight-chain, branched or cyclic alkoxy group of 1 to 10 carbon atoms or a nitro group, more preferably a hydrogen atom, a methyl group, an ethyl group, an n-propyl group, an isopropyl group, an n-butyl group, an isobutyl group, a tert-butyl group, a 2-allyl group, a benzyl group, a phenyl group, a methoxy group, an ethoxy group, an n-propoxy group, an isopropoxy group, an n-butoxy group, an isobutoxy group, a tert-butoxy group or a nitro group, and further preferably a hydrogen atom, a methyl group or a methoxy group.

As for the aforementioned substituents of $R_{31}$ and $R_{32}$, a hydrogen atom is particularly preferable.

In the formula (3) representing the $R_{11}$ group, $Y_{31}$ represents a single bond, —C($R_{33}$)$_2$— group, —O— group, —S— group, —SO$_2$— group, a group represented by the formula (3-a) or a group represented by the formula (3-b).

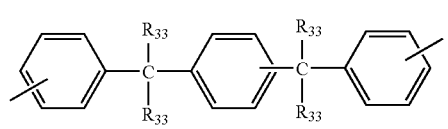

(3-a)

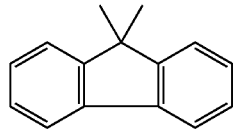

(3-b)

In these groups, $R_{33}$s are each independently a hydrogen atom, an alkyl group or an aryl group, and more preferably a methyl group or a phenyl group.

The above $Y_{31}$ is preferably a single bond, —C($R_3$)$_2$— group, —SO$_2$— group or a group represented by the formula (3-a) or a group represented by the formula (3-b), and more preferably a single bond, —C($R_3$)$_2$— group, —SO$_2$— group or a group represented by the formula (3-a-1) or a group represented by the formula (3-b).

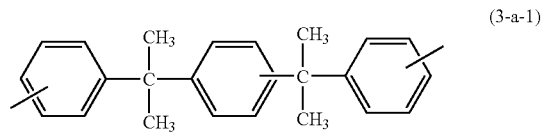

(3-a-1)

In the formula (3) representing the $R_{11}$ group, m and n are each independently 0 or an integer of 1 to 4, preferably an integer of 0 to 2, and more preferably an integer of 0.

In the compound represented by the general formula (1), when $R_{11}$ is a group represented by the formula (3), there are three modes as bonding modes between the $X_{11}$ groups and the two aromatic rings in the $Y_{31}$ group, namely, each independently bonding at the para-positions, the meta-positions and the ortho-positions. Preferable is a compound having a structure wherein the XI, groups are bonded at the para-positions or the ortho-positions, and more preferably at the para-positions.

In the formula (4) representing the $R_{11}$ group, $R_{41}$ and $R_{42}$ are each independently a hydrogen atom or an alkyl group.

The alkyl group is a straight-chain, branched or cyclic alkyl group which may have a substituent, and preferably a straight-chain, branched or cyclic alkyl group of 1 to 20 carbon atoms, which may have a substituent.

In the formula (4), $R_{41}$ and $R_{42}$ are preferably a hydrogen atom or an unsubstituted straight-chain, branched or cyclic alkyl group of 1 to 10 carbon atoms, more preferably a hydrogen atom, a methyl group, an ethyl group, an n-propyl group, an isopropyl group, an n-butyl group, an isobutyl group or a tert-butyl group, and further preferably a hydrogen atom or a methyl group.

As for the aforementioned substituents of $R_{41}$ and $R_{42}$, a hydrogen atom is particularly preferable.

In the compound represented by the general formula (1), when $R_{11}$ is a group represented by the formula (4), there are several modes as bonding modes between the naphthalene ring $R_{11}$ group and the two $X_{11}$ groups bonded to the naphthalene ring, namely, bonding at the 1,4-positions, the 1,5-positions, the 1,8-positions, the 2,6-positions and the 2,7-positions to $R_{11}$. Preferable is a compound having a structure wherein the $X_{11}$ groups are bonded at the 1,5-positions, the 2,6-positions or the 2,7-positions, and more preferably at the 2,6-positions or the 2,7-positions.

In the compound represented by the general formula (1), $R_{12}$ represents a hydrogen atom or a methyl group.

In the compound represented by the general formula (1), $R_{13}$ represents an aryl group. The $R_{13}$ group is preferably an aryl group of 5 to 20 carbon atoms.

The aromatic ring in the $R_{13}$ group may have a substituent, but it preferably comprises only an aromatic ring structure in order to obtain maximum desired effect. The substituent is preferably a substituent having an aromatic ring structure such as an aralkyl group, an aralkyloxy group, an aryloxy group or the like.

Concrete examples of the substituent $R_{13}$ include a phenyl group, a 4-phenylphenyl group, a 3-phenylphenyl group, a 2-phenylphenyl group, a 1-naphthyl group, a 2-naphthyl group, a 4-phenoxyphenyl group, a 3-phenoxyphenyl group, a 2-phenoxyphenyl group and the like. As the $R_{13}$ group in the general formula (1), a phenyl group, a 4-phenylphenyl group, a 3-phenylphenyl group, a 2-phenylphenyl group, a 1-naphthyl group, and a 2-naphthyl group are particularly preferable.

In the compound represented by the general formula (1), $R_{14}$ represents a hydrogen atom or a methyl group. In the compound represented by the general formula (1), $X_{11}$ represents an oxygen atom or a sulfur atom, and preferably an oxygen atom.

As preferred embodiments of the (meth)acrylic ester compound represented by the general formula (1), (meth)acrylic ester compounds represented by the following general formulae (1-A) to (1-I) can be cited.

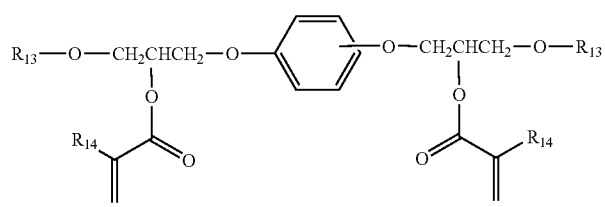

(1-A)

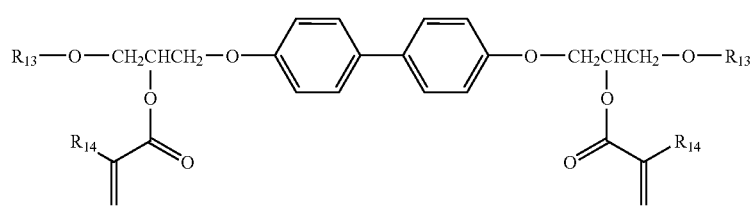

(1-B)

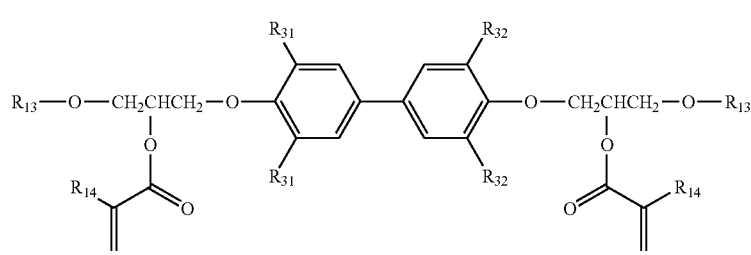

(1-C)

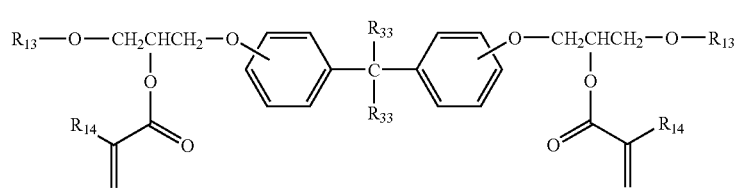

(1-D)

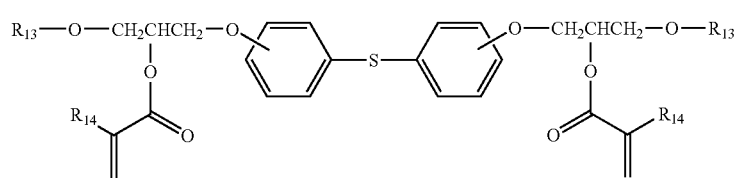

(1-E)

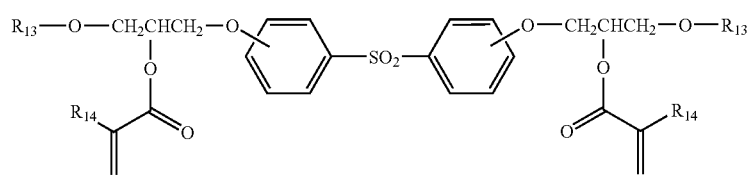

(1-F)

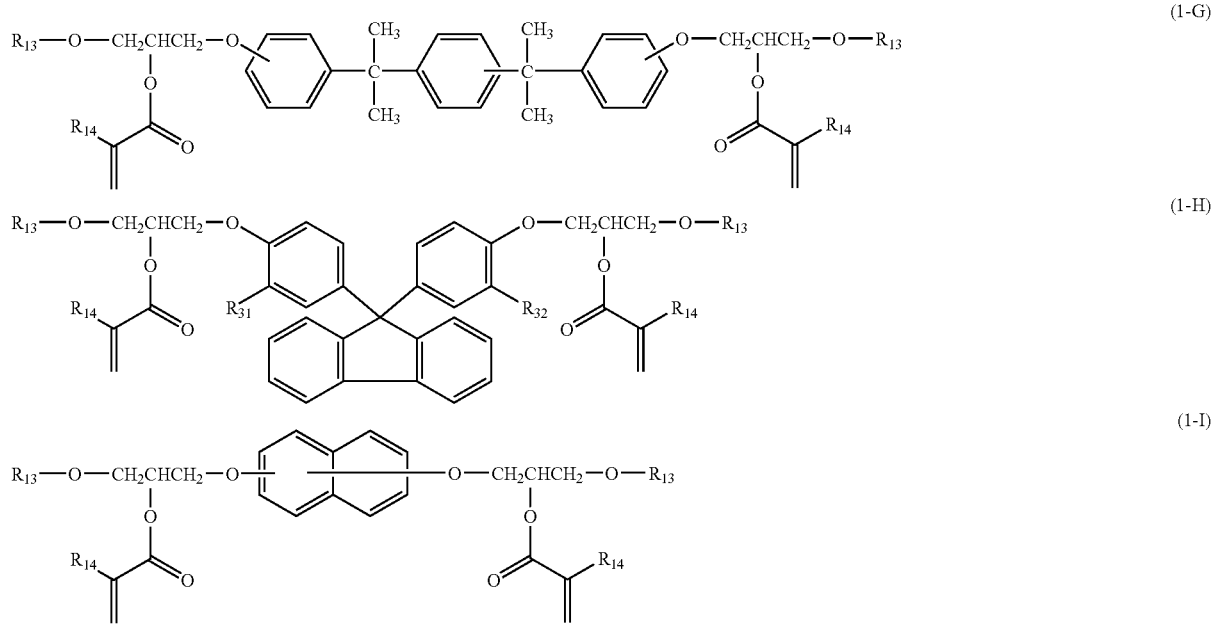

wherein, in the above general formulae (1-A) to (1-H), $R_{13}$, $R_{14}$, $R_{31}$, $R_{32}$ and $R_{33}$ represent the same as those described before.

Concrete examples of the (meth)acrylic ester compound represented by the general formula (1) include, though not restricted to, 1,2-bis[3-(4-phenylphenyloxy)-2-acryloyloxypropyloxy]benzene, 1,2-bis[3-(3-phenylphenyloxy)-2-acryloyloxypropyloxy]benzene, 1,2-bis[3-(2-phenylphenyloxy)-2-acryloyloxypropyloxy]benzene, 1,2-bis[3-(1-naphthyloxy)-2-acryloyloxypropyloxy]benzene, 1,2-bis[3-(2-naphthyloxy)-2-acryloyloxypropyloxy]benzene, 1,2-bis[3-(4-phenylphenyloxy)-2-methacryloyloxypropyloxy]benzene, 1,2-bis[3-(3-phenylphenyloxy)-2-methacryloyloxypropyloxy]benzene, 1,2-bis[3-(2-phenylphenyloxy)-2-methacryloyloxypropyloxy]benzene, 1,2-bis[3-(1-naphthyloxy)-2-methacryloyloxypropyloxy]benzene, 1,2-bis[3-(2-naphthyloxy)-2-methacryloyloxypropyloxy]benzene, 1,3-bis[3-(4-phenylphenyloxy)-2-acryloyloxypropyloxy]benzene, 1,3-bis[3-(3-phenylphenyloxy)-2-acryloyloxypropyloxy]benzene, 1,3-bis[3-(2-phenylphenyloxy)-2-acryloyloxypropyloxy]benzene, 1,3-bis[3-(1-naphthyloxy)-2-acryloyloxypropyloxy]benzene, 1,3-bis[3-(2-naphthyloxy)-2-acryloyloxypropyloxy]benzene, 1,3-bis[3-(4-phenylphenyloxy)-2-methacryloyloxypropyloxy]benzene, 1,3-bis[3-(4-phenylphenyloxy)-2-methacryloyloxypropyloxy]benzene, 1,3-bis[3-(3-phenylphenyloxy)-2-methacryloyloxypropyloxy]benzene, 1,3-bis[3-(2-phenylphenyloxy)-2-methacryloyloxypropyloxy]benzene, 1,3-bis[3-(1-naphthyloxy)-2-methacryloyloxypropyloxy]benzene, 1,3-bis[3-(2-naphthyloxy)-2-methacryloyloxypropyloxy]benzene, 1,4-bis[3-(4-phenylphenyloxy)-2-acryloyloxypropyloxy]benzene, 1,4-bis[3-(3-phenylphenyloxy)-2-acryloyloxypropyloxy]benzene, 1,4-bis[3-(2-phenylphenyloxy)-2-acryloyloxypropyloxy]benzene, 1,4-bis[3-(1-naphthyloxy)-2-acryloyloxypropyloxy]benzene, 1,4-bis[3-(2-naphthyloxy)-2-acryloyloxypropyloxy]benzene, 1,4-bis[3-(4-phenylphenyloxy)-2-methacryloyloxypropyloxy]benzene, 1,4-bis[3-(3-phenylphenyloxy)-2-methacryloyloxypropyloxy]benzene, 1,4-bis[3-(2-phenylphenyloxy)-2-methacryloyloxypropyloxy]benzene, 1,4-bis[3-(1-naphthyloxy)-2-methacryloyloxypropyloxy]benzene, 1,4-bis[3-(2-naphthyloxy)-2-methacryloyloxypropyloxy]benzene, 1,2-bis[3-(4-phenylphenyloxy)-2-methacryloyloxypropyloxy]-3-methylbenzene, 1,2-bis[3-(2-phenylphenyloxy)-2-acryloyloxypropyloxy]-4-methylbenzene, 1,2-bis[3-(2-naphthyloxy)-2-methacryloyloxypropyloxy]-3-methoxybenzene, 1,2-bis[3-(4-phenylphenyloxy)-2-methacryloyloxypropyloxy]4-methoxybenzene, 1,2-bis[3-(2-phenylphenyloxy)-2-methacryloyloxypropyloxy]4-chlorobenzene, 1,2-bis[3-(1-naphthyloxy)-2-methacryloyloxypropyloxy]4-bromobenzene, 1,3-bis[3-(4-phenylphenyloxy)-2-acryloyloxypropyloxy]-2-methylbenzene, 1,3-bis[3-(2-naphthyloxy)-2-acryloyloxypropyloxy]-5-methylbenzene, 1,3-bis[3-(1-naphthyloxy)-2-methacryloyloxypropyloxy]-5-methoxybenzene, 1,3-bis[3-(2-phenylphenyloxy)-2-methacryloyloxypropyloxy]4-chlorobenzene, 1,4-bis[3-(4-phenylphenyloxy)-2-methacryloyloxypropyloxy]-2,6-dimethylbenzene, 4,4'-bis[3-(4-phenylphenyloxy)-2-acryloyloxypropyloxy]biphenyl, 4,4'-bis[3-(3-phenylphenyloxy)-2-acryloyloxypropyloxy]biphenyl, 4,4'-bis[3-(2-phenylphenyloxy)-2-acryloyloxypropyloxy]biphenyl, 4,4'-bis[3-(1-naphthyloxy)-2-acryloyloxypropyloxy]biphenyl, 4,4'-bis[3-(2-naphthyloxy)-2-acryloyloxypropyloxy]biphenyl, 4,4'-bis[3-(4-phenoxyphenyloxy)-2-acryloyloxypropyloxy]biphenyl, 4,4'-bis[3-(4-phenylphenyloxy)-2-methacryloyloxypropyloxy]biphenyl, 4,4'-bis[3-(3-phenylphenyloxy)-2-methacryloyloxypropyloxy]biphenyl, 4,4'-bis[3-(2-phenylphenyloxy)-2-methacryloyloxypropyloxy]biphenyl, 4,4'-bis[3-(1-naphthyloxy)-2-methacryloyloxypropyloxy]biphenyl, 4,4'-bis[3-(2-naphthyloxy)-2-methacryloyloxypropyloxy]biphenyl, 4,4'-bis[3-(4-phenoxyphenyloxy)-2-methacryloyloxypropyloxy]biphenyl, 3,3',5,5'-tetramethyl-4,4'-bis[3-(4-phenylphenyloxy)-2-acryloyloxypropyloxy]biphenyl, 3,3',5,5'-tetramethyl-4,4'-bis[3-(3-phenylphenyloxy)-2-acryloyloxypropyloxy]biphenyl, 3,3',5, 5'-tetramethyl-4,4'-bis[3-(2-phenylphenyloxy)-2-acryloyloxypropyloxy]biphenyl, 3,3',5,5'-tetramethyl-4,4'-bis[3-(1-naphthyloxy)-2-acryloyloxypropyloxy]biphenyl, 3,3',5,5'-tetramethyl-4,4'-bis[3-(2-naphthyloxy)-2-acryloyloxypropyloxy]biphenyl, 3,3',5,5'-tetramethyl-4,4'-bis[3-(4-phenoxyphenyloxy)-2-acryloyloxypropyloxy]biphenyl, 3,3',5,5'-tetramethyl4,4'-bis[3-(4-phenylphenyloxy)-2-methacryloyloxypropyloxy]biphenyl, 3,3',5,5'-tetramethyl4,4'-bis[3-(3-phenylphenyloxy)-2-methacryloyloxypropyloxy]biphenyl, 3,3',5,5'-tetramethyl4,4'-bis[3-(2-phenylphenyloxy)-2-methacryloyloxypropyloxy]biphenyl, 3,3',5,5'-tetramethyl-4,4'-bis[3-(1-naphthyloxy)-2-methacryloyloxypropyloxy]biphenyl, 3,3',5,5'-tetramethyl-4,4'-bis[3-(2-naphthyloxy)-2-methacryloyloxypropyloxy]biphenyl, 3,3',5,5'-tetramethyl-4,4'-bis[3-(4-phenoxyphenyloxy)-2-methacryloyloxypropyloxy]biphenyl, 2,4'-bis[3-(4-phenylphenyloxy)-2-acryloyloxypropyloxy]biphenyl, 2,4'-bis[3-(3-phenylphenyloxy)-2-acryloyloxypropyloxy]biphenyl, 2,4'-bis[3-(2-phenylphenyloxy)-2-acryloyloxypropyloxy]biphenyl, 2,4'-bis[3-(1-naphthyloxy)-2-acryloyloxypropyloxy]biphenyl, 2,4'-bis[3-(2-naphthyloxy)-2-acryloyloxypropyloxy]biphenyl, 2,4'-bis[3-(4-phenoxyphenyloxy)-2-acryloyloxypropyloxy]biphenyl, 2,4'-bis[3-(4-phenylphenyloxy)-2-methacryloyloxypropyloxy]biphenyl, 2,4'-bis[3-(3-phenylphenyloxy)-2-methacryloyloxypropyloxy]biphenyl, 2,4'-bis[3-(2-phenylphenyloxy)-2-methacryloyloxypropyloxy]biphenyl, 2,4'-bis[3-(1-naphthyloxy)-2-methacryloyloxypropyloxy]biphenyl, 2,4'-bis[3-(2-naphthyloxy)-2-methacryloyloxypropyloxy]biphenyl, 2,4'-bis[3-(4-phenoxyphenyloxy)-2-methacryloyloxypropyloxy]biphenyl, 2,2'-bis[3-(4-phenylphenyloxy)-2-acryloyloxypropyloxy]biphenyl, 2,2'-bis[3-(3-phenylphenyloxy)-2-acryloyloxypropyloxy]biphenyl, 2,2'-bis[3-(2-phenylphenyloxy)-2-acryloyloxypropyloxy]biphenyl, 2,2'-bis[3-(1-naphthyloxy)-2-acryloyloxypropyloxy]biphenyl, 2,2'-bis[3-(2-naphthyloxy)-2-acryloyloxypropyloxy]biphenyl, 2,2'-bis[3-(4-phenoxyphenyloxy)-2-acryloyloxypropyloxy]biphenyl, 2,2'-bis[3-(4-phenylphenyloxy)-2-methacryloyloxypropyloxy]biphenyl, 2,2'-bis[3-(3-phenylphenyloxy)-2-methacryloyloxypropyloxy]biphenyl, 2,2'-bis[3-(2-phenylphenyloxy)-2-methacryloyloxypropyloxy]biphenyl, 2,2'-bis[3-(1-naphthyloxy)-2-methacryloyloxypropyloxy]biphenyl, 2,2'-bis[3-(2-naphthyloxy)-2-methacryloyloxypropyloxy]biphenyl, 2,2'-bis[3-(4-phenoxyphenyloxy)-2-methacryloyloxypropyloxy]biphenyl 4,4'-bis(3-phenyloxy-2-acryloyloxypropyloxy)biphenyl, 3,3',5,5'-tetramethyl4,4'-bis(3-phenyloxy-2-acryloyloxypropyloxy)biphenyl, 4,4'-bis(3-phenyloxy-2-acryloyloxypropyloxy)diphenyl sulfide, 4,4'-bis(3-phenyloxy-2-acryloyloxypropyloxy)diphenyl sulfone, 1,1-bis(3-phenyloxy-2-acryloyloxypropyloxyphenyl)-1-phenylethane, 9,9'-bis[4-(3-phenyloxy-2-acryloyloxypropyloxy)phenyl]fluorene, 9,9'-bis[4-(3-phenyloxy-2-acryloyloxypropyloxy)-3-methylphenyl]fluorene, 4,4'-bis(3-phenyloxy-2-acryloyloxypropylthio)diphenyl sulfide, 4,4'-bis(3-phenyloxy-2-acryloyloxypropylthio)diphenyl sulfone, 4,4'-bis(3-phenyloxy-2-methacryloyloxypropyloxy)biphenyl, 3,3',5,5'-tetramethyl-4,4'-bis(3-phenyloxy-2-methacryloyloxypropyloxy)biphenyl, 4,4'-bis(3-phenyloxy-2-methacryloyloxypropyloxy)diphenyl sulfide, 4,4'-bis(3-phenyloxy-2-methacryloyloxypropyloxy)diphenyl sulfone, 1,1-bis(3-phenyloxy-2-methacryloyloxypropyloxyphenyl)-1-phenylethane, 9,9'-bis[4-(3-phenyloxy-2-methacryloyloxypropyloxy)phenyl]fluorene, 9,9'-bis[4-(3-phenyloxy-2-methacryloyloxypropyloxy)-3-methylphenyl]fluorene, 4,4'-bis(3-phenyloxy-2-methacryloyloxypropylthio)diphenyl sulfide, 4,4'-bis(3-phenyloxy-2-methacryloyloxypropylthio)diphenyl sulfone and the like.

The (meth)acrylic ester compound represented by the general formula (1) of the present invention is a new compound, but such a compound is produced by the use of a known synthesis reaction.

That is, according to a representative method, the (meth)acrylic ester compound is properly produced along the synthesis path represented by the following (Scheme I),

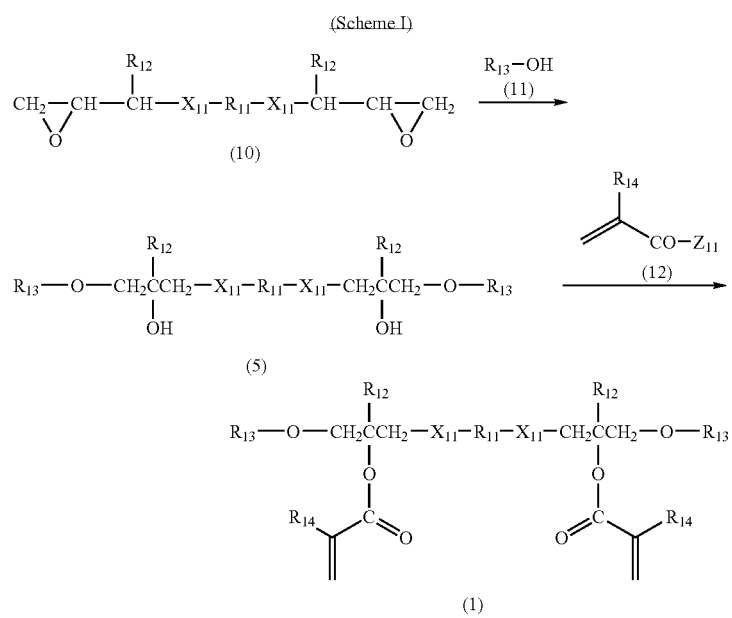

wherein $R_{11}$ to $R_{14}$ and $X_{11}$ are the same as those described before; and $Z_{11}$ represents a chlorine atom, a bromine atom, an OH group, an alkoxy group of 1 to 4 carbon atoms or a phenoxy group.

That is, a diglycidyl compound represented by the general formula (10) is reacted with a hydroxy compound in the general formula (11) to prepare a dihydroxy compound represented by the general formula (5) of the present invention as a synthesis intermediate. The (meth)acrylic ester compound represented by the general formula (1) of the present invention is properly produced, for example, by (meth)acrylic esterification of the thus-obtained dihydroxy compound represented by the general formula (5) using a (meth)acrylate represented by the general formula (12).

The diglycidyl compound represented by the general formula (10) to be a raw material is properly prepared by a known epoxidation reaction (for example, an industrial production method of the existing epoxy compound available as an industrial raw material or the like) typically with a dihydroxy compound such as a bisphenol compound or a dithiol compound and epihalohydrine as raw materials.

Each step of the reaction is explained in more detail below.

First, in the above (Scheme I) illustrating the reaction path, a method for producing the dihydroxy compound represented by the general formula (5) is described in detail hereinafter.

The dihydroxy compound represented by the general formula (5) is properly produced by stoichiometrically reacting 1 molecule of a diglycidyl compound represented by the general formula (10) with 2 molecules of a hydroxy compound in the general formula (11). Namely, a hydroxy group in the compound represented by the general formula (11) is subjected to a ring-opening addition reaction with a glycidyl group in the compound represented by the general formula (11).

The above production method itself is known, carried out by the reaction conditions that have been known from the past [for example, Chemical Pharmaceutical Bulletin., Vol. 19 (10), p. 2003 to 2008 (1971) and the like], and properly carried out in the presence of an appropriate catalyst (for example, an acid catalyst, a base catalyst or the like) as needed.

In this reaction, the amount of the hydroxy compound represented by the general formula (11) to be reacted with the diglycidyl compound represented by the general formula (10) is not particularly restricted, but it is usually from 0.1 to 10 moles, preferably from 0.5 to 5 moles, and more preferably from 0.8 to 3 moles, based on 1 mole of the diglycidyl compound represented by the general formula (10).

The above reaction may be carried out without any solvent or in a solvent. Such a solvent is not particularly restricted as far as it is an inactive solvent to the reaction. Examples thereof include hydrocarbon solvents such as n-hexane, benzene, toluene, xylene or the like; ketone solvents such as acetone, methylethylketone, methylisobutyl ketone or the like; ester solvents such as ethyl acetate, butyl acetate or the like; ether solvents such as diethylether, tetrahydrofuran, dioxane or the like; halogen solvents such as dichlolomethane, chloroform, carbon tetrachloride, 1,2-dichloloethane, perciene or the like; polar solvents such as N,N-dimethylformamide, N,N-dimethylacetamide, N,N-dimethylimidazolidinone, dimethyl sulfoxide, sulfolane or the like. These solvents may be used in combination of two or more kinds.

The reaction temperature is not particularly restricted, but it is usually in the range of 0 to 200° C., and preferably from 0 to 150° C. The reaction time depends on the conditions such as the reaction temperature or the like, but it is usually from several minutes to several tens of hours.

Next, a method for producing the (meth)acrylic ester compound represented by the general formula (1) in the above (Scheme I) is described in detail.

The (meth)acrylic ester compound represented by the general formula (1) is produced, as described above, by reacting a dihydroxy compound represented by the general formula (5) with (meth)acrylate represented by the general formula (12),

wherein, in the formula, $R_{14}$ represents the same as that described above; and $Z_{11}$ represents a chlorine atom, a bromine atom, an OH group, an alkoxy group of 1 to 4 carbon atoms or a phenoxy group.

As for the above method, known methods, such as those disclosed in Experimental Chemistry (Chemical Society of Japan) Vol. 19, p. 471 to 482 (1957), Journal of Organic Chemistry, Vol. 45, p. 5364 (1980), European Polymer Journal, Vol. 19, p. 399 (1983) and the like can be used.

That is, examples thereof include a method for reacting while dropping a (meth)acrylic acid halide ($Z_{11}$=a chlorine atom or a bromine atom) represented by the general formula (12) to the dihydroxy compound represented by the general formula (5) under stirring, or a method for carrying out a dehydration reaction of the dihydroxy compound represented by the general formula (5) with a (meth)acrylic acid ($Z_{11}$=OH group) represented by the general formula (12) and the like.

In the above reaction, the amount of (meth)acrylate represented by the general formula (12) to be reacted with the dihydroxy compound represented by the general formula (5) is not particularly restricted, but it is usually from 0.1 to 10 moles, preferably from 0.5 to 5 moles, and more preferably from 1 to 3 moles, based on 1 mole of the dihydroxy compound.

The reaction may be carried out without any solvent or in an inactive solvent to the reaction. Examples of such a solvent include hydrocarbon solvents such as n-hexane, benzene, toluene or the like; ketone solvents such as acetone, methylethylketone, methylisobutyl ketone or the like; ester solvents such as ethyl acetate, butyl acetate or the like; ether solvents such as diethylether, tetrahydrofuran, dioxane or the like; halogen solvents such as dichlolomethane, chloroform, carbon tetrachloride, 1,2-dichloloethane, perciene or the like. These solvents may be used in combination of two or more kinds.

The reaction temperature is not particularly restricted, but it is a temperature such that (meth)acrylate of a raw material or a (meth)acrylic ester compound of a reaction product is not polymerized, which is usually in the range of −78 to 150° C., preferably from −20 to 100° C., and more preferably from 0 to 80° C.

The reaction time depends on the reaction temperature, but it is usually from several minutes to 100 hours, preferably from 30 minutes to 50 hours, and more preferably from 1 to 20 hours. Furthermore, while confirming the reaction rate by known analytical methods (such as liquid chromatography, thin layer chromatography, IR and the like), it is also possible to stop the reaction at an arbitrary reaction rate.

By the reaction of the dihydroxy compound represented by the general formula (5) with acid halides of (meth)acrylate represented by the general formula (12), a hydrogen halide (for example, hydrogen chloride and the like) is generated as the by-product in the production of the acrylic ester compound of the present invention. So, organic bases such as triethylamine, pyridine, picoline, dimethylaniline, diethylaniline, 1,4-diazabicyclo[2.2.2]octane (DABCO), 1,8-diazabicyclo[5.4.0]undeca-7-ene (DBU) and the like, or inorganic bases such as sodium bicarbonate, sodium carbonate, potassium carbonate, lithium carbonate, sodium hydroxide, potassium hydroxide, calcium hydroxide, magnesium oxide and the like may be used as a dehydrochlorination agent.

The amount of the dehydrohalogenation agent is not particularly restricted, but it is from 0.1 to 10 moles, preferably from 0.5 to 5 moles, and more preferably from 1 to 3 moles, based on 1 mole of the dihydroxy compound represented by the general formula (5).

By the dehydration reaction of the dihydroxy compound represented by the general formula (5) with the (meth)acrylate ($Z_{11}$=OH group) represented by the general formula (12), various known esterification catalysts are preferably used in the production of the acrylic ester compound represented by the general formula (1) of the present invention.

Examples of the above catalyst include mineral acids (such as hydrochloric acid and sulfuric acid), organic acids (such as methane sulfonic acid, benzene sulfonic acid, and p-toluene sulfonic acid), Lewis acids (such as boron trifluoride and aluminum trichloride) and the like.

The amount of the catalyst used is not particularly restricted, but it is usually from 0.001 to 50 weight %, and preferably from 0.01 to 30 weight %, based on the mixture of reaction raw materials.

Furthermore, in order to promote the reaction, it is preferable to remove water which is the by-product out of the system. Of the aforementioned solvents, a solvent which is azeotroped with water (for example, benzene, toluene and the like) is used or a dehydrating agent such as molecular sieves and the like is used.

The dihydroxy compound represented by the general formula (5) is produced even by reacting a dihydroxy compound represented by the general formula (13) with a glycidyl ether compound represented by the general formula (14) as shown in the following (Scheme II) in addition to the method illustrated in (Scheme I). Such a reaction itself is carried out in the same manner as described in the above (Scheme I).

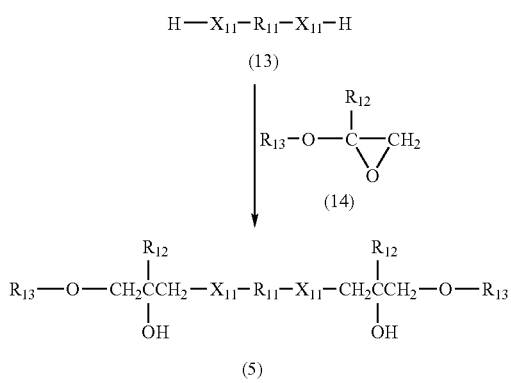

wherein $R_{11}$, $R_{12}$, $R_{13}$ and $X_{11}$ are the same as those described above.

In the above reaction, the amount of the glycidyl compound represented by the general formula (14) to be reacted with the compound represented by the general formula (13) is not particularly restricted, but it is usually from 0.1 to 10 moles, preferably from 0.5 to 5 moles, and more preferably from 0.8 to 3 moles, based on 1 mole of the dihydroxy compound represented by the general formula (13) (or a dithiol compound).

The (meth)acrylic ester compound in the general formula (1) is obtained by, for example, as shown in the following (Scheme III), a method comprising reacting the dihydroxy compound represented by the general formula (5) with halopropionic acids to obtain a halopropionic ester compound represented by the general formula (6) and then subjecting the thus-obtained compound to a dehydrohalogenation reaction to obtain a (meth)acrylic ester compound, in addition to the method in the above (Scheme I). As this method, the same method as described, for example, in Japanese Laid-open publication 1998-67736 can also be used.

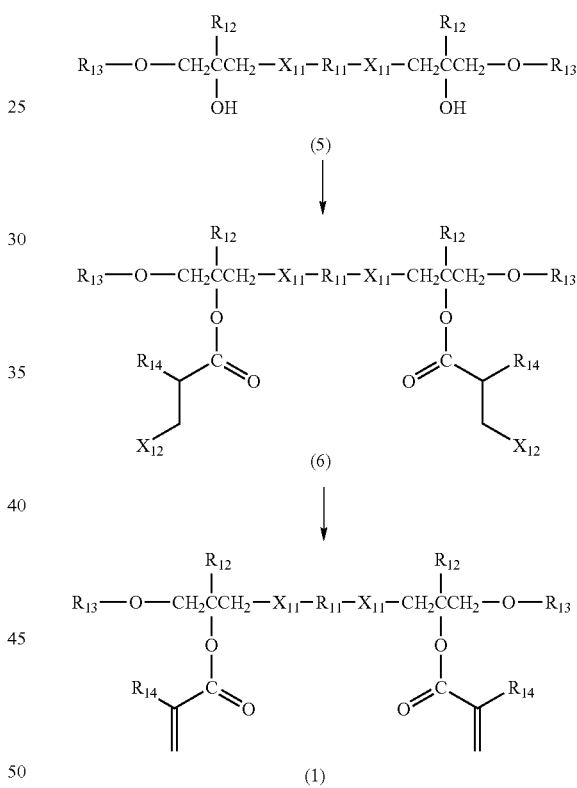

wherein, in the formula, $R_{11}$ to $R_{14}$, $X_{11}$ and $X_{12}$ are the same as those described above.

Incidentally, in the compound represented by the general formula (6), $X_{12}$ represents a halogen atom, and more preferably a chlorine atom.

To produce the (meth)acrylic ester compound represented by the general formula (1) of the present invention, it is preferable to use a polymerization inhibitor in order to prevent polymerization of the product in the middle of the reaction or after the reaction. As for the polymerization inhibitor, there can be exemplified, for example, various known compounds such as 4-methoxyphenol, hydroquinone, phenothiazine and the like. The amount of the polymerization inhibitor used is not particularly restricted, but it is usually from 0.01 to 5 weight %, and preferably from 0.05 to 3 weight %, based on the mixture of raw materials or the reaction product in the reactive system.

The (meth)acrylic ester compound represented by the general formula (1) of the present invention is isolated through the post-treatment according to the known operation and treatment method (for example, neutralization, solvent extraction, washing, separation, removal of solvent and the like) after the above reaction is completed. Furthermore, the (meth)acrylic ester compound is separated and purified by known methods (for example, chromatography, treatment by means of an activated carbon or various absorbents, and the like) and isolated as a compound with much higher purity as desired.

Also, it is desirable for such a compound to contain impurities such as insoluble substances, insoluble particles, wastes, dust, foreign substances and the like in a small amount by filtering at a state of solution to have high transparency. For example, the above impurities can be removed by filtering the (meth)acrylic ester compound represented by the general formula (1) using a filter in a clean room and the like.

Furthermore, as needed, an intermediate product is also subjected to the above operation and treatment method in the production of the (meth)acrylic ester compound represented by the general formula (1) for enhancing the purity.

A state of the compound represented by the general formula (1) according to the present invention is not particularly restricted. However, when it is used as a dental material, it is preferably liquid at a room temperature, and the viscosity at a room temperature is more preferably from 100 to 1,000,000 cps (mPa·s).

A compound which is liquid at a room temperature and has the aforementioned viscosity can be properly used for a dental material as a monomer as it is without subjecting to a polymerization. When the viscosity is lower than the above value, it might be difficult to obtain a polymerizable composition having desired properties. On the contrary, when the viscosity is higher than the above value, it tends to be difficult to homogeneously incorporate a sufficient amount of a filler to be described later such as an inorganic filler particularly including a glass powder and the like into the cured composition. Furthermore, it takes long time for the mixture with other components and it is impossible to terminate the polymerization reaction within a short period of time in some cases. The viscosity of the compound represented by the general formula (1) is particularly preferably in the range of 1,000 to 100,000 cps (mPa·s).

A compound which is liquid at a room temperature is preferable from the viewpoint of ease of use. For example, it is easy to dissolve other components or additives as a dental material or in the production of a cured product of the composition.

However, when it is used for a dental composition, the compound represented by the general formula (1) is not restricted to liquid. Even though it is solid, it can be used together with other liquid type polymerizable compounds.

The compound represented by the general formula (1) according to the present invention has a liquid refractive index at a room temperature of preferably from 1.53 to 1.65, and more preferably from 1.54 to 1.65.

Furthermore, in the compound represented by the general formula (1), a refractive index of a cured product thereof is preferably from 1.55 to 1.67, more preferably from 1.55 to 1.66, and further preferably from 1.56 to 1.65 at a room temperature. As described in detail below, this is to ensure transparency of the cured product after the composition is cured by allowing the refractive index of the cured product and that of the filler which coexists in the composition to agree with each other.

The compound represented by the general formula (1) may be used singly or together with a plurality of other compounds represented by the general formula (1) (at least two kinds).

Next, the polymerizable composition, the cured product thereof, and the optical part comprising the cured product are described in detail.

The polymerizable composition of the present invention comprises the (meth)acrylic ester compound represented by the general formula (1) and a polymerization initiator as essential components.

In this case, as the (meth)acrylic ester compound represented by the general formula (1), the aforementioned compound may be used singly or a plurality of different compounds as the (meth)acrylic ester compound represented by the general formula (1) may be used together.

The content of the (meth)acrylic ester compound represented by the general formula (1) occupied in the total weight of the polymerizable compound contained in the polymerizable composition of the present invention is not particularly restricted, but it is usually not less than 10 weight %, preferably not less than 20 weight %, more preferably not less than 30 weight %, and further preferably not less than 50 weight %.

The polymerization initiator for use in the polymerizable composition of the present invention is not particularly restricted, and known compounds which initiate a polymerization reaction by the heat (thermal polymerization initiator) or compounds which initiate polymerization by the light such as ultraviolet rays, visible rays (photopolymerization initiator) or the like can be used.

As the photopolymerization initiator, there can be exemplified, for example, known carbonyl compounds such as benzophenone, 4-methylbenzophenone, 4,4'-dichlorobenzophenone, 2,4,6-trimethylbenzophenone, methyl o-benzoylbenzoate, 4-phenylbenzophenone, 4-(4-methylphenylthio)benzophenone, 3,3-dimethyl-4-methoxybenzophenone, 4-(1,3-acryloyl-1,4,7,10,13-pentaoxatridecyl)benzophenone, 3,3',4,4'-tetra(tert-butylperoxycarbonyl)benzophenone, 4-benzoyl-N,N,N-trimethyl benzene metanaminium chloride, 2-hydroxy-3-(4-benzoylphenoxy)-N,N,N-trimethyl-1-propanaminium chloride, 4-benzoyl-N,N-dimethyl-N-[2-(1-oxo-2-propenyloxy)ethyl]benzene metanaminium bromide, 4-benzoyl-N,N-dimethyl-N-[2-(1-oxo-2-propenyloxy)ethyl]benzene metanaminium bromide, 2-isopropylthioxanthone, 4-isopropylthioxanthone, 2,4-dimethylthioxanthone, 2,4-diethylthioxanthone, 2,4-diisopropylthioxanthone, 2,4-dichlorothioxanthone, 1-chloro-4-propoxythioxanthone, 2-hydroxy-3-(3,4-dimethyl-9-oxo-9H-thioxanthone-2-yloxy)-N,N,N-trimethyl-1-propanaminium chloride, 2-benzoylmethylene-3-methyinaphto(1,2-d)thiazoline and the like;

dicarbonyl compounds such as Benzil, 1,7,7-trimethyl-bicyclo[2,2,1]heptane-2,3-dion(usually called camphorquinone), 2-methylanthraquinone, 2-ethylanthraquinone, 2-tert-butylanthraquinone, 1-chloroanthraquinone, 2-amylanthraquinone, 9,10-phenanthrenequinone, methyl α-oxobenzeneacetate and the like;

acetophenone type compounds such as acetophenone, 2-hydroxy-2-methyl-1-phenylpropane-1-on, 1-(4-isopropylphenyl)-2-hydroxy-2-methylpropane-1-on, 1-[4-(2-hydroxyethoxy)phenyl]-2-hydroxy-2-methylpropane-1-on, 1-hydroxycyclohexylphenylketone, dimethoxyacetophenone, diethoxyacetophenone, 2,2-dimethoxy-1,2-diphenylethane-1-on, 2,2-diethoxy-1,2-diphenylethane-1-on, 1,1-dichloroacetophenone, N,N-dimethylaminoacetophenone, 2-methyl-1-(4-methylthiophenyl)-2-morphorinopropane-1-on, 2-benzyl-2-dimethylamino-1-(4-morphorinophenyl)butane-1-on, 1-phenyl-1,2-propanedion-2-(o-ethoxycarbonyl) oxime, 3,6-bis(2-methyl-2-morphorinopropanoyl)-9-butylcarbazole and the like;

benzoine ether type compounds such as benzoine, benzoine methyl ether, benzoine ethyl ether, benzoine isopropyl ether, benzoine-n-butyl ether, benzoine isobutyl ether and the like;

allyl phosphineoxide type compounds such as 2,4,6-trimethylbenzoyl diphenylphosphineoxide, bis(2,6-dichlorobenzoyl)-(4-n-propylphenyl)phosphineoxide and the like;

aminocarbonyl compounds such as methyl 4-dimethylaminobenzate, ethyl 4-dimethylaminobenzate, 4-dimethylamino benzoic acid n-butoxy ethyl ester, 4-dimethylamino benzoic acid isoamyl ester, benzoic acid 2-dimethylamino ethyl ester, 4,4'-bisdimethylamino benzophenone (Michler's ketone), 4,4'-bisdiethylamino benzophenone, 2,5'-bis(4-dimethylaminobenzal)cyclopentanone, 2,5'-bis(4-diethylaminobenzal)cyclopentanone and the like;

halogen compounds such as 2,2,2-trichloro-1-(4'-tert-butylphenyl)ethane-1-on, 2,2-dichloro-1-(4-phenoxyphenyl)ethane-1-on, α,α,α-tribromomethylphenyl sulfone, 2,4,6-tris(trichloromethyl)triazine, 2,4-trichloromethyl-6-(4-methoxyphenyl)triazine, 2,4-trichloromethyl-6-(4-methoxystyryl)triazine, 2,4-trichloromethyl-6-piperonyl-triazine, 2,4-trichloromethyl-6-(3,4-methylenedioxyphenyl)-triazine, 2,4-trichloromethyl-6-(4-methoxynaphthyl)-triazine, 2,4-trichloromethyl-6-[2-furyl ethylidine]triazine, 2,4-trichloromethyl-6-[2-(5-methylfuryl-2-yl)ethylidine]triazine and the like; and known compounds such as 9-phenylacridine, 2,2'-bis(o-chlorophenyl)-4,4',5,5'-tetraphenyl-1,2-biimidazole, 2 2-azobis(2-aminopropane)dihydrochloride, 2,2, -azobis[2-(imidazoline-2-yl)propane]dihydrochloride and the like. These polymerization initiators may be used singly or in combination of two or more kinds.

The amount of the photopolymerization initiator used is from 0.001 to 10 parts by weight, preferably from 0.001 to 5 parts by weight, and further preferably from 0.01 to 2 parts by weight, based on 100 parts by weight of the polymerizable compound.

As for a thermal polymerization initiator, there can be exemplified, for example, peroxides such as benzoyl peroxide, p-chlorobenzoyl peroxide, diisopropyl peroxycarbonate, di-2-ethylhexyl peroxycarbonate, tert-butyl peroxypivalate and the like; and azo compounds such as azobisisobutyronitrile and the like.

The amount of the thermal polymerization initiator used is usually from 0.001 to 10 parts by weight, preferably from 0.001 to 5 parts by weight, and further preferably from 0.01 to 2 parts by weight, based on 100 parts by weight of the polymerizable compound.

As for the polymerizable compound used for the polymerizable composition of the present invention, known polymerizable compounds in addition to the acrylic ester compound represented by the general formula (1) can be used. Examples thereof include monofunctional or polyfunctional (meth) acrylates such as methyl (meth)acrylate, butyl (meth)acrylate, 2-ethylhexyl (meth)acrylate, ethylcarbitol (meth)acrylate, lauryl (meth)acrylate, tetracyclododecyl (meth)acrylate, phenoxyethyl (meth)acrylate, nonylphenoxyethyl (meth) acrylate, dicyclopentenyl (meth)acrylate, isobornyl (meth) acrylate, N-n-butyl-O-(meth)acryloyloxyethylcarbamate, acryloylmorpholine, trifluoroethyl (meth)acrylate, tribromobenzyl (meth)acrylate, perfluorooctylethyl (meth)acrylate, ethylene glycol di(meth)acrylate, propylene glycol di(meth)acrylate, neopentyl glycol di(meth)acrylate, 1,6-hexanediol di(meth)acrylate, triethylene glycol di(meth) acrylate, tripropylene glycol di(meth)acrylate, polyethylene glycol di(meth)acrylate, polypropylene glycol di(meth)acrylate, 2,2-bis(4-acryloyloxyphenyl)propane, 2,2-bis(4-methacryloyloxyphenyl)propane, bis(4-acryloyloxyphenyl)methane, bis(4-methacryloyloxyphenyl)methane, 4,4'-bis(2-acryloyloxy)phenyl sulfide, 4,4'-bis(2-methacryloyloxy)phenyl sulfide, 2,2-bis(4-acryloyloxyethoxyphenyl)propane, 2,2-bis(4-methacryloyloxyethoxyphenyl)propane, 2,2-bis[4-(2-acryloyloxypropoxy)phenyl]propane, 2,2-bis[4-(2-methacryloyloxypropoxy)phenyl]propane, bis(4-acryloyloxyethoxyphenyl)methane, bis(4-methacryloyloxyethoxyphenyl)methane, bis[4-(2-acryloyloxypropoxy)phenyl]methane, [4-(2-methacryloyloxypropoxy)phenyl]methane, 4,4'-bis(2-acryloyloxyethoxy)phenyl sulfide, 4,4'-bis(2-methacryloyloxyethoxy)phenyl sulfide, 4,4'-bis(2-acryloyloxypropoxy)phenyl sulfide, 4,4'-bis(2-methacryloyloxypropoxy)phenyl sulfide, 4,4'-bis(2-acryloyloxyethoxy)phenyl sulfone, 4,4'-bis(2-methacryloyloxyethoxy)phenyl sulfone, 4,4'-bis(2-acryloyloxypropoxy)phenyl sulfone, 4,4'-bis(2-methacryloyloxypropoxy)phenyl sulfone, di(meth)acrylate of ethylene oxide or propylene oxide adduct of 2,2-bis(4-hydroxyphenyl)propane, di(meth)acrylate of ethylene oxide or propylene oxide adduct of bis(4-hydroxyphenyl)methane, di(meth)acrylate of ethylene oxide or propylene oxide adduct of 4,4'-dihydroxyphenyl sulfide, trimethylolpropane tri(meth)acrylate, dipentaerythritol pentaacrylate, pentaerythritol triacrylate, pentaerythritol tetraacrylate, ditrimethylol tetraacrylate, dipentaerythritol hexaacrylate, 2-(meth)acryloyloxyethyl tris isocyanurate, (meth)acryloxypropyl tris(methoxy)silane and the like;

epoxy (meth)acrylates obtained by reacting a (meth) acrylic acid compound with various known monovalent or divalent or more epoxy compounds such as phenyl glycidyl ether, ethylene glycol diglycidyl ether, propylene glycol diglycidyl ether, resorcin diglycidyl ether, hydroquinone diglycidyl ether, bis(4-hydroxyphenyl)methane (usually called bisphenol F) diglycidyl ether, 2,2-bis(4-hydroxyphenyl)propane (usually called bisphenol A) diglycidyl ether, 4,4'-bishydroxyphenyl sulfide diglycidyl ether, 4,4'-bishydroxyphenyl sulfone (usually called bisphenol S) diglycidyl ether, 4,4'-biphenol diglycidyl ether, 3,3',5,5'-tetramethyl-4,4'-biphenol diglycidyl ether, tris(2,3-epoxypropyl)isocyanurate and the like;

epoxy (meth)acrylates obtained by reacting a (meth) acrylic acid compound with various known epoxy resins such as phenol novolak type epoxy resin, cresol novolak type epoxy resin, phenol xyloc type epoxy resin, bisphenol type epoxy resin and the like;

vinyl compounds such as vinylbenzene, divinylbenzene, trivinylbenzene, isopropenylbenzene, diisopropenylbenzene, triisopropenylbenzene, N-vinylpyrrolidone, N-vinylcaprolactam and the like;

various known polymerizable monomers such as compounds containing an allyl group including ethylene glycol diallylcarbonate, trimellitic acid triallyl ester, triallyl isocyanurate and the like; and various known polymerizable oligomers such as urethane (meth)acrylates, epoxy (meth)acrylates, polyester (meth) acrylates, polyether (meth)acrylates and the like.

The content of other polymerizable compounds occupied in the total weight of the polymerizable compound contained in the polymerizable composition of the present invention is not particularly restricted, but it is usually not more than 90 weight %, preferably not more than 80 weight %, more preferably not more than 70 weight %, and further preferably not more than 50 weight %.

As a method for producing the polymerizable composition of the present invention, it is specifically obtained by using the (meth)acrylic ester compound represented by the general formula (1) of the present invention along with various known polymerizable compounds as desired, further adding the aforementioned polymerization initiator, and then mixing and dissolving the resultant. The aforementioned polymerizable composition is used for polymerization and curing by removing any insoluble substances, foreign substances and the like by filtering before polymerizing the polymerizable composition as needed, and further sufficiently degassing it under a reduced pressure.

Furthermore, to prepare a polymerizable composition, various known additives such as an internal release agent, a light stabilizer, an ultraviolet light absorber, an anti-oxidant, a coloring pigment (for example, cyanine green, cyanine blue and the like), dyes, a flow regulator, an inorganic filler (for example, talc, silica, alumina, barium sulfate, magnesium oxide and the like) can also be added as needed in the ranges in which the object of the present invention is not impaired.

A cured product and an optical part comprising the cured product according to the present invention are obtained by polymerizing the polymerizable composition. In obtaining these cured product and optical part, various known methods have been adopted and have been properly carried out from the past. As representative examples, there can be exemplified a method comprising feeding the thus-obtained polymerizable composition into a mold and carrying out a casting polymerization by the radical reaction which is initiated by the heat or light, and the like.

A mold to be used is composed of, for example, two pieces of molds via a gasket made of polyethylene, ethylene-vinyl acetate copolymer, poly vinyl chloride and the like, or two pieces of molds fixed by a polyester adhesive tape or the like. As a mold, there can be mentioned, molds in combination of glass and glass, glass and a plastic plate, glass and a metal plate, and the like. Mirror surface-ground molds are preferable. Furthermore, various known processing methods such as the mold release process or the like may be performed for the mold.

As the radical polymerization reaction, there can be exemplified, for example as described above, a polymerization reaction by the heat (thermal polymerization), a polymerization by the light such as ultraviolet rays, visible rays or the like (photopolymerization), a polymerization reaction by the active energy line such as gamma rays or the like is used. A method in combination thereof can be cited.

When carrying out a polymerization by the light, the cured product or optical part obtained by the release from the mold may be subjected to an annealing process after the curing is completed, for the purpose of eliminating internal stress, distortion or the like.

Of these methods, the thermal polymerization requires several hours to several tens of hours, while the photopolymerization using ultraviolet rays or the like can be cured for several seconds to several minutes. So, the photopolymerization is preferable in consideration of the productivity in the production of optical parts of the present invention.

When carrying out the thermal polymerization, the polymerization temperature is influenced by the polymerization conditions such as the type of the polymerization initiator or the like and it is not particularly restricted. However, it is usually from 25 to 200° C., and preferably from 50 to 170° C.

As a molding method for obtaining an optical part, for example, a plastic optical lens, there has been proposed a method to obtain a lens by performing a casting polymerization by the light and/or the heat (for example, Japanese Laid-open publication 1985-135901, Japanese Laid-open publication 1998-67736, Japanese Laid-open publication 1998-130250 and the like), as described above. Namely, such a method is properly performed such that the polymerizable composition containing the (meth)acrylic ester compound represented by the general formula (1) of the present invention prepared according to the aforementioned method is introduced into the mold after degassing according to a proper method as needed, and the polymerization is usually carried out by an irradiation with the light for polymerization. Furthermore, the polymerization by the heat is properly carried out by a method comprising slowly heating from a low temperature to a high temperature for polymerization of the composition.

The thus-obtained plastic lens may be subjected to an annealing process as needed after the curing. Furthermore, for purposes of anti-reflection, imparting of high hardness, improvement of abrasion resistance, imparting of anti-fogging property or imparting of fashionability, various known physical or chemical processes such as surface polishing, anti-static treatment, hard coating process, anti-reflective coating process, dyeing process, photochromic process (for example, photochromic lens process and the like) and the like may be performed.

The polymerizable composition containing the (meth) acrylic ester compound represented by the general formula (1) of the present invention requires about several minutes to several hours for polymerization (curing) and molding by photopolymerization or the like. One of characteristics is that such a polymerizable composition can be polymerized within a short period of time as compared with the existing thermosetting optical resins represented by polydiethylene glycol diallylcarbonate, thus enabling high-speed molding. Furthermore, the cured product and the optical part according to the present invention are superior in the transparency and have high refractive index as compared with the existing known photocuring resins, and thus are also excellent in the mechanical properties and thermal properties.

As the optical parts of the present invention, there can be concretely mentioned, for example, various plastic lenses such as a spectacle lens for vision correction, a lens for cameras, a Fresnel lens for a liquid crystal projector, a lenticular lens, a contact lens and the like, a sealing material for a light emitting diode (LED), an optical waveguide, an optical adhesive to be used for junction of an optical lens and an optical waveguide, an anti-reflection film to be used for an optical lens and the like, transparent coating or transparent substrates to be used for a liquid crystal display-related members (substrate, light guiding plate, film, sheet and the like), and the like.

In particular, the cured product and the optical part according to the present invention can be molded within a short period of time by photopolymerization and are preferably used for plastic lenses such as a spectacle lens for vision correction, a lens for cameras, a Fresnel lens for a liquid crystal projector and the like, an optical adhesive, a sealing material for a light emitting diode (LED), transparent coating and the like, considering high refractive index, and excellent properties such as optical properties (transparency and Abbe number), thermal properties (heat distortion temperature and the like) and mechanical properties (impact resistance and the like).

The (meth)acrylic ester compound and the polymerizable composition containing the aforementioned compound according to the present invention are also used for purposes of hologram recording or the like as a photopolymerizable material which imparts transparent materials with high refractive index, in addition to the aforementioned optical parts.

Next, the dental material and the dental composition according to the present invention are described in detail.

The term "dental material" refers to a material widely used in the dental field, which includes the following dental composition. The dental composition refers to a mixture of a polymerization initiator, a filler and the like in addition to a polymerizable compound, and the dental composition includes an uncured polymerizable composition and a cured product obtained by polymerizing the polymerizable composition.

The dental material according to the present invention comprises a compound represented by the general formula (1). As described above, the above compound is a new (meth)acrylic ester compound partially having a plurality of aromatic ring structures such as a benzene ring, a biphenyl ring, a naphthalene ring or the like in a molecule.

The dental composition comprising (A) a polymerizable compound and (B) a polymerization initiator as essential components according to the present invention comprises a compound represented by the general formula (1) as the above polymerizable compound. The above dental composition may contain a filler as desired, as described below.

A polymerization initiator for the dental composition (or dental material) according to the present invention is not particularly restricted. For example, various known compounds (such as a photopolymerization initiator, an organic peroxide, a diazo compound, a redox compound and the like) are properly employable.

When the above photopolymerization initiator is used as a polymerization initiator, a photosensitizer alone or a combination of a photosensitizer and a photopolymerization accelerator can be used.

As for the photosensitizer, there can be exemplified, for example, known α-diketone compounds, phosphorus atom-containing compounds and the like which are excited by an irradiation with visible rays or ultraviolet rays to initiate polymerization, such as Benzil, camphorquinone, α-naphthyl, p,p'-dimethoxybenzil, pentadione, 1,4-phenanthrenequinone, naphthoquinone, trimethylbenzoyldiphenylphosphine oxide and the like. These compounds may be used singly or in combination of two or more kinds.

Of these compounds, camphorquinone and trimethylbenzoyldiphenylphosphine oxide are preferred compounds.

As the photopolymerization accelerator, there can be exemplified, for example, tertiary amines such as N,N-dimethylaniline, N,N-diethylaniline, N,N-dibenzylaniline, N,N-dimethyl-p-toluidine, N,N-diethyl-p-toluidine, N,N-dihydroxyethyl-p-toluidine, p-N,N-dimethylamino benzoic acid, p-N,N-diethylamino benzoic acid, ethyl p-N,N-dimethylaminobenzoate, ethyl p-N,N-diethylaminobenzoate, methyl p-N,N-dimethylaminobenzoate, methyl p-N,N-diethylaminobenzoate, p-N,N-dimethylaminobenzaldehyde, 2-n-butoxyethyl p-N,N-dimethylaminobenzoate, 2-n-butoxyethyl p-N,N-diethylaminobenzoate, p-N,N-dimethylamino benzonitrile, p-N,N-diethylaminobenzonitrile, p-N,N-dihydroxyethylaniline, p-dimethylaminophenethyl alcohol, N,N-dimethylaminoethyl methacrylate, triethylamine, tributylamine, tripropylamine, N-ethyl ethanolamine and the like; combinations of the above tertiary amines and citric acid, malic acid, or 2-hydroxypropanoic acid; barbituric acids such as 5-butylaminobarbituric acid, 1-benzyl-5-phenylbarbituric acid and the like; organic peroxides such as benzoyl peroxide, di-tert-butyl peroxide and the like. These compounds may be used singly or in combination of two or more kinds.

Of these compounds, preferably used are tertiary aromatic amines wherein a nitrogen atom is directly bonded to an aromatic ring or tertiary aliphatic amines having a polymerizable group, such as ethyl p-N,N-dimethylaminobenzoate, methyl p-N,N-dimethylaminobenzoate, 2-n-butoxyethyl p-N,N-dimethylaminobenzoate, N,N-dimethylaminoethyl methacrylate and the like.

In order to promote curing without delay, a combination of a photosensitizer and a photopolymerization accelerator is preferable, and preferably used is a combination of camphorquinone or trimethylbenzoyldiphenylphosphine oxide and an ester compound of a tertiary aromatic amine wherein a nitrogen atom is directly bonded to an aromatic ring, such as ethyl p-N,N-dimethylaminobenzoate, 2-n-butoxyethyl p-N,N-dimethylaminobenzoate or the like.

When an organic peroxide or a diazo compound is used as a polymerization initiator, various known compounds can be properly used without any restriction.

As for the organic peroxide, there can be exemplified, for example, diacyl peroxides, such as diacetyl peroxide, diisobutyl peroxide, didecanoyl peroxide, benzoyl peroxide, succinic acid peroxide and the like; peroxydicarbontes, such as diisopropyl peroxydicarbonate, di-2-ethylhexyl peroxydicarbonate, diallyl peroxydicarbonate and the like; peroxy esters, such as tert-butyl peroxyisobutyrate, tert-butyl neodecanate, cumene peroxyneodecanate and the like; sulfonyl peroxides such as acetylcyclohexylsulfonyl peroxide and the like.

Furthermore, as the diazo type compound, there can be exemplified, for example, 2,2'-azobisisobutyronitrile, 4,4'-azobis(4-cyanovaleric acid), 2,2'-azobis(4-methoxy-2,4-dimethoxyvaleronitrile), 2,2'-azobis(2-cyclopropylpropionitrile) and the like.

In order to complete polymerization within a short period of time, a compound whose decomposition half-life at 80° C. is not more than 10 hours is preferable. Of the above compounds, preferably used are benzoyl peroxide and 2,2'-azobisisobutyronitrile.

The type of the redox initiator used as a polymerization initiator is not particularly restricted and various known initiators are used.

For example, there can be exemplified a combination of the organic peroxide and the tertiary amine; a combination of the organic peroxide/sulfinic acid or its alkali metal salt/the tertiary amine; a combination of an inorganic peroxide and an inorganic reducing agent, such as a combination of an inorganic peroxide such as potassium persulfate and the like, and sodium sulfite or a combination of an inorganic peroxide and sodium hydrogensulfite. Of these, a combination of benzoyl peroxide and N,N-dimethyl-p-toluidine and a combination of benzoyl peroxide and N,N-dihydroxyethyl-p-toluidine are properly used.

The amount of the polymerization initiator used is not particularly restricted, but it is usually in the range of 0.001 to 10 weight %, and preferably in the range of 0.001 to 5 weight %, based on 100 parts by weight of the polymerizable compound.

The dental composition of the present invention contains a filler. The filler is added for the purposes of ensuring the mechanical strength, enhancing the light transmittance, imparting the X-ray contrast property and decreasing the polymerization shrinkage.

The filler used in the present invention is not particularly restricted. A known inorganic filler, an organic filler, or an organic-inorganic composite filler is usually used. In the present invention, an inorganic compound filler, particularly the following inorganic compound, is preferable.

An inorganic compound used as the filler in the present invention is generally a glass powder, and the glass powder has an average particle diameter of not more than 2 μm, and preferably from 0.1 to 1.5 μm. When the particle diameter is in this range, the specific area of the filler is not markedly increased. Hence, the relative proportion of the filler to the polymerizable compound is greatly increased, and therefore the polymerization shrinkage can be effectively decreased. The refractive index of the glass powder is preferably not less than 1.55, and particularly preferably in the range of 1.57 to 1.65.

Meanwhile, the difference between the refractive index of the glass powder for use in the present invention and the refractive index of a cured product (resin matrix) of the polymerizable compound in the dental composition containing this glass powder is preferably not more than 0.05, and particularly preferably not more than 0.02. That is to say, the glass powder for use in the present invention has a refractive index very approximate to that of a cured product of the polymerizable compound. By the use of such a glass powder, the light transmittance of a cured product of the dental composition of the present invention can be enhanced.

In general, it is clinically important that the presence of the filling material can be clearly confirmed by X-ray photograph, so that the glass powder for use in the present invention is preferably one having X-ray contrast property. In order to impart X-ray contrast property to the glass powder, an element having X-ray contrast property (heavy metal element), such as barium, strontium, zirconium, bismuth, tungsten, germanium, molybdenum, lanthanide or the like, is usually added as a glass-constituting element.

With increase of the amount of the heavy metal element that is added in order to impart X-ray contrast property to the glass powder, the refractive index of the glass powder tends to be higher. Accordingly, the heavy metal element of the glass powder in the dental composition of the present invention has a function of imparting X-ray contrast property to the glass powder and a function of changing the refractive index of the glass powder.

If the difference between the refractive index of the cured product of the polymerizable monomer such as the aforementioned (meth)acrylate or the like, and the refractive index of the glass powder is larger than 0.05, the transparency of the cured composition is lowered, thereby tending to lower the photocurability. Lowering of the photocurability results in a decrease of the curing depth or insufficient progress of the curing reaction, whereby properties of the cured product are lowered in some cases. When the refractive index of the glass powder is controlled, it is preferably to adjust the refractive index between the refractive index of the polymerizable monomer in the uncured state and the refractive index of the cured product of the polymerizable monomer. This is advantageous in that there is no change between the transparency of the composition before curing and the transparency of the composition after curing (cured product). Furthermore, by allowing the refractive index of the cured product of the monomer and the refractive index of the glass powder to agree with each other, the transparency of the composition after curing becomes the highest. The methods to control the refractive index can be properly used according to the requirements for the clinical site.

In case of the dental composition of the present invention containing not less than about 60 weight % of the glass powder with X-ray contrast property having an average particle diameter of about sub micron to several μm, if the refractive index of the glass powder contained in the composition is not less than 1.50, the cured product of the composition becomes transparent, and at the same time, the presence of the cured product can be clearly confirmed by X-rays. The glass power used at this time may be one kind of a glass powder or a mixture of two or more kinds of glass powders having different formulations. When plural kinds of glass powders having different formulations are used, the refractive indices of the glass powders are approximated to each other as much as possible, so that high transparency of a cured product after curing the dental composition of the present invention can be ensured.

The glass powder is usually used in the amount of from 5 to 2,000 parts by weight, preferably from 50 to 1,000 parts by weight, and more preferably from 100 to 700 parts by weight, based on 100 parts by weight of the polymerizable compound.

In the dental composition of the present invention, a composite filler may be used as the filler.

The composite filler for use in the present invention can be prepared by, for example, mixing a polymerizable compound, a glass powder and a thermal polymerization initiator such as benzoyl peroxide, thermally polymerizing the mixture, and then, pulverizing the resulting polymer.

By the use of the composite filler, the polymerization shrinkage of the dental composition of the present invention can be effectively reduced in the curing stage. Since the composite filler is prepared by polymerizing the polymerizable compound under such conditions (for example, thermal polymerization conditions) as are capable of raising the rate of polymerization higher than that in the photopolymerization conditions, the cured product exhibits higher mechanical properties than a cured product obtained by photopolymerization. Accordingly, by the incorporation of such a composite filler, the mechanical properties and abrasion resistance of the cured product of the dental composition according to the present invention are improved. Moreover, by allowing the refractive index of a cured product of a mixture of the glass powder used for the composite filler and a polymerizable compound for constituting the composite filler to agree with the refractive index of a cured product of the aforementioned polymerizable compound and the refractive index of the glass powder, higher transparency can be obtained. To the composite filler, fine particle silica, a filler other than the glass powder, such as metallic oxide, a pigment or the like may be added when needed. The average particle diameter of the composite filler is not particularly restricted, but it is usually from 1 to 100 μm, and preferably from 5 to 20 μm.

The amount of the composite filler used is usually from 5 to 2,000 parts by weight, and preferably from 50 to 700 parts by weight, based on 100 parts by weight of the polymerizable compound.

In the present invention, fine particle silica can be used as the filler in addition to the glass powder.

The fine particle silica employable herein is usually high-purity colloidal silica prepared by a gas phase process, and has no X-ray contrast property. Although the fine particle silica has no X-ray contrast property, it is sometimes added for the purpose of controlling the viscosity, tackiness of a paste. As the fine particle silica, high-purity colloidal silica prepared by, for example, a gas phase process may be used as it is, or high-purity colloidal silica may be used after hydrophobic treatment with a silane compound such as dimethyldichlorosilane. It is preferable to subject the fine particle silica to methacryloxysilane treatment or aminosilane treatment to increase affinity of the fine particle silica for the resin matrix, prior to use. The fine particle silica has a low refractive index of 1.45, and this refractive index is widely different from that of the filler used. However, the average particle diameter of the fine particle silica is usually not more than 0.05 μm and is considerably smaller than 0.3 to 0.7 μm that is a wavelength of visible ray, so that the fine particle silica does not greatly hinder the transparency. Since fine particle silica of smaller size can maintain transparency high, and hence it is preferable to use fine particle silica having an average particle diameter of not more than 0.01 μm from the viewpoint of maintenance of high transparency.

The fine particle silica is usually used in an amount in the range of 5 to 250 parts by weight, preferably in the range of 10 to 200 parts by weight, and particularly preferably in the range of 20 to 150 parts by weight, based on 100 parts by weight of the (meth)acrylate monomer contained in the dental composition of the present invention.

Next, other polymerizable compounds in addition to the (meth)acrylic ester compound represented by the general formula (1) are explained in detail.

The polymerizable compound is not particularly restricted and various known polymer compounds (polymerizable monomers, polymerizable oligomers or the like) that have been used in the field of dental materials are used.

In addition to the (meth)acrylic ester compound represented by the general formula (1), as other polymerizable compounds used in combination with the (meth)acrylic ester compound represented by the general formula (1), various known polymerizable compounds (such as, polymerizable monomers, polymerizable oligomers or the like) can be cited. In consideration of polymerizability, curability or the like, preferably used is usually a (meth)acrylate compound or a (meth)acrylamide compound.

The polymerizable compound is, for example, a monofunctional monomer, a polyfunctional monomer which forms a crosslinked structure in polymerizing to effectively enhance physical properties (for example, water absorption coefficient, mechanical properties such as flexural strength, abrasion resistance and the like) after polymerization, or an acid group-containing monomer which is added for the purpose of imparting to the composition, properties of adhesion to dentin or the like.

The polymerizable compound which can be used in the present invention is not particularly restricted. As described before, various known polymerizable compounds can be cited. Concrete examples thereof include alkyl ester compounds of (meth)acrylic acid such as methyl (meth)acrylate, ethyl (meth)acrylate, butyl (meth)acrylate, hexyl (meth)acrylate, 2-ethylhexyl (meth)acrylate, dodecyl (meth)acrylate, lauryl (meth)acrylate, cyclohexyl (meth)acrylate, benzyl (meth)acrylate, isobornyl (meth)acrylate, adamantyl (meth)acrylate and the like;

hydroxyalkyl ester compounds of (meth)acrylic acid such as 2-hydroxyethyl (meth)acrylate, 2- or 3-hydroxypropyl (meth)acrylate, 4-hydroxybutyl (meth)acrylate, 5-hydroxypentyl (meth)acrylate, 6-hydroxyhexyl (meth)acrylate, 1,2- or 1,3-dihydroxypropyl mono(meth)acrylate, erythritol mono(meth)acrylate and the like;

polyethylene glycol mono(meth)acrylate compounds such as diethylene glycol mono(meth)acrylate, triethylene glycol mono(meth)acrylate, polyethylene glycol mono(meth)acrylate, polypropylene glycol mono(meth)acrylate and the like;

(poly)glycol monoalkyl ether (meth)acrylate such as ethylene glycol monomethyl ether (meth)acrylate, ethylene glycol monoethyl ether (meth)acrylate, diethylene glycol monomethyl ether (meth)acrylate, triethylene glycol monomethyl ether (meth)acrylate, polyethylene glycol monomethyl ether (meth)acrylate, polypropylene glycol monoalkyl ether (meth)acrylate and the like;

fluoroalkyl esters of (meth)acrylic acid such as perfluorooctyl (meth)acrylate, hexafluorobutyl (meth)acrylate and the like;

silane compounds having a (meth)acryloxyalkyl group such as γ-(meth)acryloxypropyltrimethoxysilane, γ-(meth)acryloxypropyltri(trimethylsiloxy)silane and the like;

carboxylic acid-containing (meth)acrylate compounds such as β-methacryloyloxyethyl hydrogenphthalate, β-methacryloyloxyethyl hydrogensuccinate, β-methacryloyloxyethyl maleate and the like;

halogen-containing (meth)acrylate compounds such as 3-chloro-2-hydroxypropyl methacrylate and the like; and (meth)acrylate compounds having a heterocyclic ring such as tetrafurfuryl (meth)acrylate and the like.

Furthermore, as for the polyfunctional monomer, there can be exemplified, for example, poly(meth)acrylates of alkanepolyols such as ethylene glycol di(meth)acrylate, propylene glycol di(meth)acrylate, butylene glycol di(meth)acrylate, neopentyl glycol di(meth)acrylate, hexylene glycol di(meth)acrylate, trimethylopropane tri(meth)acrylate, pentaerythritol tetra(meth)acrylate and the like;

polyoxyalkanepolyol poly(meth)acrylate such as diethylene glycol di(meth)acrylate, triethylene glycol di(meth)acrylate, polyethylene glycol di(meth)acrylate, dipropylene glycol di(meth)acrylate, polypropylene glycol di(meth)acrylate, dibutylene glycol di(meth)acrylate, dipentaerythritol hexa(meth)acrylate and the like; and aliphatic, alicyclic or aromatic (meth)acrylates represented by the following formula,

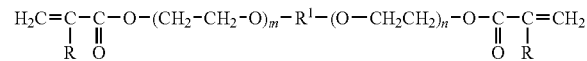

wherein, in the above formula, R represents a hydrogen atom or a methyl group; m and n represent 0 or a positive integer; and $R^1$ is a divalent linking group to be described below.

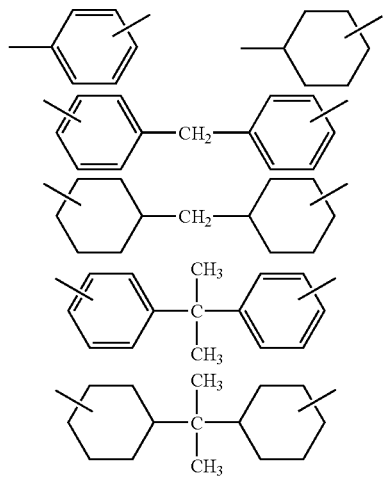

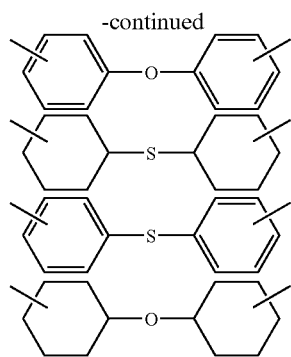

Also available are alicyclic or aromatic epoxy di(meth)acrylates represented by the following formula,

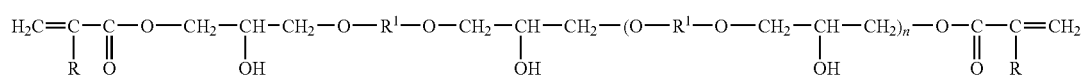

wherein, in the above formula, R represents a hydrogen atom or a methyl group; n represents 0 or a positive integer; and $R^1$ is $-(CH_2)_2-$, $-(CH_2)_4-$, $-(CH_2)_6-$ or a divalent linking group to be described below.

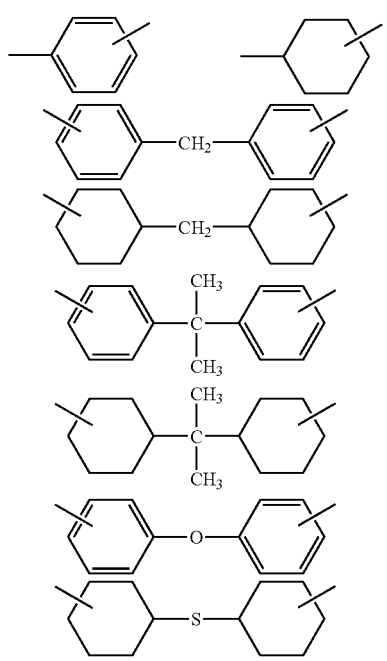

Also available are polyfunctional (meth)acrylates having an urethane bond in a molecule, which are represented by the following formula,

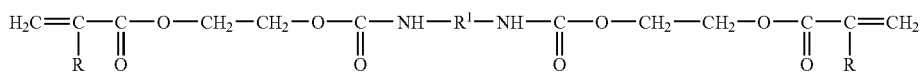

wherein, in the above formula, R represents a hydrogen atom or a methyl group; and $R^1$ is $-(CH_2)_2-$, $-(CH_2)_4-$, $-(CH_2)_6-$ or any one of the following;

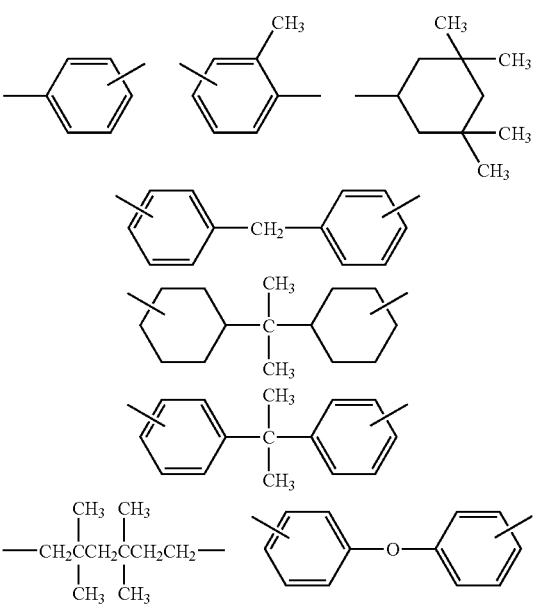

Furthermore, examples of the acid group-containing polymerizable monomers for use in the present invention are described below. As monomers having at least one carboxyl group in one molecule, there can be exemplified, for example, monocarboxylic acids, dicarboxylic acids, tricarboxylic acids, tetracarboxylic acids, and their derivatives. Examples of such acids and derivatives include (meth)acrylic acid, maleic acid, p-vinylbenzoic acid, 11-(meth)acryloyloxy-1,1-undecanedicarboxylic acid (MAC-10), 1,4-di(meth)acryloyloxyethylpyromellitic acid, 6-(meth)acryloyloxyethylnaphthalene-1,2,6-tricarboxylic acid, 4-(meth)acryloyloxymethyltrimellitic acid and anhydride thereof, 4-(meth)acryloyloxyethyltrimellitic acid and anhydride thereof, 4-(meth)acryloyloxybutyltrimellitic acid and anhydride thereof, 4-[2-hydroxy-3-(meth)acryloyloxy]butyltrimellitic acid and anhydride thereof, 2,3-bis(3,4-dicarboxybenzoyloxy)propyl (meth)acrylate, N-o-di(meth)acryloyloxytyrosine, o-(meth)acryloyloxytyrosine, N-(meth)acryloyloxytyrosine, N-(meth)acryloyloxyphenylalanine, N-(meth)acryloyl-p-aminobenzoic acid, N-(meth)acryloyl-o-aminobenzoic acid, N-(meth)acryloyl-5-aminosalicylic acid, N-(meth)acryloyl-4-aminosalicylic acid, 2-, 3- or 4-(meth)acryloyloxybenzoic acid, an addition product of 2-hydroxyethyl (meth)acrylate with pyromellitic dianhydride (PMDM), an addition product of 2-hydroxyethyl (meth)acrylate with maleic anhydride, an addition product of 2-hydroxyethyl (meth)acrylate with 3,3',4,4'-benzophenonetetracarboxylic dianhydride (BTDA), an addition product of 2-hydroxyethyl (meth)acrylate with 3,3',4,4'-biphenyltetracarboxylic dianhydride, 2-(3,4-dicarboxybenzoyloxy)-1,3-di(meth)acryloyloxypropane, an adduct of N-phenylglycine or N-tolylglycine with glycidyl (meth)acrylate, 4-[(2-hydroxy-3-(meth)acryloyloxypropyl)amino]phthalic acid, 3- or 4-[N-methyl-N-(2-hydroxy-3-(meth)acryloyloxypropyl)amino]phthalic acid and the like.

Furthermore, as monomers having at least one phosphoric acid group in one molecule, there can be exemplified, for example, 2-(meth)acryloyloxyethyl acid phosphate, 2- or 3-(meth)acryloyloxypropyl acid phosphate, 4-(meth)acryloyloxybutyl acid phosphate, 6-(meth)acryloyloxyhexyl acid phosphate, 8-(meth)acryloyloxyoctyl acid phosphate, 10-(meth)acryloyloxydecyl acid phosphate, 12-(meth)acryloyloxydodecyl acid phosphate, bis{2-(meth)acryloyloxyethyl}acid phosphate, bis{2- or 3-(meth)acryloyloxypropyl}acid phosphate, 2-(meth)acryloyloxyethylphenyl acid phosphate, 2-(meth)acryloyloxyethyl-p-methoxyphenyl acid phosphate and the like. In the above compounds, phosphoric acid group of these compounds can be replace with thiophosphoric acid group.

Furthermore, as monomers having at least one sulfonic acid group in one molecule, there can be exemplified, for example, 2-sulfoethyl (meth)acrylate, 2- or 1-sulfo-1- or 2-propyl (meth)acrylate, 1- or 3-sulfo-2-butyl (meth)acrylate, 3-bromo-2-sulfo-2-propyl (meth)acrylate, 3-methoxy-1-sulfo-2-propyl (meth)acrylate, 1,1-dimethyl-2-sulfoethyl (meth)acrylamide and the like.

Of the above compounds, particularly preferable are (meth)acrylic acid esters, which are low poisonous, can be rapidly polymerized, are hardly subjected to hydrolysis and are rapidly prepared. As the monofunctional polymerizable (meth)acrylic acid esters, particularly preferably used are, for example, alkyl methacrylates, such as methyl methacrylate (refractive index: 1.42) and ethyl methacrylate (refractive index: 1.42); hydroxyl group-containing (meth)acrylates, such as 2-hydroxyethyl methacrylate (refractive index: 1.45); (meth)acrylates having ethylene glycol chain in the molecule, such as diethylene glycol monomethyl ether methacrylate (refractive index: 1.44) and tetraethylene glycol monomethyl ether methacrylate (refractive index: 1.45), and the like.

As the polyfunctional polymerizable (meth)acrylic acid esters, particularly preferably used are, for example, di(meth)acrylates having an ethylene glycol chain in the molecule, such as ethylene glycol dimethacrylate (refractive index: 1.45) and triethylene glycol dimethacrylate (refractive index: 1.46); and compounds represented by the following formulae:

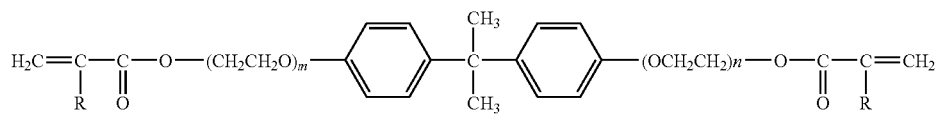

wherein, in the above formula, R represents a methyl group; and m+n is 2.6 on the average,

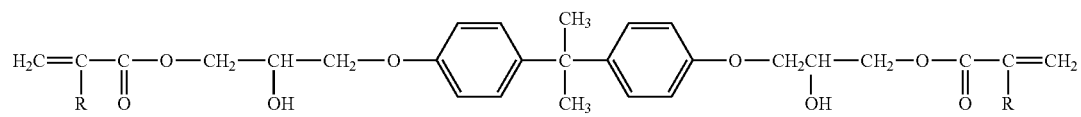

wherein, in the above formula, R represents a methyl group,

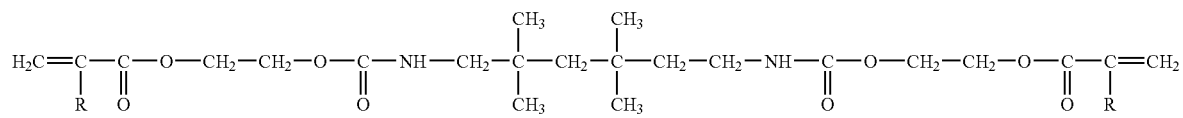

wherein, in the above formula, R represents a methyl group (refractive index: 1.48).

Furthermore, as the acid group-containing monomers, particularly preferably used are, for example, 11-methacryloyloxy-1,1-undecanedicarboxylic acid, 4-methacryloyloxyethyltrimellitic anhydride, N-methacryloyl-5-aminosalicylic acid, 2-(meth)acryloyloxyethylphenyl acid phosphate, 10-(meth)acryloyloxydecyl acid phosphate, 2-methyl-2-(meth)acrylamidopropanesulfonic acid and the like.

Other polymerizable compounds in addition to the (meth) acrylic ester compound represented by the general formula (1) are usually used in an amount in the range of 5 to 80 weight %, preferably in the range of 5 to 70 weight %, more preferably in the range of 5 to 50 weight %, and further preferably in the range of 10 to 40 weight %, based on 100 parts by weight of all polymerizable compounds contained in the dental composition of the present invention.

Further, the acid group-containing monomer is usually used in an amount in the range of 0.01 to 100 parts by weight, preferably in the range of 0.1 to 50 parts by weight, more preferably in the range of 0.5 to 20 parts by weight, and further preferably in the range of 1 to 10 parts by weight, based on 100 parts by weight of the polymerizable compound contained in the dental material or the dental composition of the present invention.

In the dental composition of the present invention, it is desirable to select and use the (meth)acrylate monomer in such a manner that the difference between the refractive index of a cured product of a mixture of the polymerizable compound represented by the general formula (1) and this monomer, and the refractive index of the glass powder to be added as a filler should become not more than 0.05, particularly in the range of 0 to 0.02.

By the polymerization of the (meth)acrylate monomer, the refractive index of a cured product of the monomer usually becomes higher than the refractive index of the monomer by about 0.02 to 0.03. Further, when a polar group such as a hydroxyl group or a carboxylic acid group, an aromatic ring, or a heavy element such as a halogen atom is incorporated into the (meth)acrylate monomer, the refractive index of the (meth)acrylate monomer generally tends to become higher than that of the monomer which does not contain such a group or an element. The refractive index of the monomer containing such a group or a heavy element is usually in the range of 1.48 to 1.54. On the other hand, the refractive index of a monomer having only an alkyl group as its structure or a (meth)acrylic monomer having a fluoroalkyl group tends to become lower than that of a monomer which does not have such a group, and the refractive index of the (meth)acrylic monomer is usually in the range of 1.40 to 1.48.

The content of other polymerizable compounds in the dental composition of the present invention is preferably in the range of 5 to 50 weight %, and particularly preferably in the range of 10 to 30 weight %.

The dental composition of the present invention contains at least the polymerizable compound represented by the general formula (1) and the polymerization initiator, and as needed, the filler, and to the composition, other components, such as pigments, dyes, a stabilizer, a polymer powder, a ultraviolet ray absorber and the like, may be added as needed, in the ranges in which the desired effects are not impaired.

In the process for preparing the composition of the present invention, the polymerizable compound (A) represented by the general formula (1), the polymerization initiator (B), the filler (C), and if desired, the polymerizable compound (D) other than the polymerizable compound (A) are dissolved and mixed to carry out the polymerization reaction. Since it is necessary that the polymerizable composition should not be contaminated by insoluble substances or foreign substances, the composition may be filtered to remove them prior to polymerization. It is more preferable to degas the composition under a reduced pressure prior to polymerization and curing, so that introduction of bubbles into the cured product can be prevented.

The dental composition of the present invention can complete the polymerization reaction by an irradiation with active rays such as ultraviolet rays or visible rays, similarly to the conventional photopolymerizable materials. Examples of light sources employable for the irradiation include a fluorescent lamp, various mercury lamps, a xenon lamp, a tungsten lamp, a halogen lamp, sunlight and the like. Meanwhile, the light irradiation time is from 1 second to 5 minutes. The temperature suitable for the photopolymerization is usually in the range of 0 to 100° C., and preferably in the range of 5 to 60° C. It is preferable to complete the polymerization and curing in the shortest time at a normal temperature in consideration of particularly the circumstances where the composition is used, such as a situation of the dental treatment and a burden on the patient, and the formulation of the composition may be adjusted so as to complete the polymerization curing in a period of 1 to 30 minutes.

The dental composition of the present invention satisfies the requirements for dental materials or compositions, such as mechanical strength, abrasion resistance, water resistance, curability and the like, and at the same time, has excellent and well-balanced transparency and X-ray contrast property though the transparency and the X-ray contrast property are hardly compatible with each other. The light transmittance (transparency) of a cured product of the dental composition is preferably not less than 1%, and more preferably not less than 5%. Further, the X-ray contrast property value of the dental composition is preferably from 100 to 1,000% (based on aluminum), and more preferably from 200 to 800% (based on aluminum). The composition of the present invention further has a property of small polymerization shrinkage in addition to the above properties. On this account, the composition of the present invention can be used for restoration of a defected part or filling of a cavity drilled, and besides the composition can be widely used for joining or adhesion of dentin of front teeth, preparation of temporary teeth, pontic of bridges, adhesion of facing crown, and the like.

Meanwhile, for the dental material of the present invention, the polymerizable compound (A) represented by the general formula (1) can be used singly or in combination with a plurality of different polymerizable compounds. In this case, the polymerizable compound is preferably liquid at a normal temperature and desirably has a viscosity of from 100 to 1,000,000 cps, and preferably from 1,000 to 100,000 cps at a normal temperature. This monomer is used as, for example, a primer that is used for undercoating before application of a resin adhesive or the like. To the polymerizable compound, additives, such as a germicide, a disinfectant, a stabilizer, a preservative and the like may be added as needed, in the ranges in which the object of the present invention is not impaired.

Further, the present invention includes a dental material containing a polymerization initiator that is used for curing, together with the polymerizable compound, and such a dental material can be used as, for example, a bonding agent, a resin type adhesive or a temporary adhesive. As the polymerization initiator, the same substance as used for the aforementioned curable composition is employable. Such a polymerization initiator is usually used in an amount, though not particularly restricted to, in the range of 0.001 to 10 weight %, and preferably in the range of 0.001 to 5 weight %, based on 100 parts by weight.

EXAMPLES

The present invention is now more specifically illustrated below with reference to Examples. However, the present invention is not restricted to these Examples.

<Preparation of an Acrylic Ester Compound Represented by the General Formula (1) of the Present Invention>

Preparation Example 1

Preparation of a Compound Represented by the Formula (5-1)

68.1 g (0.40 mole) of 4-phenylphenol, 0.53 g of 96% NaOH (1.2 weight % based on resorcin diglycidyl ether to be described below) and 40 g of N,N-dimethylacetamide were weighed and dissolved at 25° C. to obtain a mixture.

Thereinto was dropped a solution obtained by dissolving 44.4 g (0.20 mole) of resorcin diglycidyl ether having a main component of a compound represented by the formula (10-1) in 40 g of N,N-dimethylacetamide at 25° C. over an hour.

After the dropwise addition was completed, the resulting mixture was stirred at 100° C. for 6 hours, and then, it was confirmed that raw material was completely consumed by the high performance liquid chromatography (hereinafter referred to as HPLC analysis). Then, the reaction solution was diluted with 200 g of a mixed solvent of methanol and water (weight ratio=50/50). After the resulting precipitated crystal was filtered and collected, the collected reaction resultant was sludged with a mixed solvent of methanol and water at the same ratio as above for purification, followed by filtering to collect a crystal. The thus-collected crystal was dried to obtain 108.9 g of a dihydroxy compound represented by the formula (5-1) of a colorless powder crystal.

Yield 97%, Purity (HPLC analysis)≧95%

FD-MS (m/z): 562 (M+)

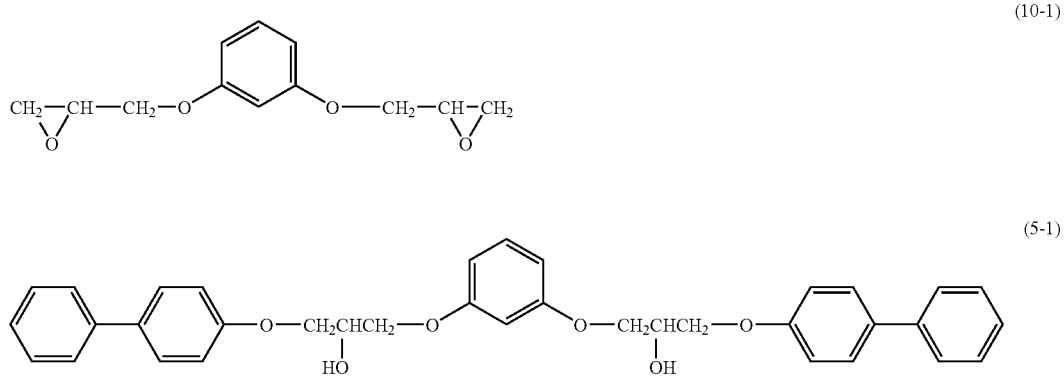

Preparation Example 2

Preparation of a Chloropropionic Acid Ester Compound Represented by the Formula (6-1)

56.27 g (0.10 mole) of a compound represented by the formula (5-1) prepared in Preparation Example 1 was dissolved in 60 g of N,N-dimethylacetamide to obtain a solution. Thereinto was dropped 45.70 g (0.36 mole) of 3-chloropropionic acid chloride at 60° C. over an hour. After the dropwise addition was completed, the resulting mixture was stirred at 60° C. for 4 hours, and then, it was confirmed that raw material was completely consumed by the HPLC analysis. The reaction solution was cooled down to 25° C. and discharged in ice water. The reaction product was extracted using 250 g of toluene and washed with 3% NaHCO$_3$ water. Then, the organic layer was repeatedly washed with water until it was neutralized. Then, the organic layer was separated and toluene was removed at 40° C. under a reduced pressure to obtain 76.60 g of a compound represented by the formula (6-1), i.e., a colorless, transparent and viscous liquid.

Yield 95%, Purity (HPLC analysis) 92.2%

EI-MS (m/z): 742 (M+)

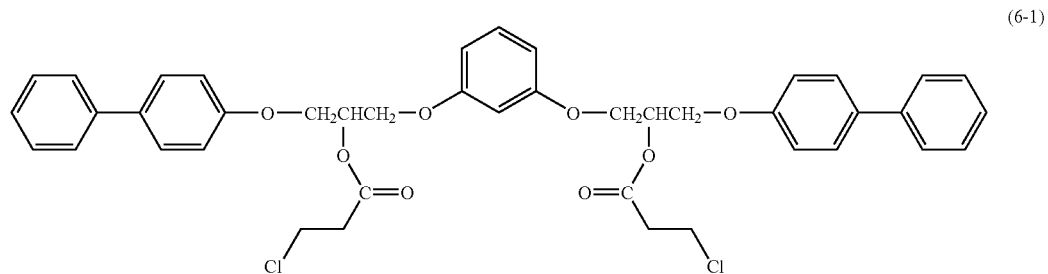

(6-1)

Preparation Example 3

Preparation of a Compound Represented by the Formula (5-2)

A dihydroxy compound represented by the formula (5-2) was obtained in the same manner as in Preparation Example 1, except that 1-naphthol was used instead of 4-phenylphenol used in Preparation Example 1.
EI-MS (m/z): 510 (M+)

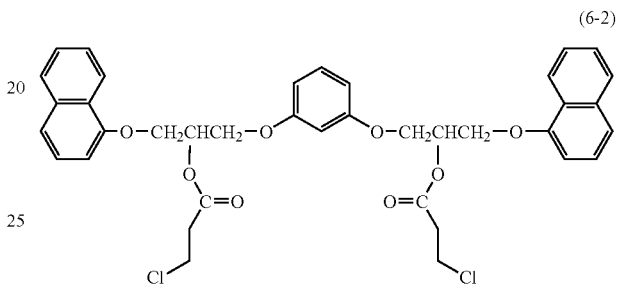

(6-2)

Preparation Example 5

Preparation of a Compound Represented by the Formula (5-3)

A dihydroxy compound represented by the formula (5-3) was obtained in the same manner as in Preparation Example 1, except that 2-naphthol was used instead of 4-phenylphenol used in Preparation Example 1.
EI-MS (m/z): 510 (M+)

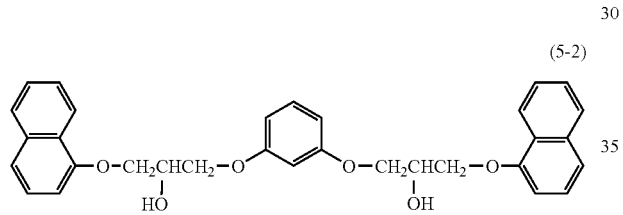

(5-2)

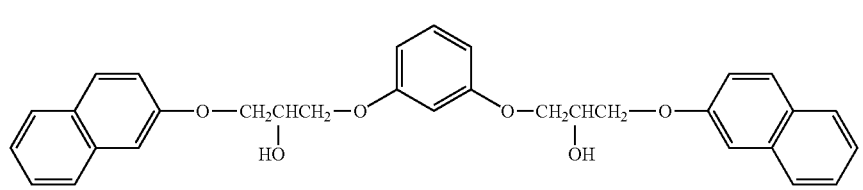

(5-3)

Preparation Example 4

Preparation of a Compound Represented by the Formula (6-2)

A chloropropionic acid ester compound represented by the formula (6-2) was obtained in the same manner as in Preparation Example 2, except that the dihydroxy compound represented by the formula (5-2) produced in Preparation Example 3 was used instead of the dihydroxy compound represented by the formula (5-1) used in Preparation Example 2.
EI-MS (m/z): 690 (M+)

Preparation Example 6

Preparation of a Compound Represented by the Formula (6-3)

A chloropropionic acid ester compound represented by the formula (6-3) was obtained in the same manner as in Preparation Example 2, except that the dihydroxy compound represented by the formula (5-3) produced in Preparation Example 5 was used instead of the dihydroxy compound represented by the formula (5-1) used in Preparation Example 2.
EI-MS (mlz): 690 (M+)

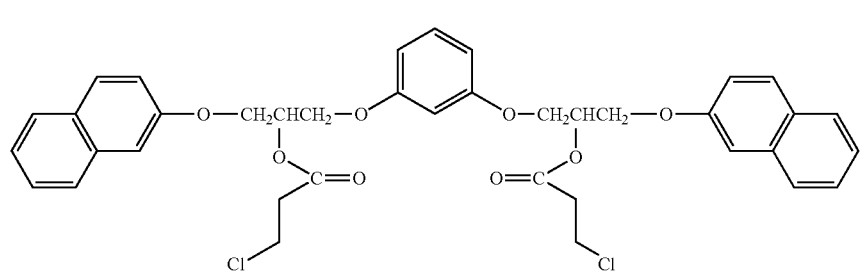
(6-3)

Preparation Example 7

Preparation of a Compound Represented by the Formula (5-4)

A dihydroxy compound represented by the formula (5-4) was obtained in the same manner as in Preparation Example 1, except that 2-phenylphenol was used instead of 4-phenylphenol used in Preparation Example 1.

EI-MS (m/z): 562 (M+)

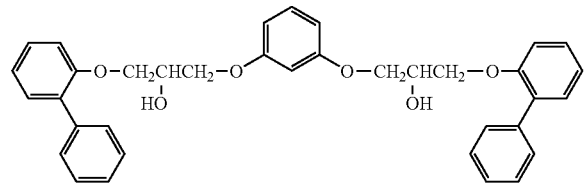
(5-4)

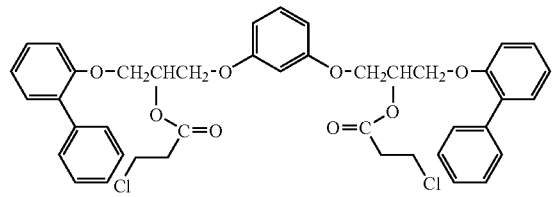
(6-4)

Preparation Example 9

Preparation of a Compound Represented by the Formula (5-5)

A dihydroxy compound represented by the formula (5-5) was obtained in the same manner as in Preparation Example 1, except that 4-phenoxyphenol was used instead of 4-phenylphenol used in Preparation Example 1.

FD-MS (m/z): 594 (M+)

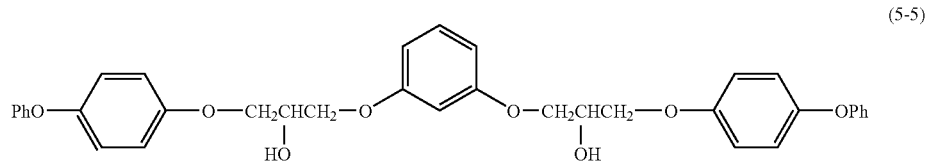
(5-5)

Preparation Example 8

Preparation of a Compound Represented by the Formula (6-4)

A chloropropionic acid ester compound represented by the formula (6-4) was obtained in the same manner as in Preparation Example 2, except that the dihydroxy compound represented by the formula (54) produced in Preparation Example 5 was used instead of the dihydroxy compound represented by the formula (5-1) used in Preparation Example 2.

EI-MS (m/z): 742 (M+)

Preparation Example 10

Preparation of a Compound Represented by the Formula (6-5)

A chloropropionic acid ester compound represented by the formula (6-5) was obtained in the same manner as in Preparation Example 2, except that the dihydroxy compound represented by the formula (5-5) produced in Preparation Example 5 was used instead of the dihydroxy compound represented by the formula (5-1) used in Preparation Example 2.

FD-MS (m/z): 774 (M+)

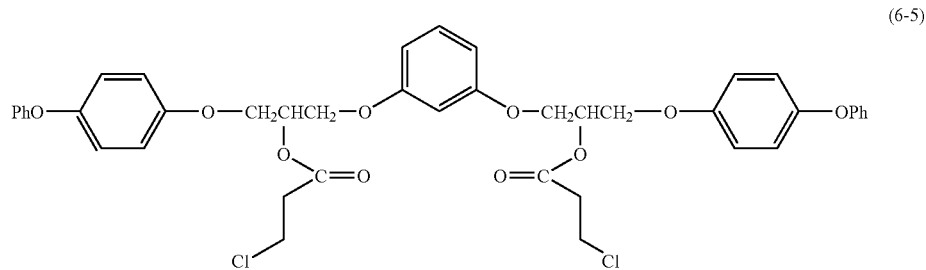

(6-5)

Preparation Example 11

Preparation of a Compound Represented by the Formula (5-6)

A dihydroxy compound represented by the formula (5-6) was obtained in the same manner as in Preparation Example 1, except that a compound represented by the formula (10-2) was used instead of the compound represented by the formula (10-1) used in Preparation Example 1.

FD-MS (m/z): 694 (M+)

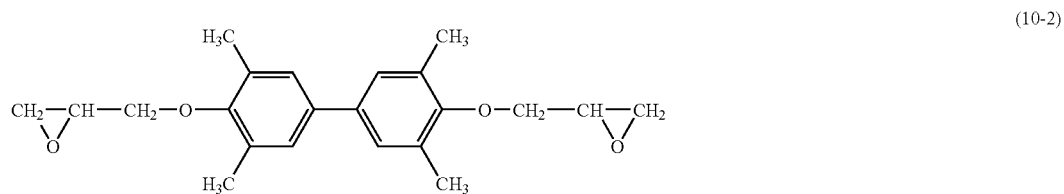

(10-2)

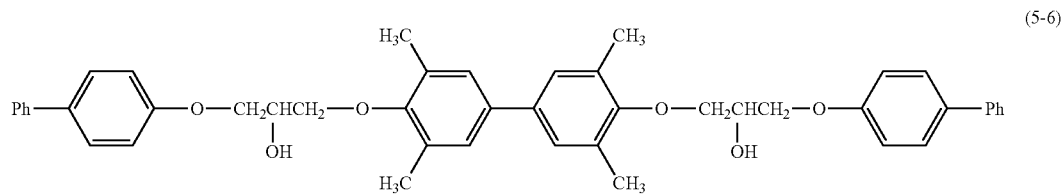

(5-6)

Preparation Example 12

Preparation of a Compound Represented by the Formula (6-6)

A chloropropionic acid ester compound represented by the formula (6-6) was obtained in the same manner as in Preparation Example 2, except that the dihydroxy compound represented by the formula (5-6) was used instead of the dihydroxy compound represented by the formula (5-1) used in Preparation Example 2.

FD-MS (m/z): 874 (M+)

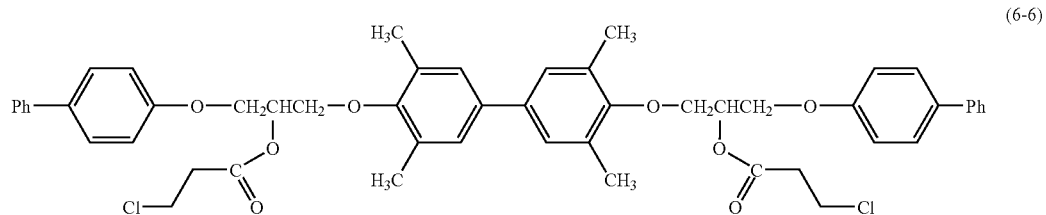

(6-6)

Preparation Example 13

Preparation of a Compound Represented by the Formula (5-7)

A dihydroxy compound represented by the formula (5-7) was obtained in the same manner as in Preparation Example 11, except that 2-phenylphenol was used instead of 4-phenylphenol used in Preparation Example 11.

FD-MS (m/z): 694 (M+)

Preparation Example 15

Preparation of a Compound Represented by the Formula (5-8) of the Present Invention)

50.00 g (0.27 mole) of 4,4'-biphenol, 0.97 g of 96% NaOH and 100 g of N,N-dimethylacetamide were weighed, mixed and dissolved at 25° C. The thus-obtained mixture was heated up to 100° C. and then, thereinto was dropped 80.80 g (0.54 mole) of phenyl glycidyl ether over 30 minutes. After the

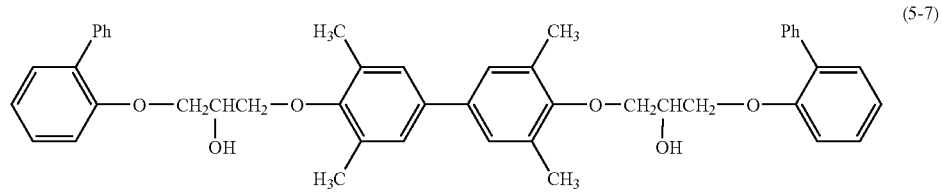

(5-7)

Preparation Example 14

Preparation of a Compound Represented by the Formula (6-7)

A chloropropionic acid ester compound represented by the formula (6-7) was obtained in the same manner as in Preparation Example 12, except that the dihydroxy compound represented by the formula (5-7) produced in Preparation Example 13 was used instead of the dihydroxy compound represented by the formula (5-6) used in Preparation Example 12.

FD-MS (m/z): 874 (M+)

dropwise addition was completed, the resulting mixture was stirred at 100° C. for 6 hours for the reaction, and then, it was confirmed that raw material was completely consumed by the HPLC analysis. Then, the reaction solution was added to 300 g of water and the precipitated crystal was filtered and collected. Subsequently, the collected reaction resultant was sludged with 300 g of water and further with 300 g of methanol for purification, followed by filtering to collect a crystal. The thus-collected crystal was dried at 80° C. for 10 hours to obtain 116.40 g of a dihydroxy compound represented by the formula (5-8), i.e., a light yellow powder crystal.

Purity (HPLC area percentage) 96.7%, Yield (purity conversion) 85%

Melting point 128.5~130° C.

FD-MS (m/z): 486 (M+)

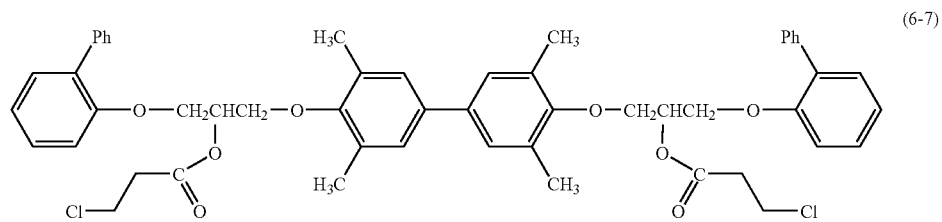

(6-7)

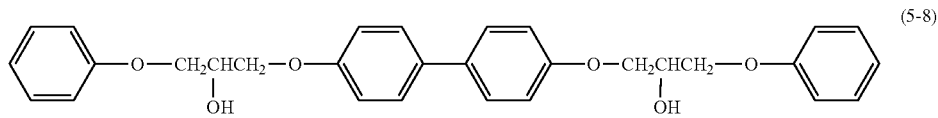

(5-8)

Preparation Example 16

Preparation of a Chloropropionic Acid Ester Compound Represented by the Formula (6-8)

60.37 g (0.12 mole: in terms of a purity of 96.7%) of a compound represented by the formula (5-8) produced in Preparation Example 15 was dissolved in 60 g of N,N-dimethylacetamide to obtain a solution. Thereinto was dropped 37.84 g (0.30 mole) of 3-chloropropionic acid chloride at 60° C. over an hour. After the dropwise addition was completed, the resulting mixture was stirred at 60° C. for 3 hours, and then, it was confirmed that raw material was completely consumed by the HPLC analysis. The reaction solution was cooled down to 25° C., and then, 150 g of toluene and 150 g of water were added thereto. The resulting mixture was stirred, extracted and separated to obtain a toluene solution layer. The obtained toluene layer was further stirred with 150 g of 3% NaHCO$_3$ aqueous solution for 10 minutes, and separated. Furthermore, obtained toluene layer was repeatedly washed with water until the water used for washing became neutralized, and separated. Then, toluene was removed at 40° C. under a reduced pressure to obtain 82.74 of a compound represented by the formula (6-8), i.e., a colorless, transparent and viscous liquid.

Purity (HPLC analysis) 94.7%, Yield 97.8%
FD-MS (m/z): 666 (M+)

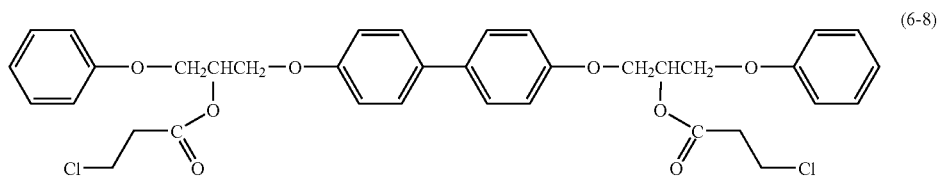

(6-8)

Preparation Example 17

Preparation of a Dihydroxy Compound Represented by the Formula (5-9)

A dihydroxy compound represented by the formula (5-9) of a light yellow and transparent liquid was obtained in the same manner as in Preparation Example 15, except that 4,4'-dihydroxydiphenylsulfide was used instead of 4,4'-biphenol used in Preparation Example 15.

FD-MS (m/z): 518 (M+)

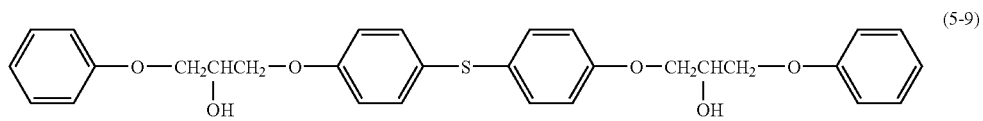

(5-9)

Preparation Example 18

Preparation of a Chloropropionic Acid Ester Compound Represented by the Formula (6-9)

A chloropropionic acid ester compound represented by the formula (6-9) of a colorless and transparent liquid was obtained in the same manner as in Preparation Example 16, except that the dihydroxy compound represented by the formula (5-9) was used instead of the dihydroxy compound represented by the formula (5-8) used in Preparation Example 16.

FD-MS (m/z): 698 (M+)

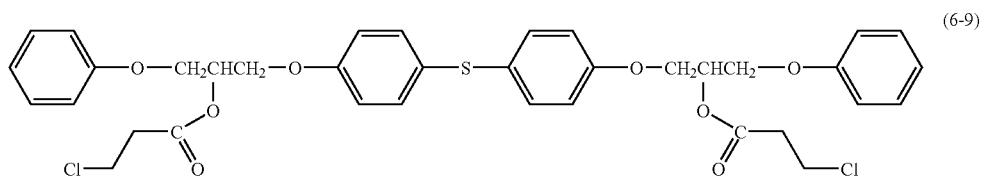

(6-9)

Preparation Example 19

Preparation of a Dihydroxy Compound Represented by the Formula (5-10)

A dihydroxy compound represented by the formula (5-10) of a light yellow and transparent liquid was obtained in the same manner as in Preparation Example 15, except that 4,4'-dihydroxydiphenylsulfone was used instead of 4,4'-biphenol used in Preparation Example 15.

FD-MS (m/z): 550 (M+)

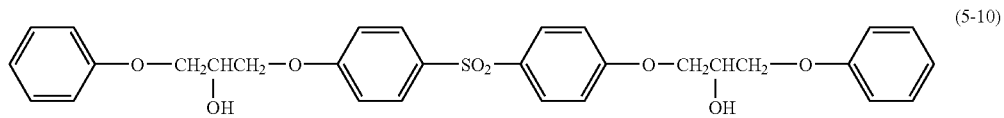

(5-10)

Preparation Example 20

Preparation of a Chloropropionic Acid Ester Compound Represented by the Formula (6-10)

A chloropropionic acid ester compound represented by the formula (6-10) of a colorless and transparent liquid was obtained in the same manner as in Preparation Example 16, except that the dihydroxy compound represented by the formula (5-10) was used instead of the dihydroxy compound represented by the formula (5-8) used in Preparation Example 16.

FD-MS (m/z): 730 (M+)

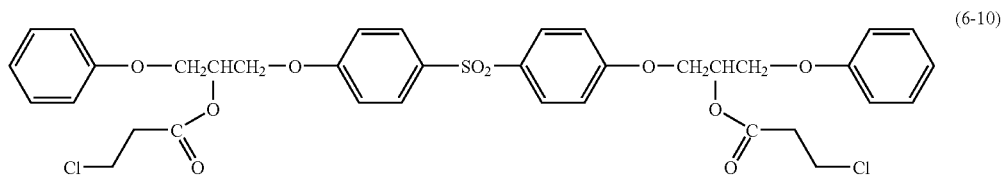

(6-10)

Preparation Example 21

Preparation of a Dihydroxy Compound Represented by the Formula (5-11)

A dihydroxy compound represented by the formula (5-11) of a colorless and transparent liquid was obtained in the same manner as in Preparation Example 15, except that 1,1-bis(4-hydroxyphenyl)phenylethane was used instead of 4,4'-biphenol used in Preparation Example 15.

FD-MS (m/z): 590 (M+)

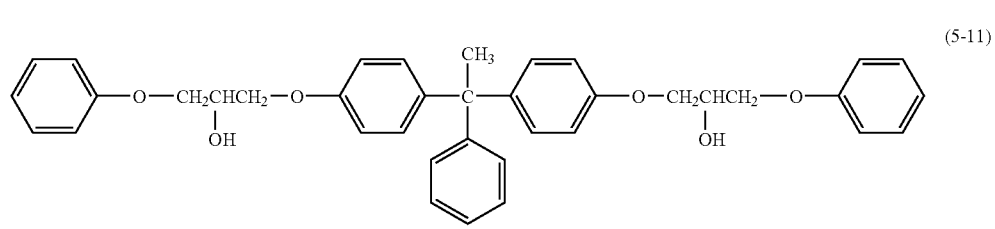

(5-11)

Preparation Example 22

Preparation of a Chloropropionic Acid Ester Compound Represented by the Formula (6-11)

A chloropropionic acid ester compound represented by the formula (6-11) of a colorless and transparent liquid was obtained in the same manner as in Preparation Example 16, except that the dihydroxy compound represented by the formula (5-11) was used instead of the dihydroxy compound represented by the formula (5-8) used in Preparation Example 16.

FD-MS (m/z): 770 (M+)

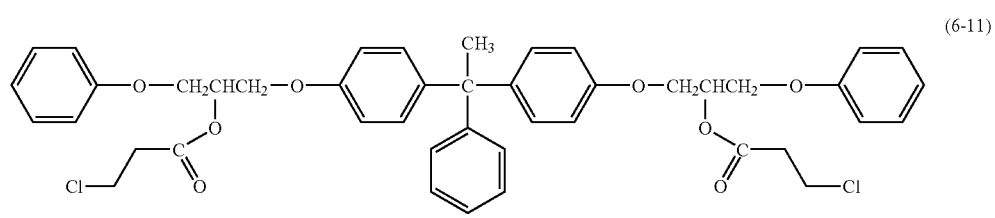

(6-11)

Preparation Example 23

Preparation of a Dihydroxy Compound Represented by the Formula (5-12)

A dihydroxy compound represented by the formula (5-12) of a colorless and transparent liquid was obtained in the same manner as in Preparation Example 15, except that 9,9-bis(4-hydroxyphenyl)fluorene was used instead of 4,4'-biphenol used in Preparation Example 15.

FD-MS (m/z): 650 (M+)

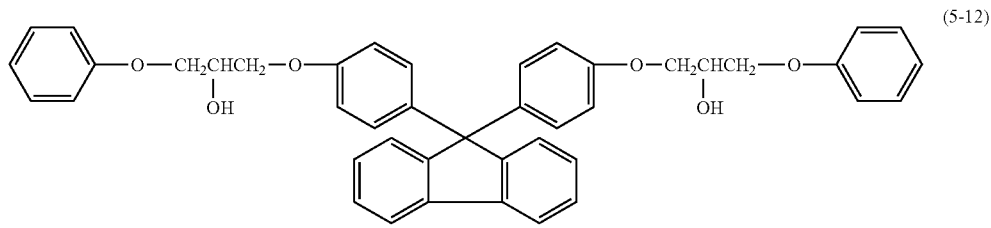

(5-12)

Preparation Example 24

Preparation of a Chloropropionic Acid Ester Compound Represented by the Formula (6-12)

A chloropropionic acid ester compound represented by the formula (6-12) of a colorless and transparent liquid was obtained in the same manner as in Preparation Example 16, except that the dihydroxy compound represented by the formula (5-12) was used instead of the dihydroxy compound represented by the formula (5-8) used in Preparation Example 16.

FD-MS (m/z): 830 (M+)

returned to a room temperature (25° C.). 200 g of toluene and 200 g of pure water were added to the reaction mixture to extract a product. After 5% hydrochloric acid was added to the toluene solution in the organic layer at a room temperature, washing with water and separation were repeated until no chlorine ion was detected, and then the organic layer was separated. After 62 mg of 4-methoxyphenol, i.e., a polymerization inhibitor was added thereto, toluene was removed at 35° C. under a reduced pressure and concentrated to obtain a crude product of a colorless and transparent liquid. The crude product was purified by silica-gel column chromatography

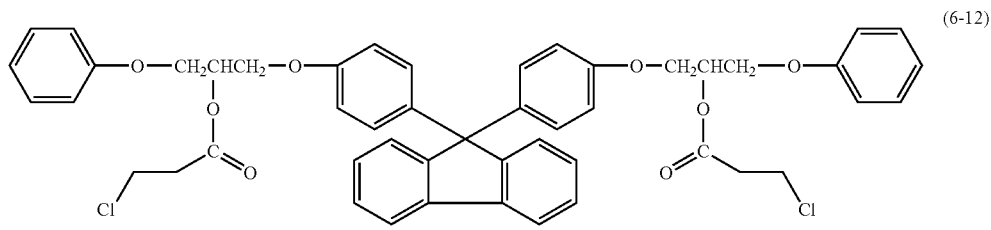

(6-12)

Example 1

Preparation of an Acrylic Ester Compound Represented by the Formula (1-1)

80.70 g (0.10 mole in terms of a purity) of the compound represented by the formula (6-1) produced in Preparation Example 2 was dissolved in 100 g of acetone to obtain a solution. Thereinto was dropped 36.40 g (0.36 mole) of triethylamine at 5° C. over an hour. After the dropwise addition was completed, the resulting mixture was stirred at 5° C. for another 2 hours for the reaction, and then, it was confirmed that raw material was completely consumed by the HPLC and (eluent:toluene) to obtain 55.7 g of an acrylic ester compound represented by the formula (1-1) of a colorless and transparent liquid.

Yield=80%, Purity (H PLC analysis)≧95%

$^1$H-NMR (500 MHz) E (CDCl$_3$); 4.20~4.30 (in, 8H), 5.50 5.60 (m, 2H), 5.85 (d, 2H), 6.10~6.20 (m, 2H), 6.45 (d,2H), 6.50~6.60 (m, 3H), 6.90~7.60 (m, 19H)

FD-MS (mlz); 670 (M+)

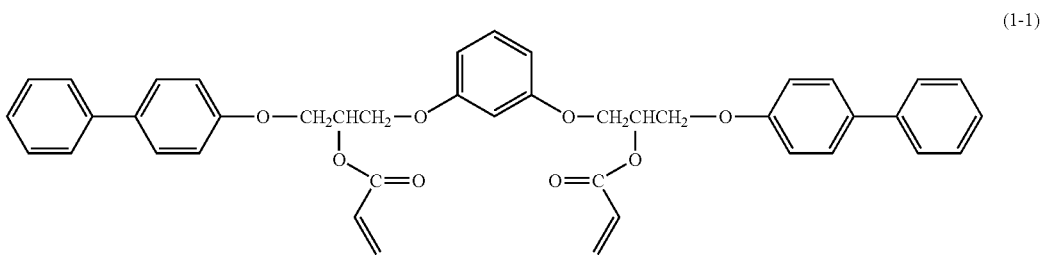

(1-1)

Example 2

An acrylic ester compound represented by the formula (1-2) was prepared in the same manner as in Example 1, except that the chloropropionic acid ester compound represented by the formula (6-2) was used instead of the chloropropionic acid ester compound represented by the formula (6-1) used in Example 1.

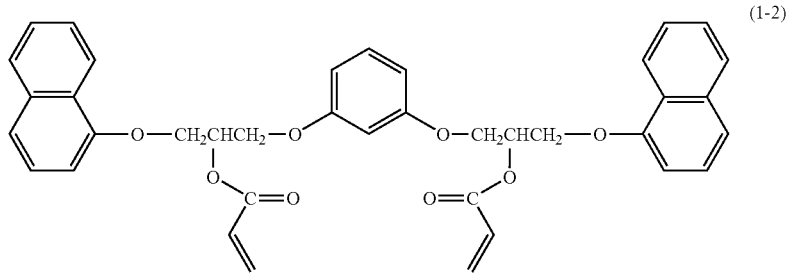

(1-2)

$^1$H-NMR (400 MHz) δ (CDCl$_3$); 4.40 (dd, 4H), 5.70~5.80 (m, 2H), 5.85 (d, 2H), 6.10~6.30 (dd, 2H), 6.45 (d, 2H), 6.50~6.60 (m, 3H), 6.80~6.90 (m, 2H), 7.10~7.50 (m, 10H), 7.60~7.80 (m, 6H)
IR; 1726 cm$^{-1}$ (—CO— stretching of an ester group)
EI-MS (m/z); 618 (M+)

Example 3

An acrylic ester compound represented by the formula (1-3) was prepared in the same manner as in Example 1, except that the chloropropionic acid ester compound represented by the formula (6-3) was used instead of the chloropropionic acid ester compound represented by the formula (6-1) used in Example 1.

$^1$H-NMR (400 MHz) δ (CDCl$_3$); 4.35 (dd, 4H), 5.50~5.70 (m, 2H), 5.85 (d, 2H), 6.10~6.20 (dd, 2H), 6.45 (d, 2H), 6.50~6.60 (m, 3H), 6.80~6.90 (m, 2H), 7.15~7.25 (m, 1H), 7.30~7.50 (m, 6H), 7.70~7.90 (m, 2H), 8.20~8.30 (m, 2H)
IR; 1630 cm$^{-1}$ (C=C stretching of an acrylic group), 1725 cm$^{-1}$ (—CO— stretching of an ester group)
EI-MS (m/z); 618 (M+)

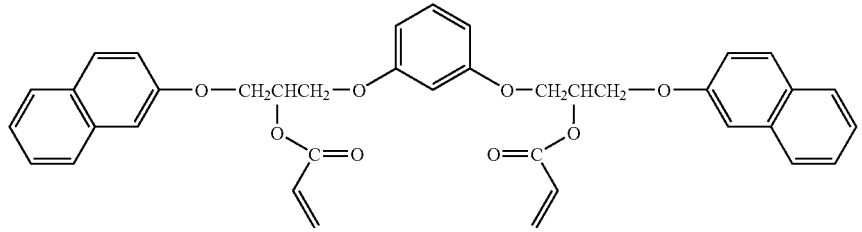

(1-3)

Example 4

An acrylic ester compound represented by the formula (1-4) was prepared in the same manner as in Example 1, except that the chloropropionic acid ester compound represented by the formula (6-4) was used instead of the chloropropionic acid ester compound represented by the formula (6-1) used in Example 1.

$^1$H-NMR (500 MHz) δ (CDCl$_3$); 4.05~4.10 (m, 4H), 4.20~4.30 (m, 4H), 5.40~5.50 (m, 2H), 6.05~6.15 (dd, 2H), 6.35 (d, 2H), 6.40~6.45 (m, 3H), 6.95~7.50 (m, 19H)
IR; 1630 cm$^{-1}$ (C=C stretching of an acrylic group), 1725 cm$^{-1}$ (—CO— stretching of an ester group)
FD-MS (m/z); 670 (M+)

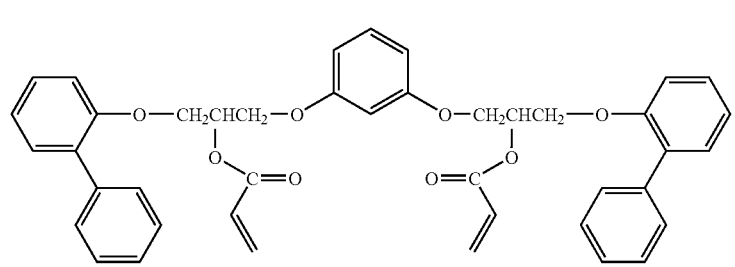

(1-4)

Example 5

An acrylic ester compound represented by the formula (1-5) was prepared in the same manner as in Example 1, except that the chloropropionic acid ester compound represented by the formula (6-5) was used instead of the chloropropionic acid ester compound represented by the formula (6-1) used in Example 1.

$^1$H-NMR (500 MHz) δ (CDCl$_3$); 4.20~4.30 (m, 8H), 5.50~5.60 (m, 2H), 5.86 (d, 2H), 6.10~6.20 (dd, 2H), 6.45 (dd, 2H), 6.50~6.60 (m, 3H), 6.80~7.30 (m, 19H)

IR; 1630 cm$^{-1}$ (C=C stretching of an acrylic group), 1725 cm$^{-1}$ (—CO— stretching of an ester group)

FD-MS (m/z); 702 (M+)

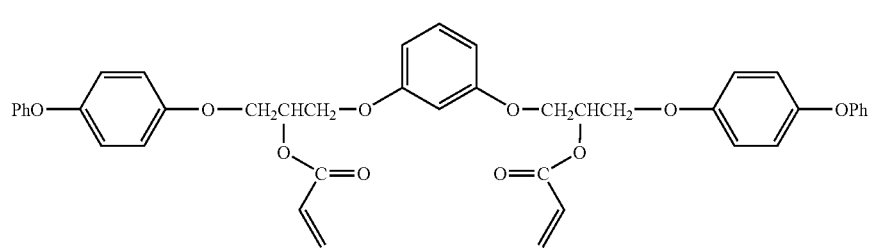

(1-5)

Example 6

An acrylic ester compound represented by the formula (1-6) was prepared in the same manner as in Example 1, except that a chloropropionic acid ester compound represented by the formula (6-6) was used instead of the chloropropionic acid ester compound represented by the formula (6-1) used in Example 1.

$^1$H-NMR (500 MHz) ( (CDCl3); 2.30 (s, 12H), 4.10~4.20 (m, 4H), 4.35~4.45 (m, 4H), 5.55~5.60 (m, 2H), 5.90 (d, 2H), 6.20 (dd, 2H), 6.50 (d, 2H), 7.02 (d, 4H), 7.15 (s, 4H), 7.25~7.30 (m, 2H), 7.35~7.45 (m, 4H), 7.50~7.55 (m, 8H)

FD-MS (m/z); 802 (M+)

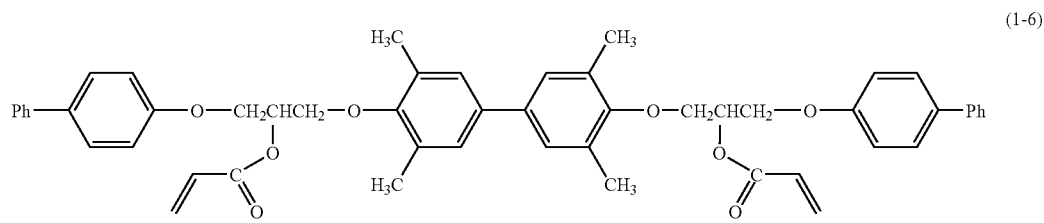

(1-6)

Example 7

An acrylic ester compound represented by the formula (1-7) was prepared in the same manner as in Example 1, except that the chloropropionic acid ester compound represented by the formula (6-7) was used instead of the chloropropionic acid ester compound represented by the formula (6-1) used in Example 1.

$^1$H-NMR (500 MHz) δ (CDCl$_3$); 2.16 (s, 12H), 3.90~3.95 (m, 4H), 4.30~4.35 (m, 4H), 5.45~5.50 (m, 2H), 5.87 (d, 2H), 6.15 (dd, 2H), 6.43 (d, 2H), 7.00~7.15 (d, 8H), 7.20~7.35 (m, 10H), 7.50 (d, 4H)

FD-MS (m/z); 802 (M+)

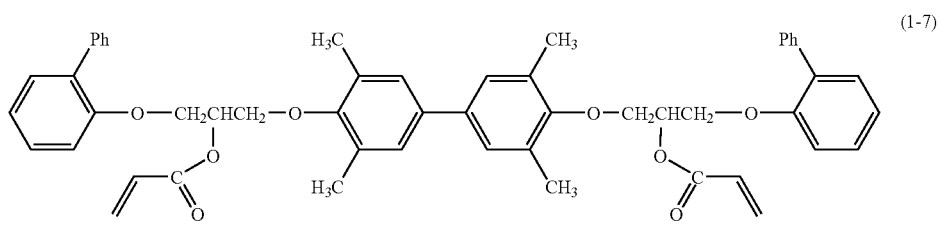

(1-7)

Example 8

An acrylic ester compound represented by the formula (1-8) of a colorless and transparent liquid was obtained in the same manner as in Example 1, except that the chloropropionic acid ester compound represented by the formula (6-8) was used instead of the chloropropionic acid ester compound represented by the formula (6-1) used in Example 1.

$^1$H-NMR (400 MHz) δ (CDCl$_3$); 4.30~4.40 (m, 8H), 5.55~5.65 (m, 2H), 5.88 (d, 2H), 6.10 (dd, 2H), 6.45 (d, 2H), 6.90~7.05 (m, 10H), 7.25~7.35 (m, 14H), 7.45~7.50 (m, 4H)

FD-MS (m/z); 594 (M+)

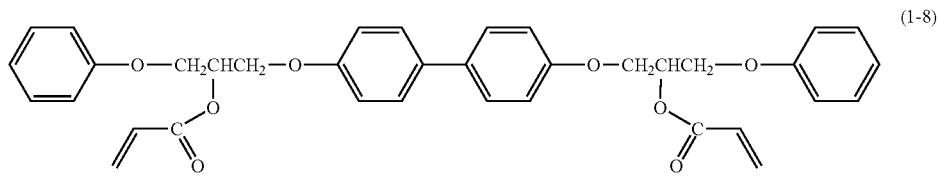

(1-8)

Example 9

An acrylic ester compound represented by the formula (1-9) of a colorless and transparent liquid was obtained in the same manner as in Example 1, except that the chloropropionic acid ester compound represented by the formula (6-9) was used instead of the chloropropionic acid ester compound represented by the formula (6-1) used in Example 1.

$^1$H-NMR (500 MHz) δ (CDCl$_3$); 4.20~4.30 (m, 8H), 5.50~5.55 (m, 2H), 5.85 (d, 2H), 6.14 (dd, 2H), 6.41 (d, 2H), 6.80~6.96 (m, 10H), 7.20~7.28 (m, 8H)

FD-MS (m/z); 626 (M+)

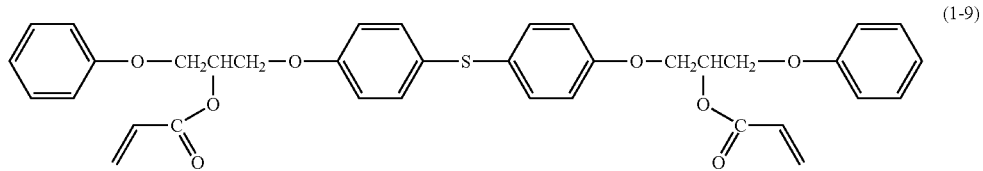

(1-9)

Example 10

An acrylic ester compound represented by the formula (1-10) of a colorless and transparent liquid was obtained in the same manner as in Example 1, except that the chloropropionic acid ester compound represented by the formula (6-10) was used instead of the chloropropionic acid ester compound represented by the formula (6-1) used in Example 1.

$^1$H-NMR (400 MHz) δ (CDCl$_3$); 4.25 (dd, 8H), 5.50~5.55 (m, 2H), 5.85 (d, 2H), 6.15 (dd, 2H), 6.45 (d, 2H), 6.85~7.00 (m, 10H), 7.25~7.30 (m, 4H), 7.75~7.90 (m, 4H)

FD-MS (m/z); 658 (M+)

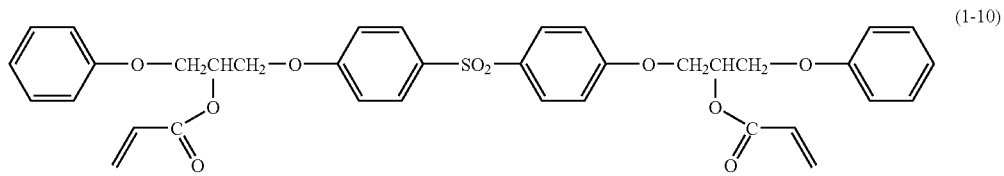

(1-10)

Example 11

An acrylic ester compound represented by the formula (1-11) of a colorless and transparent liquid was obtained in the same manner as in Example 1, except that the chloropropionic acid ester compound represented by the formula (6-11) was used instead of the chloropropionic acid ester compound represented by the formula (6-1) used in Example 1.

$^1$H-NMR (400 MHz) δ (CDCl$_3$); 2.15 (s, 3H), 4.25~4.35 (m, 8H), 5.55~5.60 (m, 2H), 5.85 (d, 2H), 6.17 (dd, 2H), 6.45 (d, 2H), 6.80~6.90 (m, 4H), 6.95~7.05 (m, 10H), 7.08~7.12 (m, 4H), 7.18~7.23 (m, 7H)

FD-MS (m/z); 698 (M+)

Example 12

An acrylic ester compound represented by the formula (1-12) of a colorless and transparent liquid was obtained in the same manner as in Example 1, except that the chloropropionic acid ester compound represented by the formula (6-12) was used instead of the chloropropionic acid ester compound represented by the formula (6-1) used in Example 1.

$^1$H-NMR (400 MHz) δ (CDCl$_3$); 4.15~4.25 (m, 8H), 5.45~5.55 (m, 2H), 5.80 (d, 2H), 6.10 (dd, 2H), 6.40 (d, 2H), 6.70~6.80 (m, 4H), 6.85~6.95 (m, 6H), 7.00~7.10 (m, 4H), 7.20~7.40 (m, 10H), 7.70 (d, 2H)

FD-MS (m/z); 759 (M+)

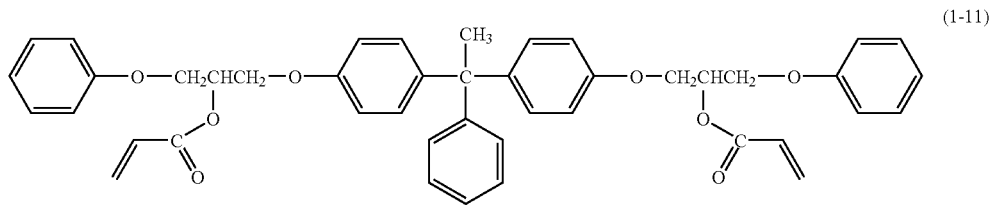

(1-11)

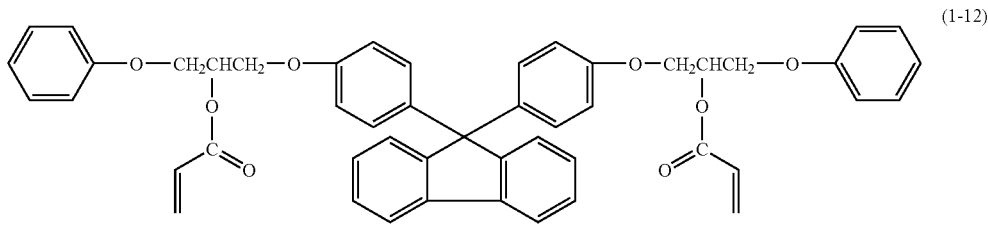

(1-12)

<Preparation of the Dental Material and the Dental Composition of the Present Invention>

The present invention is now more specifically illustrated below with reference to Examples and Comparative Examples. However, the present invention is not restricted to these Examples.

A list and abbreviations of the materials used in Examples are mentioned below.

Monomer
MNA-80: a compound represented by the formula (1-1)
MNA-81: a compound represented by the formula (1-2)
MNA-82: a compound represented by the formula (1-5)
MNA-83: a compound represented by the formula (1-4)
MNA-85: a compound represented by the formula (1-3)
MNA-92: a compound represented by the formula (1-6)
MNA-94: a compound represented by the formula (1-7)
MNA-104: a compound represented by the formula (1-8)
MNA-105: a compound represented by the formula (1-11)
MNA-106: a compound represented by the formula (1-9)
MNA-107: a compound represented by the formula (1-10)
Bis-GMA: 2,2-bis[4-(2-hydroxy-3-methacryloxypropoxy)phenyl]propane (refractive index: 1.54, high viscosity liquid)
TEGDMA: triethylene glycol dimethacrylate (refractive index: 1.46)
UDMA: 1,6-bis(methacryloxyethyloxycarbonylamino)-2,2,4-(or -2,4,4-)trimethylhexane (refractive index: 1.48)
Bis-MPEPP: 2,2-bis(4-methacryloxypolyethoxyphenyl)propane (refractive index: 1.54)

Glass Powder

A glass: obtained by treating a glass (refractive index: 1.60, average particle diameter: 5 μm) comprising 40 weight % of silicon dioxide, 40 weight % of barium oxide, 10 weight % of boron oxide and 10 weight % of aluminum oxide, with 1 weight % of [3-(methacryloyloxy)propyl]trimethoxysilane in a conventional manner B glass: obtained by treating a glass (refractive index: 1.60, average particle diameter: 1 μm) comprising 40 weight % of silicon dioxide, 40 weight % of barium oxide, 10 weight % of boron oxide and 10 weight % of aluminum oxide, with 3 weight % of [3-(methacryloyloxy)propyl]trimethoxysilane in a conventional manner C glass: obtained by treating a glass (refractive index: 1.55, average particle diameter: 1 μm) comprising 50 weight % of silicon dioxide, 30 weight % of barium oxide, 10 weight % of boron oxide and 10 weight % of aluminum oxide, with 3 weight % of [3-(methacryloyloxy)propyl]trimethoxysilane in a conventional manner Fine Particle Silica R-812: obtained by hydrophobic treatment of colloidal silica having an average particle diameter of 0.007 μm with dimethyldichlorosilane (proportion of particles having diameters of not less than 0.01 μm: about 10%, a product of Nippon Aerosil Co., Ltd.)

Preparation of Samples and Measurement of Various Properties

Measurement of a Refractive Index

The refractive index was measured at 20° C. according to the usual method by the use of an Abbe refractometer (a product of Atago Co., Ltd., Model: 1T).

Curing of a Composition

A dental composition (composite resin) experimentally prepared was filled in a mold in a predetermined shape and irradiated with visible rays for 60 seconds by-the use of a visible ray irradiator (LIGHTEL, a product of Kuraray Co., Ltd.) to cure the composition.

Flexural Strength and X-ray Contrast Property

Tests were carried out in accordance with 7.11 (flexural strength) and 7.14 (X-ray contrast property) of ISO-4049 (2000).

The flexural strength was measured by the use of an autograph AGS-2000G manufactured by Shimadzu Corporation at a crosshead speed of 1 mm/min. Furthermore, the X-ray contrast property was measured by X-ray photographing a circular cured product having a thickness of 2.0 mm by the use of an X-ray control apparatus (PCX-100, a product of Asahi Roentgen Industries Co., Ltd.) and then calculating the density of the photographed image as an Al equivalent (%) by a densitometer (PDA15, a product of Konica Corporation), based on the density (100%) of a photographed image of an Al plate of the same height.

Light Transmittance (Transparency)

A Teflon mold having a thickness of 1 mm with a rectangular hole of 10 mm (width)×25 mm (length) was filled with a dental composition (composite resin), and then sandwiched between a polyester film and a glass plate, and irradiated with visible rays for 60 seconds per spot by the use of a visible ray irradiator (LIGHTEL, a product of Kuraray Co., Ltd.) to cure the composition. Making reference to the description of 7.12.3.3 of ISO4049 (2000), irradiation with visible rays was carried out such that the whole sample should be irradiated with the rays uniformly and sufficiently. The light transmittance of the sample at a wavelength of 480 nm was measured by the use of an ultraviolet-visible spectrophotometer (UV-160A, a product of Shimadzu Corporation).

Evaluation of Polymerization Shrinkage of a Composition

As shown in FIG. 1, an alumina ceramic tube having an inner diameter of 6 mm and a height of 5 mm was filled with a dental composition (composite resin). At this time, in order to prevent disconnection of the polymerized dental composition (composite resin) from the tube due to shrinkage, the tube was sufficiently filled with the composition such that the composition came out of one end of the tube and covered the tube. Then, the dental composition (composite resin) filled in the tube was irradiated with a light for 180 seconds from the upper surface side of the tube by the use of a visible ray irradiator (LIGHTEL, a product of Kuraray Co., Ltd.) to cure the dental composition (composite resin) in the tube. There-after, the tube filled with the dental composition was placed in an industrial visible ray irradiator (α-Light II, a product of Morita Seisakusho K.K.) and irradiated with visible rays around the tube for 300 seconds to completely cure the dental composition (composite resin) present inside and outside the tube.

After the curing, the alumina tube was cut at the position of 2 mm from the top of the tube. The cut surface was subjected to mirror grinding and cleaned by an ultrasonic cleaner. Then, the gap formed between the cured product and the tube was measured at 8 spots, and the total of widths of the gaps at the facing two measuring spots was taken as a gap width due to polymerization shrinkage.

Example 13

(Preparation of a Composite Resin)

In a monomer mixture (refractive index: 1.58) mixed with 70 parts by weight of MNA-80 and 30 parts by weight of Bis-MPEPP, 0.5 part by weight of camphorquinone and 0.5 part by weight of ethyl N,N-dimethylaminobenzoate were dissolved. The resulting monomer was mixed with 400 parts by weight of the A glass and 20 parts by weight of R-812 to prepare a dental composition as a homogeneous paste. The polymerization shrinkage of a cured product of the dental composition was extremely small, as shown as a gap width in Table 1. The refractive index of the cured product of the dental composition was 1.60.

The flexural strength, light transmittance and X-ray contrast property of the cured product of the dental composition are set forth in Table 1.

Example 14

(Preparation of a Composite Filler)

In a monomer mixture (refractive index: 1.58) mixed with 75 parts by weight of MNA-80 and 25 parts by weight of TEGDMA, 0.5 part by weight of benzoyl peroxide was dissolved. The resulting monomer and 400 parts by weight of the B glass were sufficiently mixed to prepare a homogeneous paste. The paste was heated at 120° C. for 15 minutes by a compressing molding machine with application of pressure to cure the paste. The paste was pulverized by a ball mill and sieved to prepare a composite filler A having an average particle diameter of about 20 μm.

(Preparation of a composite Resin)

In a monomer mixture (refractive index: 1.58) mixed with 75 parts by weight of MNA-80 and 25 parts by weight of TEGDMA, 0.5 part by weight of camphorquinone and 0.5 part by weight of ethyl N,N-dimethylaminobenzoate were dissolved. The resulting monomer was mixed with 350 parts by weight of the A glass, 50 parts by weight of the composite filler A and 30 parts by weight of R-812 to obtain a dental composition as a homogeneous paste. The polymerization shrinkage of a cured product of the dental composition was extremely small, as shown as a gap width in Table 1. The refractive index of the cured product of the dental composition was 1.60.

The flexural strength, light transmittance and X-ray contrast property of the cured product of the dental composition are set forth in Table 1.

Example 15

(Preparation of a Composite Resin)

In a monomer mixture (refractive index: 1.58) mixed with 70 parts by weight of MNA-81 and 30 parts by weight of Bis-MPEPP, 0.5 part by weight of camphorquinone and 0.5 part by weight of ethyl N,N-dimethylaminobenzoate were dissolved. The resulting monomer was mixed with 400 parts by weight of the A glass and 20 parts by weight of R-812 to obtain a dental composition as a homogeneous paste. The polymerization shrinkage of a cured product of the dental composition was extremely small, as shown as a gap width in Table 1. The refractive index of the cured product of the dental composition was 1.60.

The flexural strength, light transmittance and X-ray contrast property of the cured product of the dental composition are set forth in Table 1.

Example 16

(Preparation of a Composite Resin)

In a monomer mixture (refractive index: 1.58) mixed with 70 parts by weight of MNA-82 and 30 parts by weight of Bis-MPEPP, 0.5 part by weight of camphorquinone and 0.5 part by weight of ethyl N,N-dimethylaminobenzoate were dissolved. The resulting monomer was mixed with 400 parts by weight of the A glass and 20 parts by weight of R-812 to obtain a dental composition as a homogeneous paste. The polymerization shrinkage of a cured product of the dental composition was extremely small, as shown as a gap width in Table 1. The refractive index of the cured product of the dental composition was 1.60.

The flexural strength, light transmittance and X-ray contrast property of the cured product of the dental composition are set forth in Table 1.

Example 17

(Preparation of a Composite Resin)

In a monomer mixture (refractive index: 1.58) mixed with 70 parts by weight of MNA-83 and 30 parts by weight of Bis-MPEPP, 0.5 part by weight of camphorquinone and 0.5 part by weight of ethyl N,N-dimethylaminobenzoate were dissolved. The resulting monomer was mixed with 400 parts by weight of the A glass and 20 parts by weight of R-812 to obtain a dental composition as a homogeneous paste. The polymerization shrinkage of a cured product of the dental composition was extremely small, as shown as a gap width in Table 1. The refractive index of the cured product of the dental composition was 1.60.

The flexural strength, light transmittance and X-ray contrast property of the cured product of the dental composition are set forth in Table 1.

Example 18

(Preparation of a Composite Resin)

In a monomer mixture (refractive index: 1.58) mixed with 70 parts by weight of MNA-84 and 30 parts by weight of Bis-MPEPP, 0.5 part by weight of camphorquinone and 0.5 part by weight of ethyl N,N-dimethylaminobenzoate were dissolved. The resulting monomer was mixed with 400 parts by weight of the A glass and 20 parts by weight of R-812 to obtain a dental composition as a homogeneous paste. The polymerization shrinkage of a cured product of the dental composition was extremely small, as shown as a gap width in Table 1. The refractive index of the cured product of the dental composition was 1.60.

The flexural strength, light transmittance and X-ray contrast property of the cured product of the dental composition are set forth in Table 1.

Example 19

(Preparation of a Composite Resin)

In a monomer mixture (refractive index: 1.58) mixed with 70 parts by weight of MNA-85 and 30 parts by weight of Bis-MPEPP, 0.5 part by weight of camphorquinone and 0.5 part by weight of ethyl N,N-dimethylaminobenzoate were dissolved. The resulting monomer was mixed with 400 parts by weight of the A glass and 20 parts by weight of R-812 to obtain a dental composition as a homogeneous paste. The polymerization shrinkage of a cured product of the dental composition was extremely small, as shown as a gap width in Table 1. The refractive index of the cured product of the dental composition was 1.60.

The flexural strength, light transmittance and X-ray contrast property of the cured product of the dental composition are set forth in Table 1.

Example 20

(Preparation of a Composite Resin)

In a monomer mixture (refractive index: 1.58) mixed with 70 parts by weight of MNA-92 and 30 parts by weight of Bis-MPEPP, 0.5 part by weight of camphorquinone and 0.5 part by weight of ethyl N,N-dimethylaminobenzoate were dissolved. The resulting monomer was mixed with 400 parts by weight of the A glass and 20 parts by weight of R-812 to obtain a dental composition as a homogeneous paste. The polymerization shrinkage of a cured product of the dental composition was extremely small, as shown as a gap width in Table 1. The refractive index of the cured product of the dental composition was 1.60.

The flexural strength, light transmittance and X-ray contrast property of the cured product of the dental composition are set forth in Table 1.

Example 21

(Preparation of a Composite Resin)

In a monomer mixture (refractive index: 1.58) mixed with 70 parts by weight of MNA-94 and 30 parts by weight of Bis-MPEPP, 0.5 part by weight of camphorquinone and 0.5 part by weight of ethyl N,N-dimethylaminobenzoate were dissolved. The resulting monomer was mixed with 400 parts by weight of the A glass and 20 parts by weight of R-812 to obtain a dental composition as a homogeneous paste. The polymerization shrinkage of a cured product of the dental composition was extremely small, as shown as a gap width in Table 1. The refractive index of the cured product of the dental composition was 1.60.

The flexural strength, light transmittance and X-ray contrast property of the cured product of the dental composition are set forth in Table 1.

Example 22

(Preparation of a Composite Resin)

In a monomer mixture (refractive index: 1.58) mixed with 70 parts by weight of MNA-104 and 30 parts by weight of Bis-MPEPP, 0.5 part by weight of camphorquinone and 0.5 part by weight of ethyl N,N-dimethylaminobenzoate were dissolved. The resulting monomer was mixed with 400 parts by weight of the A glass and 20 parts by weight of R-812 to obtain a dental composition as a homogeneous paste. The polymerization shrinkage of a cured product of the dental composition was extremely small, as shown as a gap width in Table 1. The refractive index of the cured product of the dental composition was 1.60.

The flexural strength, light transmittance and X-ray contrast property of the cured product of the dental composition are set forth in Table 1.

Example 23

(Preparation of a Composite Resin)

In a monomer mixture (refractive index: 1.58) mixed with 70 parts by weight of MNA-105 and 30 parts by weight of Bis-MPEPP, 0.5 part by weight of camphorquinone and 0.5 part by weight of ethyl N,N-dimethylaminobenzoate were dissolved. The resulting monomer was mixed with 400 parts by weight of the A glass and 20 parts by weight of R-812 to obtain a dental composition as a homogeneous paste. The polymerization shrinkage of a cured product of the dental composition was extremely small, as shown as a gap width in Table 1. The refractive index of the cured product of the dental composition was 1.60.

The flexural strength, light transmittance and X-ray contrast property of the cured product of the dental composition are set forth in Table 1.

Example 24

(Preparation of a Composite Resin)

In a monomer mixture (refractive index: 1.58) mixed with 70 parts by weight of MNA-106 and 30 parts by weight of Bis-MPEPP, 0.5 part by weight of camphorquinone and 0.5 part by weight of ethyl N,N-dimethylaminobenzoate were dissolved. The resulting monomer was mixed with 400 parts by weight of the A glass and 20 parts by weight of R-812 to obtain a dental composition as a homogeneous paste. The polymerization shrinkage of a cured product of the dental composition was extremely small, as shown as a gap width in Table 1. The refractive index of the cured product of the dental composition was 1.60.

The flexural strength, light transmittance and X-ray contrast property of the cured product of the dental composition are set forth in Table 1.

Example 25

(Preparation of a Composite Resin)

In a monomer mixture (refractive index: 1.58) mixed with 70 parts by weight of MNA-107 and 30 parts by weight of Bis-MPEPP, 0.5 part by weight of camphorquinone and 0.5 part by weight of ethyl N,N-dimethylaminobenzoate were dissolved. The resulting monomer was mixed with 400 parts by weight of the A glass and 20 parts by weight of R-812 to obtain a dental composition as a homogeneous paste. The polymerization shrinkage of a cured product of the dental composition was extremely small, as shown as a gap width in Table 1. The refractive index of the cured product of the dental composition was 1.60.

The flexural strength, light transmittance and X-ray contrast property of the cured product of the dental composition are set forth in Table 1.

Comparative Example 1

(Preparation of a Composite Resin)

In a monomer mixture (refractive index: 1.52) mixed with 70 parts by weight of Bis-GMA and 30 parts by weight of TEGDMA, 0.5 part by weight of camphorquinone and 0.5 part by weight of ethyl N,N-dimethylaminobenzoate were dissolved. The resulting monomer was mixed with 400 parts by weight of the A glass and 25 parts by weight of R-812 to obtain a dental composition as a homogeneous paste. The polymerization shrinkage of the dental composition was shown as a gap width in Table 1. The refractive index of the cured product of the dental composition was 1.54.

The flexural strength, light transmittance and X-ray contrast property of the cured product of the dental composition are set forth in Table 1.

Comparative Example 2

(Preparation of a Composite Resin)

In a monomer mixture (refractive index: 1.52) mixed with 70 parts by weight of Bis-GMA and 30 parts by weight of TEGDMA, 0.5 part by weight of camphorquinone and 0.5 part by weight of ethyl N,N-dimethylaminobenzoate were dissolved. The resulting monomer was mixed with 350 parts by weight of the C glass and 20 parts by weight of R-812 to obtain a dental composition as a homogeneous paste. The polymerization shrinkage of the dental composition was shown as a gap width in Table 1. The refractive index of the cured product of the dental composition was 1.55.

The flexural strength, light transmittance and X-ray contrast property of the cured product of the dental composition are set forth in Table 1.

Comparative Example 3

(Preparation of a Composite Resin)

In a monomer mixture (refractive index: 1.52) mixed with 35 parts by weight of Bis-GMA, 35 parts by weight of Bis-MPEPP and 30 parts by weight of TEGDMA, 0.5 part by weight of camphorquinone and 0.5 part by weight of ethyl N,N-dimethylaminobenzoate were dissolved. The resulting monomer was mixed with 400 parts by weight of the A glass and 20 parts by weight of R-812 to obtain a dental composition as a homogeneous paste. The polymerization shrinkage of the dental composition was shown as a gap width in Table 1. The refractive index of the cured product of the dental composition was 1.54.

The flexural strength, light transmittance and X-ray contrast property of the cured product of the dental composition are set forth in Table 1.

Comparative Example 4

(Preparation of a Composite Resin)

In a monomer mixture (refractive index: 1.52) mixed with 35 parts by weight of Bis-GMA, 35 parts by weight of Bis-MPEPP, 15 parts by weight of TEGDMA and 15 parts by weight of UDMA, 0.5 part by weight of camphorquinone and 0.5 part by weight of ethyl N,N-dimethylaminobenzoate were dissolved. The resulting monomer was mixed with 400 parts by weight of the A glass and 20 parts by weight of R-812 to obtain a dental composition as a homogeneous paste. The refractive index of the cured product of the dental composition was 1.54.

The flexural strength, light transmittance and X-ray contrast property of the cured product of the dental composition are set forth in Table 1.

Comparative Example 5

(Preparation of a Composite Resin)

In 100 parts by weight of Bis-MPEPP (refractive index: 1.54), 0.5 part by weight of camphorquinone and 0.5 part by weight of ethyl N,N-dimethylaminobenzoate were dissolved. The resulting monomer was mixed with 400 parts by weight of the A glass and 20 parts by weight of R-812 to obtain a dental composition as a homogeneous paste. The refractive index of the cured product of the dental composition was 1.56.

The flexural strength, light transmittance and X-ray contrast property of the cured product of the dental composition are set forth in Table 1.

Comparative Example 6

(Preparation of a Composite Resin)

An attempt to mix Bis-GMA (refractive index; 1.54) with the A glass was made, but they could not be mixed because the viscosity of the Bis-GMA was too high.

TABLE 1

(Flexural strength, light transmittance, X-ray contrast property and polymerization shrinkage of composite resin)

| | Flexural strength (Mpa) | Light transmittance (T %) | X-ray contrast property (%, aluminum base) | Gap width (µm) |
|---|---|---|---|---|
| Example 13 | 124 | 13.4 | 580 | 27.6 |
| Example 14 | 102 | 7.3 | 530 | 22.8 |
| Example 15 | 117 | 14.1 | 580 | 24.3 |
| Example 16 | 120 | 15.0 | 570 | 24.2 |
| Example 17 | 115 | 13.6 | 580 | 30.8 |
| Example 18 | 125 | 12.9 | 560 | 29.1 |
| Example 19 | 118 | 11.0 | 590 | 21.3 |
| Example 20 | 120 | 12.2 | 580 | 28.4 |
| Example 21 | 117 | 13.1 | 570 | 14.6 |
| Example 22 | 109 | 11.7 | 560 | 28.5 |
| Example 23 | 113 | 12.5 | 570 | 17.9 |
| Example 24 | 128 | 10.1 | 560 | 19.0 |
| Example 25 | 103 | 13.3 | 570 | 17.6 |
| Comparative Example 1 | 122 | 0.6 | 580 | 41.5 |
| Comparative Example 2 | 106 | 11.8 | 220 | 46.4 |
| Comparative Example 3 | 121 | 0.6 | 570 | 45.2 |
| Comparative Example 4 | 129 | 0.5 | 580 | — |
| Comparative Example 5 | 103 | 0.8 | 580 | — |

As can be seen from Table 1, with regard to the mechanical strength of the composite resin that is indicated by the flexural strength, there was no big difference between Examples and Comparative Examples, and they had sufficient strengths nearly equal to each other. On the other hand, with regard to both the light transmittance indicating transparency and the X-ray contrast property, the composite resins of Examples exhibited excellent results and had well-balanced transparency and X-ray contrast property. However, the composite resin of Comparative Example 2 showed light transmittance of good value but was inferior to those of Examples and other Comparative Examples in the X-ray contrast property. The composite resins of other Comparative Examples were all equal to the composite resins of Examples in the X-ray contrast property, but they showed light transmittance of much lower values than the composite resins of Examples.

Preparation of a Polymerizable Composition and Preparation of an Optical Part by Curing According to the Present Invention The physical properties of cured products or optical parts (lens) prepared in Examples or Comparative Examples were evaluated in the following methods.

Appearance: Hue, transparency, optical distortion and striae were confirmed visually or using a microscope.

Refractive index and Abbe number: These were measured at 20° C. using a Pulfrich refractometer.

Specific gravity: It was measured by the use of DENSIMETER D-1 (a product of Toyo Seiki Seisaku-sho, Ltd.).

Heat resistance: A glass transition temperature (Tg) was measured from the displacement point of TMA curve of the cured product by the needle soaking method using the Thermomechanical Analysis Method (TMA Method).

<Preparation of a Polymerizable Composition of the Present Invention>

Example 26

To 100.0 g of the compound represented by the formula (1-1) prepared in Example 1, 0.20 g (0.20 weight % based on the total weight of the polymerizable compound) of 2-hydroxy-2-methyl-1-phenylpropane-1-on as a polymerization initiator was added, mixed, stirred and dissolved. Subsequently, the resulting solution was slowly stirred at a room temperature under a reduced pressure for sufficiently degassing until no bubble was recognized, pressurized and filtered using a Teflon filter to obtain 100.0 g of a polymerizable composition, that is, a colorless and transparent liquid.

The following products were obtained and used for a photopolymerization initiator used in the above Preparation Examples and Examples.

2-hydroxy-2-methyl-1-phenylpropane-1-on; Darocure-1173 (manufactured by Ciba Specialty Chemicals Inc.)

Example 27

Preparation of a Cured Product of the Polymerizable Composition of the Present Invention by Photopolymerization The polymerizable composition prepared in Example 26 was fed into a mold manufactured by the use of a silicon rubber as a spacer between two pieces of mirror surface-finished glass plates. Using a metal halide lamp (120 W/cm), the composition was irradiation with ultraviolet rays from both the top and bottom sides of the glass mold for 180 seconds to perform polymerization. When the polymerization was completed, the mold was slowly cooled and a cured product was taken out of the mold. The cured product was heat-treated (annealed) at 120° C. for an hour, and then the thus-obtained cured product was examined. As a result, the cured product was colorless and transparent, and no optical distortion and no striae were confirmed. Furthermore, impact resistance and weather resistance of the obtained cured product were excellent so that there was not any practical problem.

As various properties of the cured product, the refractive index (nd) was 1.617, the Abbe's number (vd) was 25.7, the specific gravity was 1.22, and the glass transition temperature (Tg) was 89° C. Further, the polymerization shrinkage obtained from the specific gravity of the monomer and that of the cured product was 6.0%.

Example 28

100.0 g of a polymerizable composition of a colorless and transparent liquid was obtained in the same manner as in Example 26, except that the compound represented by the formula (1-6) prepared in Example 6 was used instead of the compound represented by the formula (1-1) used in Example 26.

Example 29

A cured product was obtained in the same manner as in Example 27, except that the polymerizable composition prepared in Example 28 was used instead of the polymerizable composition prepared in Example 26 used in Example 27. The thus-obtained cured product was observed. As a result, the cured product was colorless and transparent, and no optical distortion and no striae were confirmed. Furthermore, impact resistance and weather resistance of the obtained cured product were excellent so that there was not any practical problem.

As physical properties of the cured product, the refractive index (nd) was 1.616, the Abbe number (vd) was 24.9, the specific gravity was 1.19, and the glass transition temperature (Tg) was 79° C. Further, the polymerization shrinkage obtained from the specific gravity of the monomer and that of the cured product was not more than 3.0%.

Example 30

100.0 g of a polymerizable composition of a colorless and transparent liquid was obtained in the same manner as in Example 26, except that the compound represented by the formula (1-8) prepared in Example 8 was used instead of the compound represented by the formula (1-1) used in Example 26.

Example 31

A cured product was obtained in the same manner as in Example 27, except that the polymerizable composition prepared in Example 30 was used instead of the polymerizable composition prepared in Example 26 used in Example 27. The thus-obtained cured product was observed. As a result, the cured product was colorless and transparent, and no optical distortion and no striae were confirmed. Furthermore, impact resistance and weather resistance of the obtained cured product were excellent so that there was not any practical problem.

As physical properties of the cured product, the refractive index (nd) was 1.598, the Abbe number (vd) was 27.4, the specific gravity was 1.23, and the glass transition temperature (Tg) was 93.5° C. Further, the polymerization shrinkage obtained from the specific gravity of the monomer and that of the cured product was not more than 6.8%.

Example 32

100.0 g of a polymerizable composition of a colorless and transparent liquid was obtained in the same manner as in Example 26, except that the compound represented by formula (1-10) prepared in Example 10 was used instead of the compound represented by the formula (1-1) used in Example 26.

Example 33

A cured product was obtained in the same manner as in Example 27, except that the polymerizable composition prepared in Example 32 was used instead of the polymerizable composition prepared in Example 26 used in Example 27. The thus-obtained cured product was observed. As a result, the cured product was colorless and transparent, and no optical distortion and no striae were confirmed. Furthermore, impact resistance and weather resistance of the obtained cured product were excellent so that there was not any practical problem.

As physical properties of the cured product, the refractive index (nd) was 1.592, the Abbe number (vd) was 29.4, the specific gravity was 1.30, and the glass transition temperature (Tg) was 116° C. Further, the polymerization shrinkage obtained from the specific gravity of the monomer and that of the cured product was 5.8%.

Example 34

100.0 g of a polymerizable composition of a colorless and transparent liquid was obtained in the same manner as in Example 26, except that the compound represented by the formula (1-11) prepared in Example 11 was used instead of the compound represented by the formula (1-1) used in Example 26.

Example 35

A cured product was obtained in the same manner as in Example 27, except that the polymerizable composition prepared in Example 34 was used instead of the polymerizable composition prepared in Example 26 used in Example 27. The thus-obtained cured product was observed. As a result, the cured product was colorless and transparent, and no optical distortion and no striae were confirmed. Furthermore, impact resistance and weather resistance of the obtained cured product were excellent so that there was not any practical problem.

As physical properties of the cured product, the refractive index (nd) was 1.596, the Abbe number (vd) was 32.7, the specific gravity was 1.24, and the glass transition temperature (Tg) was 101° C. Further, the polymerization shrinkage obtained from the specific gravity of the monomer and that of the cured product was 4.6%.

Example 36

100.0 g of a polymerizable composition of a colorless and transparent liquid was obtained in the same manner as in Example 26, except that the compound represented by the formula (1-12) prepared in Example 12 was used instead of the compound represented by the formula (1-1) used in Example 26.

Example 37

A cured product was obtained in the same manner as in Example 27, except that the polymerizable composition prepared in Example 36 was used instead of the polymerizable composition prepared in Example 26 used in Example 27. The thus-obtained cured product was observed. As a result, the cured product was colorless and transparent, and no optical distortion and no striae were confirmed. Furthermore, impact resistance and weather resistance of the obtained cured product were excellent so that there was not any practical problem.

As physical properties of the cured product, the refractive index (nd) was 1.622, the Abbe number (vd) was 26.3, the specific gravity was 1.22, and the glass transition temperature (Tg) was 94° C. Further, the polymerization shrinkage obtained from the specific gravity of the monomer and that of the cured product was not more than 3.0%.

Example 38

Preparation of a Lens

After sufficiently degassing the polymerizable composition prepared in Example 30 under a reduced pressure, the composition was poured into a mold (adjusted to a minus lens shape) comprising a glass mold and a tape. Using a metal halide lamp (120 W/cm), the composition was irradiated with ultraviolet rays from both the top and bottom sides of the mold for 60 seconds, and then, the composition was heated at 70° C. for 3 hours to carry out an annealing process. When the polymerization was completed, the mold was allowed to stand until it was cooled down to a room temperature to obtain a colorless and transparent minus lens having a diameter of 30 mm and a center thickness of 1.3 mm. The thus-obtained lens was colorless and transparent, and optically uniform with no optical distortion, no striae and the like being observed.

Furthermore, heat resistance (heat distortion temperature), impact resistance and weather resistance of the obtained lens according to the present invention were excellent so that there was not any practical problem.

As can be seen from the results according to Examples above, the polymerizable composition containing the (meth) acrylic ester compound represented by the general formula (1) according to the present invention can be polymerized, cured and molded within a short period of time by photopolymerization. The obtained cured product and optical part according to the present invention are superior in the transparency and optical properties (high refractive index), and also combine thermal properties, mechanical properties and weather resistance.

INDUSTRIAL APPLICABILITY

The polymerizable composition containing the (meth) acrylic ester compound represented by the general formula (1) according to the present invention can be polymerized, cured and molded within a short period of time by photopolymerization. The obtained cured product is superior in the transparency and optical properties (high refractive index), and also combines thermal properties, mechanical properties and weather resistance. So, it is useful as a dental material or a material for use in various optical parts. In particular, the dental material and the dental composition containing the compound represented by the general formula (1) according to the present invention are very useful as the appropriate material and composition because they are superior in curability, and also combine transparency, X-ray contrast property and low polymerization shrinkage, while retaining various properties required for dental materials (for example, flexural strength and the like).

Furthermore, the cured product and optical part obtained by the present invention are superior in the transparency and optical properties (high refractive index), and also combines thermal properties, mechanical properties and weather resistance. From these properties, they can be used, for example, for various plastic lenses such as a spectacle lens for vision correction, a Fresnel lens for use in a liquid crystal projector or a projector television, a lenticular lens, a contact lens and the like, a sealing material for a light emitting diode (LED), an optical waveguide, an optical adhesive to be used for the joint of an optical lens and an optical waveguide, an anti-reflection film to be used for an optical lens, and transparent coating or transparent substrate to be used for a liquid crystal display-related member (substrate, light guiding plate, film, sheet and the like).

The invention claimed is:

1. A (meth)acrylic ester compound represented by the general formula (1),

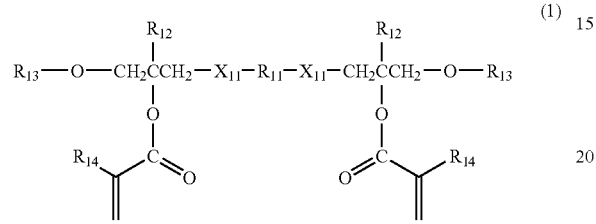

wherein, in the formula, $R_{12}$ represents a hydrogen atom or a methyl group; $R_{13}$ represents an unsubstituted aryl group or a substituted aryl group wherein the substituent is selected from the group consisting of an aralkyl group, an aralkyloxy group and an aryloxy group; $R_{14}$ represents a hydrogen atom or a methyl group; $X_{11}$ represents an oxygen atom or a sulfur atom; and $R_{11}$ represents a group represented by any one of the formulae (2) to (4),

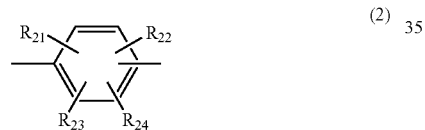

wherein, in the formula (2), $R_{21}$, $R_{22}$, $R_{23}$ and $R_{24}$ are each independently a hydrogen atom, an alkyl group, an alkoxy group or a nitro group,

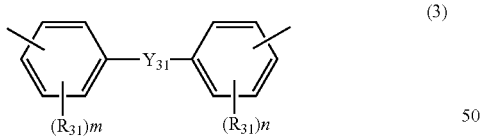

wherein, in the formula (3), $R_{31}$ and $R_{32}$ are each independently an alkyl group, an alkenyl group, an aralkyl group, an aryl group, an alkoxy group or a nitro group; and $Y_{31}$ represents a single bond, —C(CH$_3$)(phenyl)- group, —O— group, —S— group, —SO$_2$— group, a group represented by the formula (3-a) or a group represented by the formula (3-b),

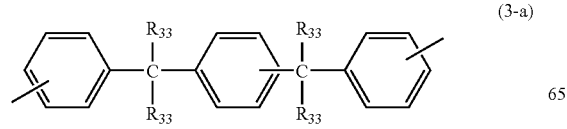

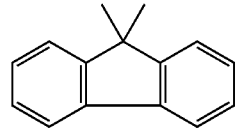

wherein, in the above groups, $R_{33}$s are each independently a hydrogen atom, an alkyl group or an aryl group; and m and n are each independently 0 or an integer of 1 to 4,

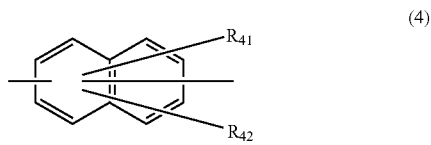

wherein, in the formula (4), $R_{41}$ and $R_{42}$ are each independently a hydrogen atom or an alkyl group.

2. A polymerizable composition containing the compound represented by the general formula (1) as described in claim 1.

3. A cured product obtained by polymerizing the polymerizable composition as described in claim 2.

4. A dental material containing a compound represented by the general formula (1),

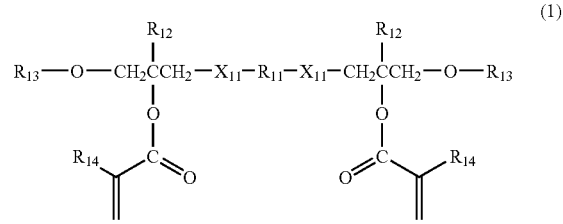

wherein, in the formula, $R_{12}$ represents a hydrogen atom or a methyl group; $R_{13}$ represents an unsubstituted aryl group or a substituted aryl group wherein the substituent is selected from the group consisting of an aralkyl group, an aralkyloxy group and an aryloxy group; $R_{14}$ represents a hydrogen atom or a methyl group; $X_{11}$ represents an oxygen atom or a sulfur atom; and $R_{11}$ represents a group represented by any one of the formulae (2) to (4),

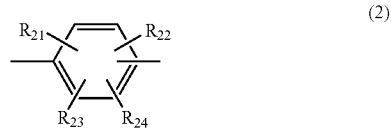

wherein, in the formula (2), $R_{21}$, $R_{22}$, $R_{23}$ and $R_{24}$ are each independently a hydrogen atom, an alkyl group, an alkoxy group or a nitro group,

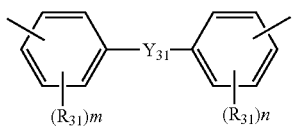
(3)

wherein, in the formula (3), $R_{31}$ and $R_{32}$ are each independently an alkyl group, an alkenyl group, an aralkyl group, an aryl group, an alkoxy group or a nitro group; and $Y_{31}$ represents a single bond, —C(CH$_3$)(phenyl)- group, —O— group, —S— group, —SO— group, a group represented by the formula (3-a) or a group represented by the formula (3-b),

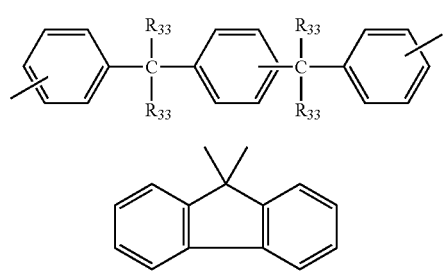
(3-a)

(3-b)

wherein, in the above groups, $R_{33}$s are each independently a hydrogen atom, an alkyl group or an aryl group; and m and n are each independently 0 or an integer of 1 to 4,

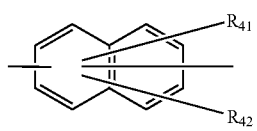
(4)

wherein, in the formula (4), $R_{41}$ and $R_{42}$ are each independently a hydrogen atom or an alkyl group.

5. A dental composition containing (A) a polymerizable

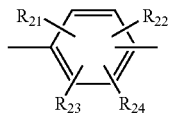

compound and (B) a polymerization initiator, wherein the polymerizable compound is the compound represented by the general formula (1) as described in claim 1.

6. The dental composition according to claim 5, wherein the dental composition as described in claim 5 further contains (C) a filler.

7. The dental composition according to claim 6, wherein the dental composition further contains other polymerizable compounds in addition to the compound represented by the general formula (1).

8. The dental composition according to claim 7, wherein the refractive index of the cured product after polymerization is not less than 1.55.

9. An optical part comprising the cured product as described in claim 3.

10. A polymerizable composition containing the compound represented by the general formula (1) as described in claim 1.

11. A cured product obtained by polymerizing the polymerizable composition as described in claim 10.

12. The dental composition according to claim 5, wherein the dental composition further contains other polymerizable compounds in addition to the compound represented by the general formula (1).

13. The dental composition according claim 6, wherein the refractive index of the cured product after polymerization is not less than 1.55.

14. The dental composition according claim 5, wherein the refractive index of the cured product after polymerization is not less than 1.55.

15. The dental composition according claim 12, wherein the refractive index of the cured product after polymerization is not less than 1.55.

16. An optical part comprising the cured product as described in claim 11.

17. The (meth)acrylic ester compound according to claim 1, wherein $R_{13}$ is selected from the group consisting of a phenyl group, a 4-phenylphenyl group, a 3-phenylphenyl group, a 2-phenylphenyl group, a 1-naphthyl group, a 2-naphthyl group, a 4-phenoxyphenyl group, a 3-phenoxyphenyl group, and a 2-phenoxyphenyl group.

18. The dental material according to claim 4, wherein $R_{13}$ is selected from the group consisting of a phenyl group, a 4-phenylphenyl group, a 3-phenylphenyl group, a 2-phenylphenyl group, a 1-naphthyl group, a 2-naphthyl group, a 4-phenoxyphenyl group, a 3-phenoxyphenyl group, and a 2-phenoxyphenyl group.

* * * * *